US007939635B2

(12) United States Patent
Stracke et al.

(10) Patent No.: US 7,939,635 B2
(45) Date of Patent: May 10, 2011

(54) AUTOTAXIN: MOTILITY STIMULATING PROTEIN USEFUL IN CANCER DIAGNOSIS AND THERAPY

(75) Inventors: Mary Stracke, Rockville, MD (US); Lance Liotta, Potomac, MD (US); Elliott Schiffmann, Chevy Chase, MD (US); Henry Krutzch, Bethesda, MD (US); Jun Murata, Tovama (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 736 days.

(21) Appl. No.: 11/060,102

(22) Filed: Feb. 16, 2005

(65) Prior Publication Data
US 2006/0275865 A1    Dec. 7, 2006

Related U.S. Application Data

(60) Continuation of application No. 10/147,140, filed on May 15, 2002, now abandoned, which is a division of application No. 09/483,831, filed on Jan. 17, 2000, now Pat. No. 6,417,338, which is a continuation of application No. 08/977,221, filed on Nov. 24, 1997, now Pat. No. 6,084,069, which is a division of application No. 08/346,455, filed on Nov. 28, 1994, now Pat. No. 5,731,167, which is a continuation-in-part of application No. 08/249,182, filed on May 25, 1994, now abandoned, which is a continuation-in-part of application No. 07/822,043, filed on Jan. 17, 1992, now Pat. No. 5,449,753.

(51) Int. Cl.
C07K 16/00   (2006.01)
C12P 21/08   (2006.01)
C07K 17/00   (2006.01)

(52) U.S. Cl. ................................ 530/387.1; 530/388.23
(58) Field of Classification Search .................. None
See application file for complete search history.

(56) References Cited

U.S. PATENT DOCUMENTS 5,003,047 A    3/1991   Yarmush et al.
5,604,106 A *  2/1997   Liotta et al. .................. 435/7.23
5,731,167 A    3/1998   Stracke et al.

FOREIGN PATENT DOCUMENTS
WO        WO 93/14202        7/1993

OTHER PUBLICATIONS

Lederman e.t al. Molecular Immunology 1991. 28: 1171-1181.*
Li et al. (PNAS 1980. 77: 3211-3214.*
Campbell. Monoclonal Antibody Technology. 1984. Published by Elsevier Science Publishing Company Inc. pp. 1-32.*
Narita et al., *J. Biol. Chem.*, 28235-28242 (1994).
Stracke et al., *J. Biol. Chem.*, 267(4), 2524-2529 (Feb. 5, 1992).
Alberts et al., *Molecular Biology of the Cell*, Garland Publishing, Inc. (1983).
Atnip et al., *Biochem. and Biophys. Res. Comm.*, 146, 996-1002 (Aug. 14, 1987).
Gherardi et al., Proc. Natl. Acad. Sci., 86, 5844-5848 (Aug. 1989).
Liotta et al., *Proc. Natl. Acad. Sci.*, 83 3302-3306 (May 1986).
Murata et al., *J. Biol. Chem.*, 269 (48) 30479-30484 (Dec. 2, 1994).
Ohnishi et al., J. Neurosurg., 73, 881-888 (Dec. 1990).
Rosen et al., *Soc. for Exp. Biol. and Med.*, 34-43 (1990).
Schor et al., J. Cell Sci., 391-399 (1988).
Silletti et al., *Cancer Research*, 3507-3511 (Jul. 1, 1991).
Singer et al., *Ann. Rev. Cell. Biol.*, 337-362.
Stoker et al., *Nature*, 327, 239-242 (May 1987).
Stracke et al., *J. Biol. Chem.*, 264, 21544-21549 (Dec. 25, 1989).
Todaro et al., *Proc. Natl. Acad. Sci*, 77 (9), 5258-5262 (Sep. 1990).
Watanabe et al., *J. Biol. Chem.*, 20, 13442-13448 (Jul. 15, 1991).
Warn et al., *Nature*, 340, 186-187 (1989).
Weidner et al., *J. Cell Biol.*, 111, 2097-2108 (Nov. 1990).
Wells et al., *Biochem.*, 29, 8509-8517 (1990).
Witkowski et al., *Biochem.*, 38, 11643-11650 (1999).
Yoshida et al., *Int. J. Cancer*, 123-132 (1970).

* cited by examiner

*Primary Examiner* — Chun Dahle
(74) *Attorney, Agent, or Firm* — Leydig, Voit & Mayer, Ltd.

(57) ABSTRACT

The present invention relates, in general, to autotaxin. In particular, the present invention relates to a DNA segment encoding autotaxin; recombinant DNA molecules containing the DNA segment; cells containing the recombinant DNA molecule; a method of producing autotaxin; antibodies to autotaxin; and identification of functional domains in autotaxin.

2 Claims, 16 Drawing Sheets

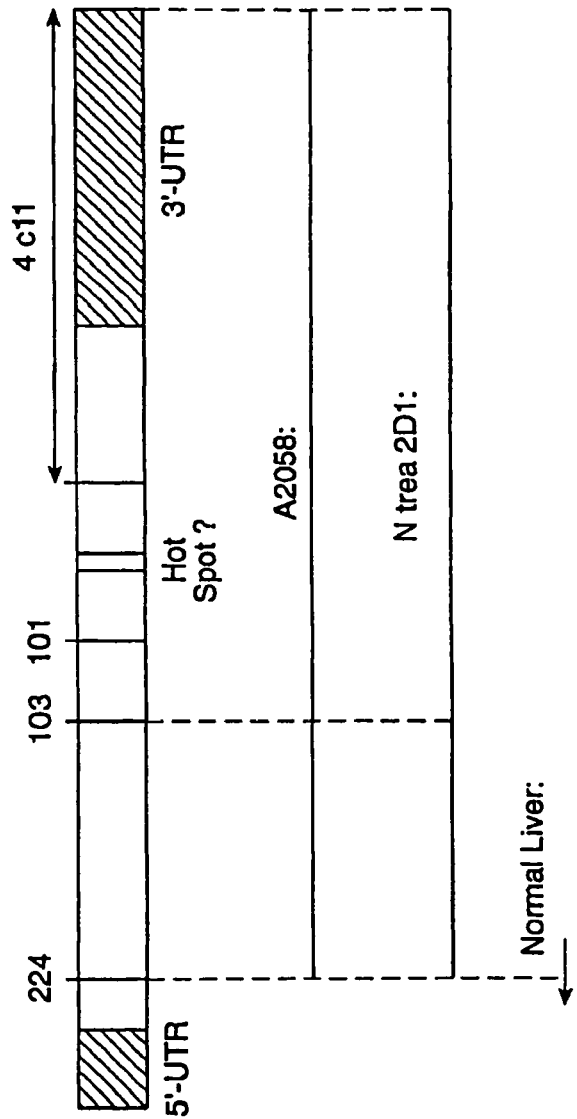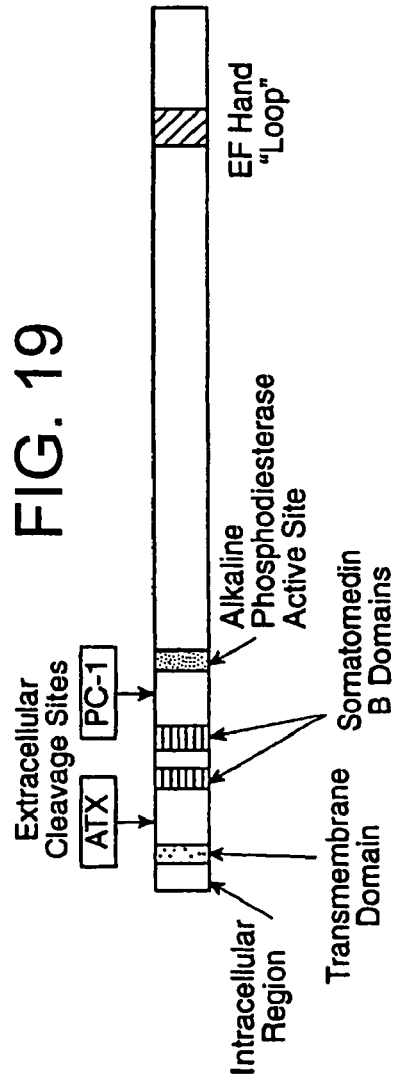

← 125kDA

FIG. 18A

```
hATX                                                  MARRSSFQSCQIISLFTFAVGVSICLGFTAHRIKRAEGWEEGPPTVLSDSPWTNISGSCKGRCFELQEAGPPDCRCDNLCKSYTSCCHDF    90 hPC1   MDVGEEPLEKAARARTAKDPNTYKVLSLVLSVCVLTTIL........GCIFG....LKPSCAKEVK..SCKGRCF...ERTFGNCRCDAACVELGHCCLDY   84 hATX   DELCLKTARGWECTKDRCGEVRNEENACHCSEDCLARGDCCTNYQVVCKGESHWVDDDCEEIKAAECPAGFVRPPLIIFSVDGFRASYMKKGSKVMPNIE   190 hPC1   QETCIEPEHIWTCNKFRCGEKRLTRSLCACSDDCKDKGDCCINYSSVCQGEKSWVEEPCESINEPQCPAGFETPPTLLFSLDGFRAEYLHTWGGLLPVIS   184 hATX   KLRSCGTHSPYMRPVYPKTFPNLYTLATGLYPESHGIVGNSMYDPVFDATFHLRGREKFNHRWGGQPLWITATKQGVKAGTFFWS................   272 hPC1   KLKKCGTYTKNMRPVYPKTFPNHYSIVTGLYPESHGIIDNKMYDPKMNASFSLKSKEKFNPEWYKGEPIWTAKYQGLKSGTFFWPGSDVEINGIFPDI   284 hATX   .....VVIPHERRILQTILRWLTLPDHERPSVYAFYSEQPDFSGHKYGPFGPEESSYGSPFTPAKRPRKVAPKRRQERPVAPPKKRRRKIHRMDHYAAET   372 hPC1   YKMYNGSVPFEERILAVLQWLQLPKDERPHFYTLYLEEPDSSGHSYGPVSSE............................................   336 hATX   RQDKMTNPLREIDKIVGQLMDGLKQLMDGLKQLKLRRCVNVIFVGDHGMEDVTCDRTEFLSNYLTNVDDIITLVPGTLGRIR..SKFSNN..AKYDPKAIIANLTCKKPD   470 hPC1   ....VIKALQRVDGMVGMLMDGLKELNLHRCLNLILTSDHGMEQGSCKKYIYLNKYLGDVKNIKVIYGPAARLRPSDVPDKYYSPNYEGIARNLSCREPN   432 hATX   QHFKPYLKQHLPKRLHYANNRRIEDIHLLVERRWHVARKPLDVYKKPSGKCFFQGDHGFDNKVNSMQTVPVGYGPTFKYKTKVPPFENIELYNVMCDLLIG   570 hPC1   QHFKPYLKHGLPKRLHFAKSDRIEPLTFYLDPQWQLALNPSE..RKYCGSGF....HGSDNVFSNMQALFVGYGPGFKHGIEADTFENIEVVNLMCDLLN   526
```

FIG. 18B

```
hATX  LKPAPNNGTHGSLNHLLRTNTFRPTMPEEVTRPNYPGIMYLQSDFDLGCTCDDKVEPKNKLD.ELNKRLHTKGSTEERHLLYGRPAVLYRTR.YDLLYHT 668
          ||||||||||||  ||| |   |||||    |   ||                       ||||||||||  ||||||||      ||||||
hPC1  LTPAPNNGTHGSLNHLLKNPVYTPKHPKEV.HPLVQCPFTRNPRDNLGCSCNPSILPIEDFQTQFNLTVAEEKIIKHETLPYGRPRVLQKENTICLLSQH 625 hATX  DFESGYSEIFLMLLWTSYTVSKQAEVSSVPDHLTSCVRPDVRVSPSFSQNCLAYKNDKQMSYGFLFPPYLSSSPEAKY.DAFLVTNMVPMYPAFKRVWNY 767
      ||||  |||||||||||||||   ||||    ||| ||           ||| ||||||||||||||||| |||||  ||||| |||||| ||||  |
hPC1  QFMSGYSQDILMPLWTSYTVDRNDSFS...TEDFSNCLYQDFRIPLSPVHKCSFYKNNTKVSYGFLSPPQLNKNSSGIYSEALLTTNIVPMYQSFQVIWRY 723 hATX  FQRVLVKKYASERNGVNNISGPIFDYDYDGLHDTEDKIKQ...YVEGSSIPVPTHYYSIITSCLDFTQPADKCDGPLSVSSFILPHRPDNEESCNSSEDE 875
      | | |  |||||||||||||||||||||||||||||||       |  ||||||||||||||||| ||  |||        ||| ||| || ||| |
hPC1  FHDTLLRKYAEERNGVNVVSGPVFDFDYDGRCDSLENLRQKRRVIRNQEILIPTHFFIVLTSCKDTSQTPLHCEN.LDTLAFILPHRTDNSESCVHGKHD 822 hATX  SKWVEELMKMHTARVRDIEHLTSLDFFRKTSRSYPEILTLKTYLHTYESEI 915  (SEQ ID NO: 69)
      | ||||||| ||   |||||||||||||||||||||||||||||||||||
hPC1  SSWVEELLMLHRARITDVEHITGLSFYQQRKEPVSDILKLKTHLPTFSQED 873  (SEQ ID NO: 70)
```

AUTOTAXIN: MOTILITY STIMULATING PROTEIN USEFUL IN CANCER DIAGNOSIS AND THERAPY

This application is a continuation of application Ser. No. 10/147,140 filed May 15, 2002 (abandoned), which is a divisional of application Ser. No. 09/483,831 filed Jan. 17, 2000 (issued as U.S. Pat. No. 6,417,338), which is a continuation of application Ser. No. 08/977, 221 filed Nov. 24, 1997 (issued as U.S. Pat. No. 6,084,069), which is a divisional of application Ser. No. 08/346,455 filed Nov. 28, 1994 (issued as U.S. Pat. No. 5,731,167), which is a continuation-in-part of application Ser. No. 08/249,182 filed May 25, 1994 (abandoned), which is a continuation-in-part of application Ser. No. 07/822,043 filed on Jan. 17, 1992 (issued as U.S. Pat. No. 5,449,753).

INCORPORATION-BY-REFERENCE OF MATERIAL ELECTRONICALLY FILED

1. Field of the Invention

Incorporated by reference in its entirety herein is a computer-readable nucleotide/amino acid sequence listing submitted concurrently herewith and identified as follows: One 83,520 Byte ASCII (Text) file named 234447SequenceListing_ST25.txt created on Dec. 6, 2010.

The present invention relates, in general, to a motility stimulating and compositions comprising the same. In particular, the present invention relates to a purified form of the protein and peptides thereof, for example, autotaxin (herein alternative referred to as "ATX"); a DNA segment encoding autotaxin; recombinant DNA molecules containing the DNA segment; cells containing the recombinant DNA molecule; a method of producing autotaxin; antibodies to autotaxin; and methods of cancer diagnosis and therapy using the above referenced protein or peptides thereof and DNA segments.

2. Background of the Invention

Cell motility plays an important role in embryonic events, adult tissue remodeling, wound healing, angiogenesis, immune defense, and metastasis of tumor cells (Singer, 1986). In normal physiologic processes, motility is tightly regulated. On the other hand, tumor cell motility may be aberrantly regulated or autoregulated. Tumor cells can respond in a motile fashion to a variety of agents. These include host-derived factors such as scatter factor (Rosen, et al., 1989) and growth factors (Kahan, et al., 1987; Stracke, et al.; Tamm, et al., 1989; Wang, et al. 1990; and Jouanneau, et al. 1991), components of the extracellular matrix (McCarthy, et al. 1984), and tumor-secreted or autocrine factors (Liotta, et al. 1988; Ruff, et al. 1985; Atnip, et al. 1987; Ohnishi, et al. 1990; Silletti, et al. 1991; and Watanabe, et al. 1991).

Many types of host-derived soluble factors act in a paracrine fashion to stimulate cell locomotion. Motility-stimulating proteins called "scatter factors" have been identified which are produced by embryonic fibroblasts and by smooth muscle cells (Stoker, et al. 1987). Scatter factors stimulate random and directed motility by epithelial cells, keratinocytes, vascular endothelial cells and carcinoma cells (Stoker, et al. 1987; Rosen, et al. 1990; and Weidner, et al. 1990), but not fibroblasts. In addition, a number of host-secreted growth factors have been demonstrated to stimulate motility in tumor cells, including nerve growth factor (Kahan, et al. 1987) insulin-like growth factor-I (Stracke, et al. 1988), interleukin-6 (Tamm, et al. 1989), interleukin-8 (Wang, et al. 1990), and acidic fibroblast growth factor (Jouanneau, et al. 1991). These paracrine factors may influence "homing" or the directionality of tumor cell motility.

In contrast to these host-derived factors, many types of tumor cells have been found to produce proteins termed "autocrine motility factors" which stimulate motility by the same tumor cells which make the factor (Liotta, et al. 1986). Autocrine motility factors are not specific for a given type of cancer cell but have a wide spectrum of activity on many types of cancer cells (Kohn, et al. 1990), with little effect on normal fibroblasts or leukocytes.

Autocrine motility factors identified to date act through cell-surface receptors (Stracke, et al. 1987; Nabi, et al. 1990; Watanabe, et al. 1991) resulting in pseudopodial protrusion (Guirguis, et al. 1987) leading to both random and directed migration (Liotta, et al. 1986; Atnip, et al. 1987; Ohnishi, et al. 1990).

Prior studies of human A2058 melanoma cells have demonstrated that these cells are a particularly rich source of autocrine motility factors. An autocrine motility factor with a molecular mass of approximately 60 kDa has been previously isolated from the conditioned media of these cells. (Liotta, et al. 1986). Similar tumor cells derived or induced factors with the same molecular weight have subsequently been reported and purified by several investigators (Atnip, et al. 1987; Schnor, et al. 1988; Ohnishi, et al. 1990; Silletti, et al. 1991; Watanabe et al. 1990). Such factors are thought to play a key role in tumor cell invasion.

Most of the motility factors identified to date have not been purified to homogeneity and have not been sequenced. The novel tumor motility factor of the present invention, named herein as autotaxin ("ATX"), has been purified and verified to be a homogeneous sample by two-dimensional gel electrophoresis. The protein of the present invention is unique from any previously identified or purified motility factor. The molecular size of ATX is about 125 kilo Daltons ("kDa") and it has an isoelectric point of approximately 7.7. ATX stimulates both random and directed migration of human A2058 melanoma cells at picomolar concentrations. The activity of the ATX factor is completely sensitive to inhibition by pertussis toxin. No significant homology has been found to exist between the protein of the invention and any mammalian protein including previous factors known to stimulate cell motility.

There is a great clinical need to predict the aggressiveness of a patient's individual tumor, to predict the local recurrence of treated tumors and to identify patients at high risk for development of invasive tumors. The present invention provides a functional marker which is functionally related to the invasive potential of human cancer. The invention further provides an assay for this secreted marker in body fluids, or in tissues. The assay of the invention can be used in the detection, diagnosis, and treatment of human malignancies and other inflammatory, fibrotic, infectious or healing disorders.

SUMMARY OF THE INVENTION

The present invention relates, generally, to a motility stimulating protein and corresponding peptides thereof, and to a DNA segment encoding same. A human cDNA clone encoding a tumor cell motility-stimulating protein, herein referred to as autotaxin or "ATX", reveals that this protein is an ecto/exoenzyme with significant homology to the plasma cell membrane differentiation antigen PC-1. ATX is a 125 kDa glycoprotein, previously isolated from a human melanoma cell line (A2058), which elicits chemotactic and chemokinetic responses at picomolar to nanomolar concentrations.

It is a specific object of the present invention to provide autotaxin and peptide fragments thereof.

It is a further object of the present invention to provide a DNA segment that encodes autotaxin and a recombinant DNA molecule comprising same. It is a further object of the present invention to provide a cell that contains such a recombinant molecule and a method of producing autotaxin using that cell.

Another object of the present invention is the identification of a transmembrane domain of the human liver autotaxin protein and its apparent absence in tumorous forms of autotaxin. The tumorous form of autotaxin appears to be a secreted protein. The present invention relates to utilization of the different sites of localization for diagnosis and prognosis of the stages of tumor progression. Further, the invention relates to treatment methods, designed to advantageously block the secreted form of autotaxin activity while having little effect on the membrane-bound form of autotaxin.

Yet another object of the present invention relates to the identification of a highly variable region within the autotaxin gene, called a "hot spot". The variations in sequence apparently result in mutations, insertions, deletions and premature termination of translation. The present invention relates to manipulating this region so as to alter the activity of the protein. Further, the hot spot can serve as a marker in tumor diagnosis differentiating between different forms of the autotaxin protein.

It is yet another object of the present invention to provide a method of purifying autotaxin.

It is a further object of the present invention to provide cloned DNA segments encoding autotaxin and fragments thereof. The cDNA encoding the entire autotaxin protein contains 3251 base pairs, and has an mRNA size of approximately 3.3 kb. The full-length deduced amino acid sequence of autotaxin comprises a protein of 915 amino acids. Database analysis of the ATX sequence revealed a 45% amino acid identity (including 30 out of 33 cysteines) with PC-1, a pyrophosphatase/type I phosphodiesterase expressed on the surface of activated B cells and plasma cells. ATX, like PC-1, was found to hydrolyze the type I phosphodiesterase substrate p-nitrophenyl thymidine-5'monophosphate. Autotaxin now defines a novel motility-regulating function for this class of ecto/exo-enzymes.

Further objects and advantages of the present invention will be clear from the description that follows.

BRIEF DESCRIPTION OF THE DRAWINGS

FIG. 13. Schematic Diagram of autotaxin gene region.

For A2058: 4C11 is the original DNA clone obtained by screening an A2058 cDNA expression library in λgt11 with anti-peptide ATX-102. Upstream ATX peptide sequences were utilized for PCR amplification of A2058 mRNA, using the technique of reverse transcription/PRC. These peptides include ATX-101, ATX-103, and ATX-224. The approximate localization of each of peptide was obtained by matching the peptide with its homologous region on PC-1.

For N-tera 2D1, a λgt10 cDNA library was amplified and the cDNA inserts were isolated. PCR amplification, based on homologies with A2058 sequence, was utilized for DNA sequencing.

For normal human liver, a mRNA from liver was amplified with 5'RACE using primers from the known ATX-224 region of A2058 and N-tera 2D1.

Figure 14:
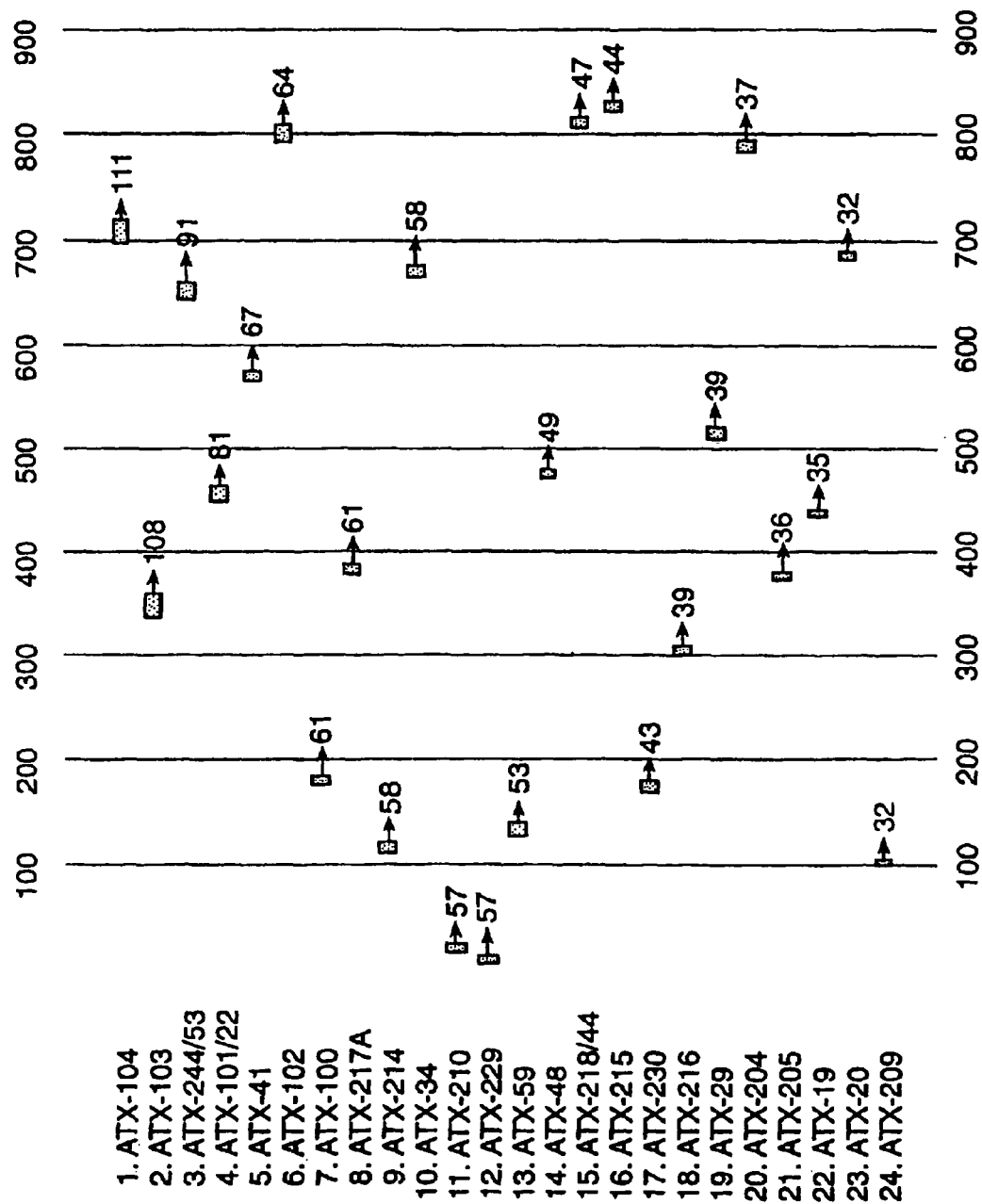

FIG. 14. Schematic match-up of ATX peptides with putative A2058 protein sequence.

Figure 15:
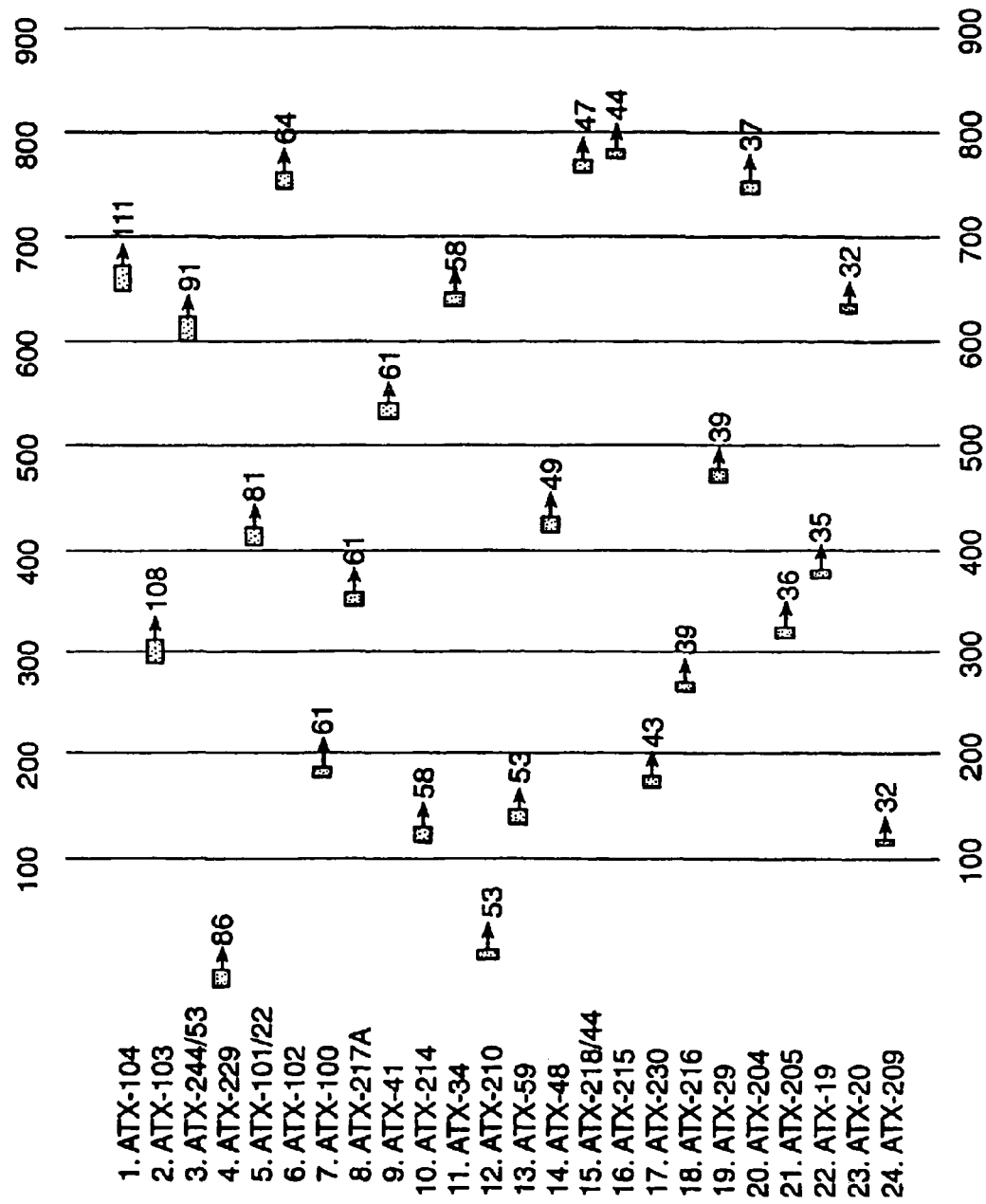

FIG. 15. Schematic match-up of ATX peptides with putative N-tera 2D1 protein sequence.

Figure 16:
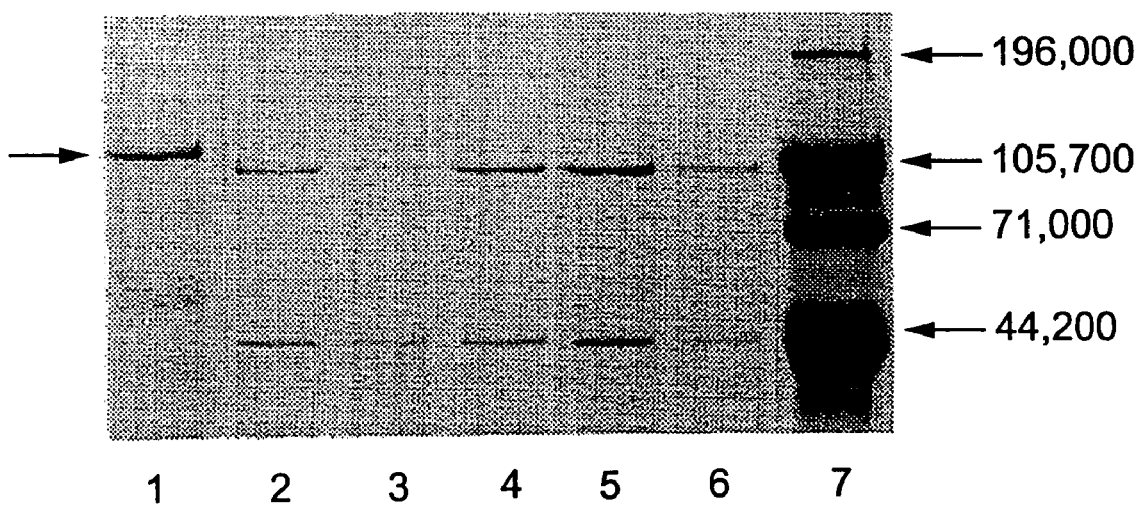

FIG. 16: ATX Treatment with PGNase F. Partially purified ATX was treated with 60 mU/ml PNGase F at 37° C. for 16 hr under increasingly denaturing conditions. The treated ATX samples were separated by SDS polyacrylamide gel electrophoresis run under reducing conditions and stained with Coomassie blue G-250. Lane 1 contains untreated ATX (arrow) with no enzyme added. Lane 2 contains the reaction mixture run under non-denaturing conditions (50 mM tris/10% ethylene glycol, pH 7). Lanes 3 and 4 have added 0.1 M β-mercaptoethanol and 0.5% Nonidet-P40, respectively. Lanes 5 and 6 contain the reaction mixtures in which the ATX sample was first boiled for 3 min in 0.1% SDS with (lane 6) or without (lane 5) 0.1 M β-mercaptoethanol, then had 0.5% Nonidet-P40 added to prevent enzyme denaturation. The enzyme can be detected as an ~44 kDa band in lanes 2-6.

Figure 17:
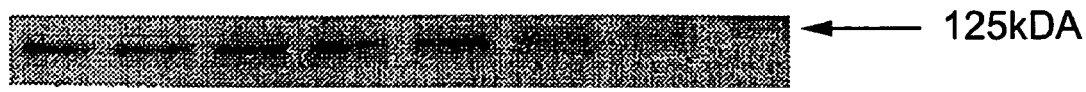
Figure 17B:
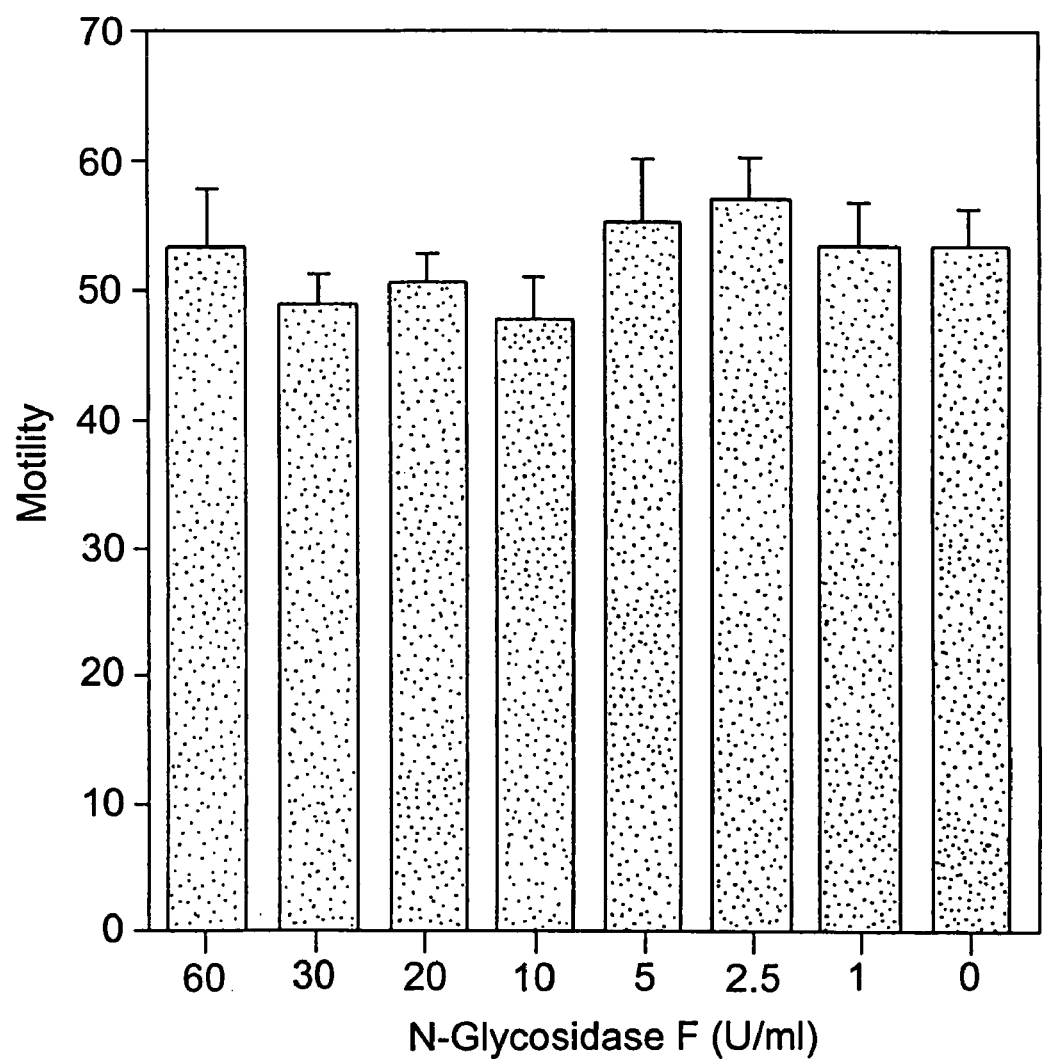

FIG. 17: Effect of varying concentrations of PNGase F on ATX molecular weight and motility-stimulating activity. Partially purified ATX was treated with various concentrations (range 0-60 mU/ml, shown on horizontal axis) of PNGase F at 37° C. for 16 hr. FIG. 17A shows the effect of the different treatments on ATX molecular weight. At concentrations of enzyme ≧30 mU/ml, the deglycosylation reaction appears to be complete. FIG. 17B shows the effect of the identical reaction mixtures on motility-stimulating capacity (immediately below the corresponding protein band of FIG. 17A). There is no significant difference between any of the treatment groups.

FIG. 18: Comparison of amino acid sequences of ATX and PC-1. The amino acid sequences of ATX (SEQ ID NO: 69) and PC-1 (SEQ ID NO: 70) are compared. Amino acid identity is indicated by a vertical line between the sequences. The location of the putative transmembrane/signal sequence is shown by a solid line. The two somatomedin B domains are identified by dashed lines. The putative phosphodiesterase active site is indicated by emboldened lines (residues 201 through 213 of SEQ ID NO: 69). The loop region of a single EF hand loop region is identified with double lines. The presumed cleavage site for each protein is indicated with arrows.

FIG. 19: Domain structure of ATX and PC-1. Putative domains are indicated for the two homologous proteins, ATX and PC-1.

DETAILED DESCRIPTION OF THE INVENTION

Tumor cell motility is a critical component of invasion and metastasis, but the regulation of this motility is still poorly understood. At least some tumor cells secrete autocrine motility factors (AMF's) that stimulate motility in the producing cells. Like the analogous autocrine growth factors, these AMF's allow tumor cells independence from the host in this important component of the metastatic cascade. One AMF, autotaxin (ATX), has recently been purified to homogeneity from the human melanoma cell line, A2058 (Stracke, et al., 1992). The purified protein was enzymatically digested and the peptide fragments were separated by reverse phase HPLC. A number of these peptides have been sequenced by standard Edman degradation (Table 6) from different purifications and different enzymatic digestion. Sequence information, obtained initially on 19 purified tryptic peptides, confirmed that the protein is unique with no significant homology to growth factors or previously described motility factors. These peptide sequences have now been used as the basis for identifying and sequencing the cDNA clone for ATX. The present invention comprises an amino acid sequence of ATX as well as a nucleic acid sequence coding for the ATX protein.

TABLE 6

PEPTIDE SEQUENCES FOR AUTOTAXIN.

| PEPTIDE NO. | AMINO ACID SEQUENCE | SEQ ID: NO: |
|---|---|---|
| ATX-18 | WHVAR | SEQ ID NO: 1 |
| ATX-19 | PLDVYK | SEQ ID NO: 2 |
| ATX-20 | YPAFK | SEQ ID NO: 3 |
| ATX-29 | PEEVTRPNYL | SEQ ID NO: 5 |
| ATX-34B | RVWNYFQR | SEQ ID NO: 38 |
| ATX-41 | HLLYGRPAVLY | SEQ ID NO: 29 |
| ATX-48 | VPPFENIELY | SEQ ID NO: 7 |
| ATX-59 | TFPNLYTFATGLY | SEQ ID NO: 32 |
| ATX-100 | GGQPLWITATK | SEQ ID NO: 8 |
| ATX-101/223A | VNSMQTVFVGYGPTFK | SEQ ID NO: 9 |
| ATX-102 | DIEHLTSLDFFR | SEQ ID NO: 10 |

TABLE 6-continued

PEPTIDE SEQUENCES FOR AUTOTAXIN.

| PEPTIDE NO. | AMINO ACID SEQUENCE | SEQ ID: NO: |
|---|---|---|
| ATX-103 | TEFLSNYLTNVDDITLVPETLGR | SEQ ID NO: 11 |
| ATX-104 | VNVISGPIDDYDYDGLHDTEDK | SEQ ID NO: 33 |
| ATX-204 | MHTARVRD | SEQ ID NO: 39 |
| ATX-205 | FSNNAKYD | SEQ ID NO: 40 |
| ATX-209 | VMPNIEK | SEQ ID NO: 41 |
| ATX-210 | TARGWECT | SEQ ID NO: 42 |
| ATX-212 | (N)DSPWT(N)ISGS | SEQ ID NO: 43 |
| ATX-214 | LRSCGTHSPYM | SEQ ID NO: 44 |
| ATX-215/34A | TYLHTYES | SEQ ID NO: 45 |
| ATX-213/217A | AIIANLTCKKPDQ | SEQ ID NO: 46 |
| ATX-216 | IVGQLMDG | SEQ ID NO: 47 |
| ATX-218/44 | TSRSYPEIL | SEQ ID NO: 48 |
| ATX-223B/24 | QAEVSSVPD | SEQ ID NO: 49 |
| ATX-224 | RCFELQEAGPPDDC | SEQ ID NO: 50 |
| ATX-229 | SYTSCCHDFDEL | SEQ ID NO: 51 |
| ATX-244/53 | QMSYGFLFPPYLSSSP | SEQ ID NO: 52 |

ATX is a glycosylated protein due to its high affinity for concanavalin A and amino acid sequence analysis of the ATX peptides. ATX has been demonstrated to be a 125 kDa glycoprotein whose molecular weight reduced to 100-105 kDa after deglycosylation with N-glycosidase F. The calculated molecular weight of the cloned protein is 100 kDa (secreted form) or 105 kDa (full length protein). Based on amino acid composition, the estimated pI is 9.0 which is higher than the pI determined by 2-D gel electrophoresis analysis (7.7-8.0) of purified ATX. This difference can be explained by the presence of sialic acid residues on the sugar moieties.

Autotaxin is secreted by A2058 human melanoma cells cultured in low abundance in serum-free conditioned medium. Autotaxin is a potent new cytokine with molecular mass 125 kDa which has been purified to homogeneity from the conditioned medium of the human melanoma cell line, A2058, utilizing sequential chromatographic methods as described herein. This new cytokine, termed autotaxin (ATX), is a basic glycoprotein with pI~7.8. ATX is active in the high picomolar to low nanomolar range, stimulating both chemotactic and chemokinetic responses in the ATX-producing A2058 cells as well as other tumor cells. This motile response is abolished by pretreatment of the cells with pertussis toxin. ATX may therefore act through a G protein-linked cell surface receptor. These characteristics distinguish ATX from several small growth factors and interleukins which are implicated in tumor cell motility (Stracke et al., 1988; Ruff et al., 1985; Maciag et al., 1984; Gospodarowicz, 1984; Van Snick, 1990; Yoshimura 1987).

The protein of the present invention, which in one embodiment is derived from A2058 human melanoma cells, can be prepared substantially free from proteins with which it is normally associated using, for example, the purification protocol disclosed herein. Alternatively, the protein of the present invention can be prepared substantially free from proteins, by cloning and expressing the cDNA encoding autotaxin as disclosed herein.

A large volume of serum-free conditioned medium from appropriate producer cells (e.g., tumor cells) is collected and concentrated approximately 500-fold. This concentrated conditioned medium is then separated from other contaminating proteins by techniques that rely on the chemical and physical characteristics of the protein. These include the molecular weight, relative hydrophobicity, net charge, isoelectric focusing point, and the presence of lectin-binding sugar residues on the protein.

Alternatively, the protein, or functional portion thereof, can be synthesized using chemical or recombinant means.

The protein of the present invention has a potent biological activity. Purified ATX is active in the picomolar range and 1 unit of activity corresponds to a concentration of approximately 500 pM as assessed by the cell motility assay described herein and elsewhere (Stracke et al., 1989).

The protein of the present invention has a molecular size, as determined by two dimensional gel electrophoresis, of from 120 to 130 kDa, or more specifically, about 125 kDa. Further, the protein of the present invention can have a pI in the range of 7.5 to 8.0, preferably, approximately 7.7. The present invention relates to autotaxin and peptides thereof having cell motility properties as described herein. These proteins and peptides thereof can be produced by isolation from a natural host or isolation as an expression product from a recombinant host.

The present invention also relates to a DNA segment coding for a polypeptide comprising an amino acid sequence corresponding to ATX, or a unique portion of such a sequence (unique portion being defined herein as at least 5, 10, 25, or 50 amino acids). In one embodiment, the DNA segment encodes any one of the amino acid sequences shown in SEQ ID NO: 1 to SEQ ID NO: 11 and SEQ ID NO: 26 to SEQ ID NO: 33. Another embodiment uses larger DNA fragments encoding amino acid sequences shown in SEQ ID NO: 34, SEQ ID NO: 36 and SEQ ID NO: 71. The entire coding region for autotaxin can also be used in the present invention shown in SEQ ID NO: 66 through SEQ ID NO: 69.

In another embodiment, the present invention relates to a recombinant DNA molecule comprising a vector (for example plasmid or viral vector) and a DNA segment coding for a polypeptide corresponding to ATX, as can be prepared by one skilled in the art. Preferably, the coding segment is present in the vector operably linked to a promoter. The present invention also relates to a recombinant protein produced from a host cell expressing a cDNA containing a coding region of ATX. Examples of ATX cDNAs from a variety of sources have been cloned and can be used for expression, including inter alia A2058 carcinoma cells, N-tera 2D1 cells and human liver.

In a further embodiment, the present invention relates to a cell containing the above-described recombinant DNA molecule. Suitable host cells include procaryotic cells (such as bacteria, including *E. coli*) and both lower eucaryotic cells (for example, yeast) and higher eucaryotic cells (for example, mammalian cells). Introduction of the recombinant molecule into the host cells can be effected using methods known in the art.

In another embodiment, the present invention relates to a method of producing a polypeptide having an amino acid sequence corresponding to ATX. The method comprises culturing the above-described cells under conditions such that the DNA segment is expressed, and isolating ATX thereby produced.

In a further embodiment, the present invention relates to an antibody having affinity for ATX or peptide fragments thereof. The invention also relates to binding fragments of such antibodies. In one preferred embodiment, the antibodies are specific for ATX peptides having an amino acid sequence set forth in one of SEQ ID NO:1 through SEQ ID NO:11 and SEQ ID NO:26 through SEQ ID NO:34, SEQ ID NO: 36 and SEQ ID NO:38 through SEQ ID NO:52. In addition, the antibodies may recognize an entire autotaxin protein.

Antibodies can be raised to autotaxin or its fragment peptides, either naturally-occurring or recombinantly produced, using methods known in the art.

The ATX protein and peptide fragments thereof described above can be joined to other materials, particularly polypeptides, as fused or covalently joined polypeptides to be used as carrier proteins. In particular, ATX fragments can be fused or covalently linked to a variety of carrier proteins, such as keyhole limpet hemocyanin, bovine serum albumin, tetanus toxoid, etc. See for example, Harper and Row, (1969); Landsteiner, (1962); and Williams et al., (1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., and references cited therein, and in particular in Kohler and Milstein (1975), which discusses one method of generating monoclonal antibodies.

In another embodiment, the present invention relates to an oligonucleotide probe synthesized according to the sense or antisense degenerative sequence set forth in one of SEQ ID NO:1 through SEQ ID NO:11, SEQ ID NO:26 through SEQ ID NO:33, SEQ ID NO:39 through SEQ ID NO:52, and SEQ ID NO:55 through SEQ ID NO:65.

Protein database searches of this sequence revealed a 45% amino acid identity with the plasma cell membrane marker protein, PC-1. ATX and PC-1 appear to share a number of domains, including two somatomedin B domains, the loop region of an EF hand, and the enzymatic site of type I phosphodiesterase/nucleotide pyrophosphatase. Like PC-1, ATX hydrolyzes p-nitrophenyl thymidine-5'-monophosphate, a type 1 phosphodiesterase substrate. This enzymatic function of ATX suggests a newly identified function for ecto/exo-enzymes in cellular motility.

In a further embodiment, the present invention relates to a method of diagnosing cancer metastasis and to a kit suitable for use in such a method. Preferably, antibodies to ATX can be used in, but not limited to, ELISA, RIA or immunoblots configurations to detect the presence of ATX in body fluids of patients (e.g. serum, urine, pleural effusions, etc.). These antibodies can also be used in immunostains of patient samples to detect the presence of ATX.

In yet another embodiment, the present invention relates to in vivo and in vitro diagnostics. ATX may be radiolabelled, by means known to one skilled in the art, and injected in cancer patients with appropriate ancillary substances also known to one skilled in the art, in order to ultimately detect distant metastatic sites by appropriate imagery. The level of ATX in tissue or body fluids can be used to predict disease outcomes and/or choice of therapy which may also include ATX inhibitors.

In a further embodiment, the present invention relates to a treatment of cancer. ATX antibodies can be cross-linked to toxins (e.g., Ricin A), by means known to one skilled in the art, wherein the cross-linked complex is administered to cancer patients with appropriate ancillary agents by means known to one skilled in the art, so that when the antibody complex binds to the cancer cell, the cell is killed by the cross-linked toxin.

In another embodiment, the different localizations of the normal versus tumorous forms of the ATX proteins within the tissue can be used as a tool for diagnosis and prognosis. The stage of disease progression can be monitored by elevated levels of ATX in the extracellular space as opposed to its normal cell membranes association. In addition, treatment methods for control of tumor progression can be designed to specifically block the activity of the secreted form of ATX. Such methods would have a preferential effect upon secreted ATX during tumor progression while not effecting normal ATX formation.

Yet another embodiment utilizes the hot spot located in the region from approximately nucleotides 1670 through 1815, as a marker gene for identification of tissues carrying a tumorous form of ATX.

The present invention is described in further detail in the following non-limiting examples.

EXAMPLES

The following protocols and experimental details are referenced in the Examples that follow:

Materials. The polycarbonate Nuclepore membranes and the 48-well microchemotaxis chambers were obtained from Neuro Probe, Inc. Pertussis toxin (PT), ethylene glycol (biotechnology grade), methyl α-D-mannopyranoside were obtained from commercial vendors. The ampholyte, pH 3-10 Bio-Lyte and pH 8-10 Bio-Lyte, were obtained from Bio-Rad. Phenyl Sepharose CL-4B; affi-Gel concanavalin A; ZORBAX BioSeries-WAX (weak anion exchange) column (9.4 mm×24 cm); Spherogel-TSK 4000SW, 3000SW and 2000SW columns (each 7.5 mm×30 cm); the Pro-Pac PA1 (4×50 mm) strong anion exchange column; the Aquapore RP300 C-8 reverse phase column (220×2.1 mm); and the AminoQuant C-18 reverse phase column (200×2.1 mm) were also obtained from commercial sources.

Affi-Gel 10 affinity resin was from Bio-Rad. The Gene-Amp PCR Reagent kit with AmpliTaq and the GeneAmp RNA PCR kit were purchased from Perkin-Elmer. The 5' RACE kit came from Gibco BRL Life Technologies, Inc. The p-nitrophenyl thymidine-5'monophosphate was obtained from Calbiochem Biochemicals.

Ethylene glycol (biotechnology grade) was from Fisher Biochemicals (Pittsburgh, Pa.). Peptide N-glycosidase F ("PNGase F"), O-glycosidase, neuraminidase (*Arthrobacter ureafaciens*), and swainsonine ("Swn") came from Boehringer-Mannheim (Indianapolis, Ind.). 1-Deoxymannojirimycin ("dMAN"), and N-methyl-1-deoxynojirimycin ("NMdNM") were from Oxford GlycoSystems, Inc. (Rosedale, N.Y.). Biotinylated concanavalin A, HRP-conjugated streptavidin, and HRP-conjugated goat anti-rabbit immunoglobulin were purchased from Pierce Chemicals (Rockford, Ill.). Polyvinyl pyrrolidone-free polycarbonate membranes and the microchemotaxis chamber were from NeuroProbe, Inc. (Cabin John, Md.).

Cell Culture. The human melanoma cell line A2058, originally isolated by Todaro (Todaro et al., 1980), was maintained as previously described by Liotta (Liotta et al., 1986). The N-tera 2 (D1 clone) was a kind gift from Dr. Maxine Singer, Laboratory of Biochemistry, National Cancer Institute, National Institutes of Health and was maintained as described (Andrews, P. W., Goodfellow, P. N. and Bronson, D. L. (1983) *Cell surface characteristics and other markers of differentiation of human teratocarcinoma cells in culture.*).

Production of Autotaxin. A2058 cells were grown up in T-150 flasks, trypsinized, and seeded into 24,000 cm$^2$ cell factories at a cell density of $1 \times 10^{10}$ cells/factory. After 5-6 days, the serum-containing medium was removed and the cells were washed with DPBS. The factories were maintained in DMEM without phenol red, supplemented with 4 mM glutamine, 100 units/ml penicillin, 100 μg/ml streptomycin, 5 μg/ml crystallized bovine serum albumin, 10 μg/ml bovine insulin, and 1 μM aprotinin. Culture supernatants were harvested every 3 days, frozen at −40° C. and replaced with fresh serum-free medium. Each cycle of supernatant was tested for ATX production with a cell motility assay detailed below. Typically, a cell factory continued to be productive for 9-11 of these cycles.

After accumulation of approximately 45-60 L of supernatant, the culture supernatants were thawed and concentrated down to 2-2.5 L using an Amicon S10Y30 spiral membrane ultrafiltration cartridge. This supernatant was further concentrated in an Amicon high performance ultrafiltration cell using Diaflo membranes. The final volume achieved from 100-200 L of conditioned medium was typically 250-400 ml. All ultrafiltrations were performed at 4° C.

Cell Motility Assays. Purification of autotaxin was monitored by testing the motility-stimulating capacity of the fractions collected from the columns. These fractions were in buffers unsuitable for a chemotaxis assay so each fraction had to be washed into an appropriate buffer, i.e., 0.1% (w/v) BSA in DPBS containing calcium and magnesium. This dialysis was performed by adding aliquots of each fraction to be tested into Centricon-30™ ultrafiltration tubes, which retain molecular species larger than 30,000 daltons.

The assay to determine motility was performed in triplicate using a 48-well microchemotaxis chamber as described elsewhere in detail (Stracke et al., 1987; Stracke, et al., 1989). The Nuclepore™ membranes used in these modified Boyden chambers were fixed and stained with Diff-Quik.™ Chemotaxis was quantitated either by reading the stained membranes with a 2202 Ultroscan laser densitometer or by counting 5 randomly chosen high power fields (HPF) under light microscopy (400×) for each replicate. Densitometer units (wavelength—633 nm) have been shown to be linearly related to the number of cells per HPF (Taraboletti, 1987; Stracke, et al., 1989). Typically, unstimulated motility (background) corresponded to 5-10 cells/HPF and highly responding cells to 70-100 cells/HPF above unstimulated background (i.e., 75-110 total cells/HPF).

For experiments using PT, the toxin was pre-incubated with the cells for 1-2 hr. at room temperature prior to the assay and maintained with the cells throughout the assay (Stracke, et al., 1987). The treated cells were tested for their motility response to the chemoattractant as well as for unstimulated random motility.

Purification of Autotaxin. Ammonium sulfate, to a final concentration of 1.2 M, was added to the concentrated A2058 conditioned medium for 1 hr. at 4° C. The solution was spun in a RC2-B Ultraspeed Sorvall centrifuge at 10,000×g for 15 min. Only the supernatant had the capacity to stimulate motility.

In the first step, the sample was fractionated by hydrophobic interaction chromatography using 200 ml phenyl Sepharose CL-4B column equilibrated into 50 mM Tris (pH 7.5), 5% (v/v) methanol and 1.2 M ammonium sulfate. The supernatant from the ammonium sulfate fractionation was added to this column and eluted using linear gradients of 50 mM Tris (pH 7.5), 5% (v/v) methanol, with decreasing (1.2-0.0) M ammonium sulfate and increasing (0-50) % (v/v) ethylene glycol at 1 ml/min.

The active peak was pooled, dialyzed into 50 mM Tris, 0.1 M NaCl, 0.01 M $CaCl_2$, 20% (v/v) ethylene glycol, and subjected to a second fractionation by lectin affinity chromatography using a 40 ml Affi-Gel concanavalin A column run at 1 ml/min. The sample was eluted in a stepwise fashion in the same buffer with 0, 10, and 500 mM methyl α-mannopyranoside added successively. Fractions from each step of the gradient were pooled and tested for their capacity to stimulate motility.

In the third purification step, the sample that eluted at 500 mM α-methyl-mannopyranoside was dialyzed into 10 mM Tris (pH 7.5) with 30% (v/v) ethylene glycol and fractionated by weak anion exchange chromatography. Chromatography was carried out on a ZORBAX BioSeries-WAX column using a Shimadzu BioLiquid chromatograph and eluted with a linear gradient of (0.0-0.4 M) sodium chloride at 3 ml/min.

The active peak was pooled, dialyzed against 0.1 M sodium phosphate (pH 7.2), 10% (v/v) methanol, and 10% (v/v) ethylene glycol, and subjected to a fourth fractionation step on a series of Spherigel TSK columns (4000SW, 4000SW, 3000SW, 2000SW, in that order). This molecular sieve step was run using the Shimadzu BioLiquid chromatograph at 0.4 ml/min.

The active peak was pooled and dialyzed into 10 mM Tris (pH 7.5), 5% (v/v) methanol, 20% (v/v) ethylene glycol and subjected to a fifth (strong anion exchange) chromatography step, a Pro-Pac PA1 column run at 1 ml/min using a Dionex BioLC with AI450 software. The sample was eluted with a linear gradient of (0.0-0.4M) NaCl.

In order to calculate activity yields after each step of purification, a unit of activity had to be derived. The dilution curve of ATX was biphasic with a broad peak and a linear range at sub-optimal concentrations. One unit of activity/well (i.e., 40 units/ml) was defined as 50% of the maximal activity in a full dilution curve. This allowed calculation of the activity contained in any volume from the dilution needed to achieve 1 unit/well. Therefore, if a 1:10 dilution were needed in order to produce 1 unit of activity/well, the material contained 10×40=400 units/ml.

Gel Electrophoresis. Protein samples were analyzed by SDS-polyacrylamide gel electrophoresis using the conditions of Laemmli (Laemmli, 1970). In brief, 7 or 8% SDS-containing polyacrylamide gels were prepared or pre-poured (8-16%) gradient gels were obtained commercially. Samples were prepared with or without reducing conditions (5% β-mercaptoethanol). After electrophoretic separation, the gels were stained using Coomassie Blue G-250 as previously described (Neuhoff, et al., 1988). In this staining protocol, which ordinarily requires no destaining step, the Coomassie stain appears to be able to stain as little as 10 ng of protein.

For two-dimensional electrophoresis, the protein, in 20% ethylene glycol, was dried in a Speed-vac and redissolved in loading solution: 9M urea, 1% (v/v) pH 3-10 Bio-Lyte, and 2.5% (v/v) Nonidet-P40. This sample was then subjected to isoelectric focusing (O'Farrell, 1975) using a Bio-Rad tube cell in 120×3 mm polyacrylamide tube gels containing 9M urea, 2% (v/v) pH 3-10 Bio-Lyte, 0.25% (v/v) pH 8-10 Bio-Lyte and 2.5% (v/v) Nonidet-P40. Reservoir solutions were 0.01 M phosphoric acid and 0.02 M NaOH. Non-equilibrium isoelectric focusing (O'Farrell, et al., 1977) was run initially with constant voltage (500 v) for 5 hr. Since the protein was basic, the procedure was repeated under equilibrium conditions (500 v for 17 hr.). Electrophoresis in the second dimension was performed on a 7.5% polyacrylamide using the conditions of Laemmli (1970). The gel was stained with Coomassie Blue G-250 as above.

Preparation of peptides for internal sequence of autotaxin. Homogeneous ATX was sequentially digested with cyanogen bromide and, following reduction and pyridylethylation, with trypsin (Stone, et al., 1989). The resulting fragments were then separated by gradient elution on an Aquapore RP300 C-8 reverse phase column: 0.1% (v/v) trifluoroacetic acid and (0-70)% acetonitrile over 85 min. at a flow rate of 0.2 ml/min. A Dionex AI450 BioLC system was utilized and fractions were collected manually while monitoring the absorbance at 215 nm.

Sequence analysis of peptides. The amino acid sequences of peptides resulting from digestion and purification of ATX peptides #1-7 and 12-18, corresponding to SEQ ID NO:1 through SEQ ID NO:7 and SEQ ID NO:26 through SEQ ID NO:32, respectively, were determined on a Porton Instruments 2020 off-line sequenator using standard program #1. Phenylthiohydantoin amino acid analysis of sequenator runs were performed on a Beckman System Gold HPLC using a modified sodium acetate gradient program and a Hewlett-Packard C-18 column. ATX-100 (SEQ ID NO:8), ATX-101 (SEQ ID NO:9), ATX-102 (SEQ ID NO:10), ATX-103 (SEQ ID NO:11) and ATX 104 (SEQ ID NO:33) were sequenced from gel-purified ATX.

Protein databases (Pearson, et al. 1988) that were searched for homologies in amino acid sequence with the ATX peptides include: GenBank (68.0), EMBL (27.0), SWISS-PROT (18.0), and GenPept (64.3).

Example 1

Purification of Autotaxin

The A2058 cells had been previously shown to produce protein factors which stimulate motility in an autocrine fashion (Liotta, et al., 1986). Conditioned medium from these cells was therefore used to identify and purify a new motility-stimulating factor, which is here named autotaxin and referred to as ATX. Since the purification was monitored with a biological assay, motility-stimulating activity had to be maintained throughout. The activity proved to be labile to freezing, acidic buffers, proteases (but not DNase or RNase), reduction, strong chaotrophic agents (e.g. >4 M urea), and a variety of organic solvents (isopropanol, ethanol, acetonitrile). An organic solvent, ethylene glycol, which did not decrease bioactivity, was added for both storage and chromatographic separation.

100-200 L of serum-free conditioned medium were required in order to produce enough ATX for amino acid sequence analysis. The medium contained low concentrations of both BSA (5 µg/ml) which was needed as a carrier protein and insulin (10 µg/ml) which was required to support cell growth in low protein medium. Ultrafiltration to concentrate this large volume was performed with low protein-binding YM30 membranes which retain molecular species with $M_r > 30,000$. As seen in Table 1, 200 L of conditioned medium prepared in this manner resulted in $10 \times 10^6$ units of activity. However, the initial unfractionated conditioned medium contained additional substances known to stimulate activity, particularly insulin, which does not completely wash out in the ultrafiltration step and which is additive to the motility stimulating activity in a complex manner (Stracke, et al., 1989). This had to be taken into account in order to determine yields for subsequent steps in which insulin had been removed.

TABLE 1

PURIFICATION OF AUTOTAXIN

| Purification Step Recovery | Protein (mg) | Activity[a] (total units) | Specific Activity (units/mg) | (%)[b] |
|---|---|---|---|---|
| 200 L Conditioned Medium | 33,000 | 10,000,000[c] | 300 | |
| Phenyl Sepharose | 1,235 | 460,000 | 370 | 100 |
| Concanavalin A | 58 | 660,000 | 11,400 | 100 |
| Weak Anion Exchange | 4.5 | 490,000 | 110,000 | 100 |
| TSK Molecular Sieves | ~0.4[d] | 220,000 | 550,000 | 48 |
| Strong Anion Exchange | ~0.04[d] | 24,000[e] | 600,000 | 5.2 |

[a] Activity calculated from Boyden chamber assay. The dilution which resulted in 50% of maximal activity (generally approximately 20 laser density units or ~40 cells/HPF) was chosen to have 1 unit of activity per well (equivalent to 40 units/ml).
[b] Recovery was estimated from activity, after the first purification column (i.e., phenyl sepharose).
[c] Initial activity in the unfractionated conditioned medium reflected the fact that insulin was used in the medium as a necessary growth factor under low protein conditions.
[d] Estimated protein is based on quantification by amino acid analysis.
[e] This specific activity for purified protein corresponds to ~10 fmol ATX/unit of motility activity (in a Boyden chamber well).

Figure 1:
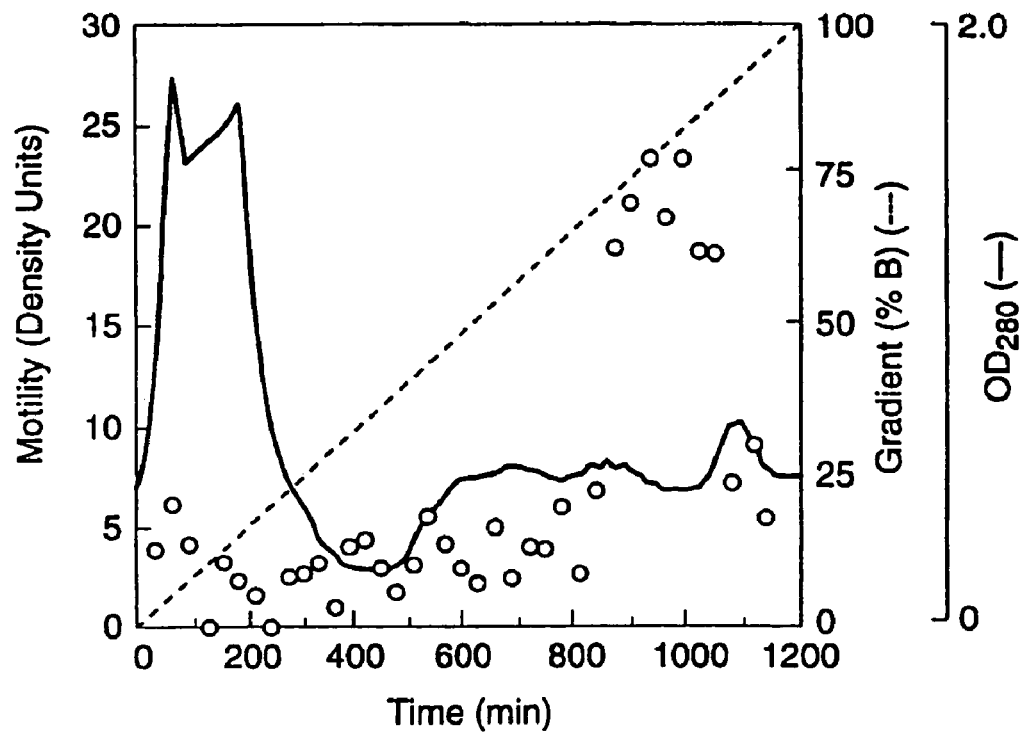
FIG. 1. Fractionation of ATX by hydrophobic interaction. A 200 ml sample of A2058 conditioned media was chromatographed on a 200 mL column of phenyl Sepharose-4B. Buffer A was 50 mM Tris (pH 7.5), 5% methanol, and 1.2 M ammonium sulfate. Buffer B was 50 mM Tris (pH 7.5), 5% methanol and 50% ethylene glycol. The gradient (----) represents a double linear gradient with decreasing ammonium sulfate (1.2 to 0.0 M) and increasing ethylene glycol (0 to 50%). Absorbance was monitored at 280 nm (——) and indicated that most of the protein did not bind to the column. Ten ml fractions were assayed for motility stimulating capacity using the Boyden Chamber assay (o). The peak of motility activity occurred between 900 and 1050 minutes, —12% of the gradient.

The first step in the purification involved fractionation by hydrophobic interaction chromatography using a phenyl Sepharose CL-4B column. The results are shown in FIG. 1. Most proteins, including insulin, eluted from the column in early fractions or in the void. However, the peak of activity eluted relatively late. The activity which was purified was estimated as 460,000 units±20% (Table 1). As the pooled peak of activity from the phenyl Sepharose fractionation is considered to be the first sample without significant insulin contamination, subsequent yields are measured against its total activity. Gel electrophoresis of a small portion of the pooled peak of activity (FIG. 6A, column 2) revealed a large number of protein bands with BSA predominant from the original conditioned medium.

Figure 2:
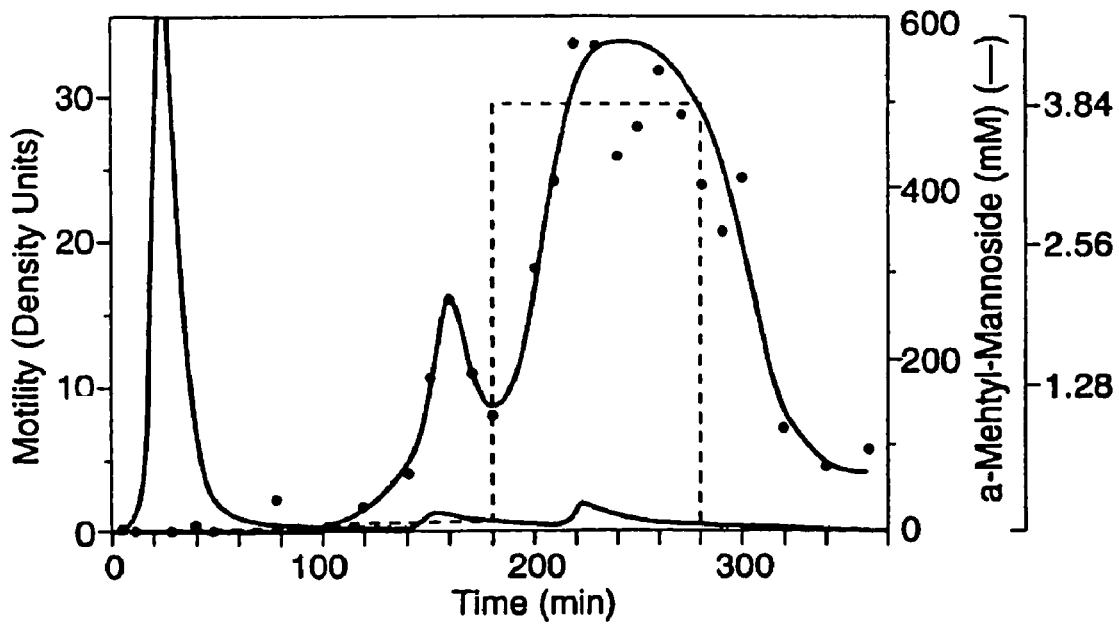
FIG. 2. Isolation of ATX by lectin affinity chromatography. 20 ml portions of the phenyl Sepharose activity peak were affinity purified on a 40 ml Concanavalin A Affi-Gel column. The bound components were eluted with a step gradient (----) of methyl α-D-mannopyranoside (0.0 mM, 10 mM, and 500 mM) in a buffer consisting of 0.05 M Tris (pH 7.5), 0.1 M NaCl, 0.01 M $CaCl_2$ and 20% ethylene glycol. Absorbance was monitored at 280 nm (_____) and indicated that the majority of the protein components did not bind to the column. Motility was assayed in 10 mL fractions ( . . . o . . . ) and was found predominantly in the 500 mM elution concentration. One of seven chromatographic runs is shown.

In the second step of purification, the active peak was applied to the lectin affinity column, Affi-Gel concanavalin A. As shown in FIG. 2, most protein (estimated to be 90% of the total absorbance at 280 nm) failed to bind to the column at all. The non-binding fraction contained essentially no motility-stimulating activity (see dotted line in FIG. 2). When a linear gradient of methyl α-D-mannopyranoside was applied to the column, chemotactic activity eluted off in a prolonged zone, beginning at a concentration of approximately 20 mM sugar. Consequently, a step gradient was used to elute. Pure BSA failed to bind to con A.

Activity was found primarily in the 500 mM step of methyl α-D-mannopyranoside. There appeared to be no significant loss of activity as seen in Table 1; however, specific activity (activity/mg total protein) increased thirty-fold. Gel electrophoresis of the pooled and concentrated peak (FIG. 6A, column 3) revealed that the BSA overload was no longer apparent and the number of bands were much reduced. When the unbound protein was concentrated and applied to a gel, it appeared identical to the active peak from phenyl Sepharose-4B with a large BSA band.

Figure 3:
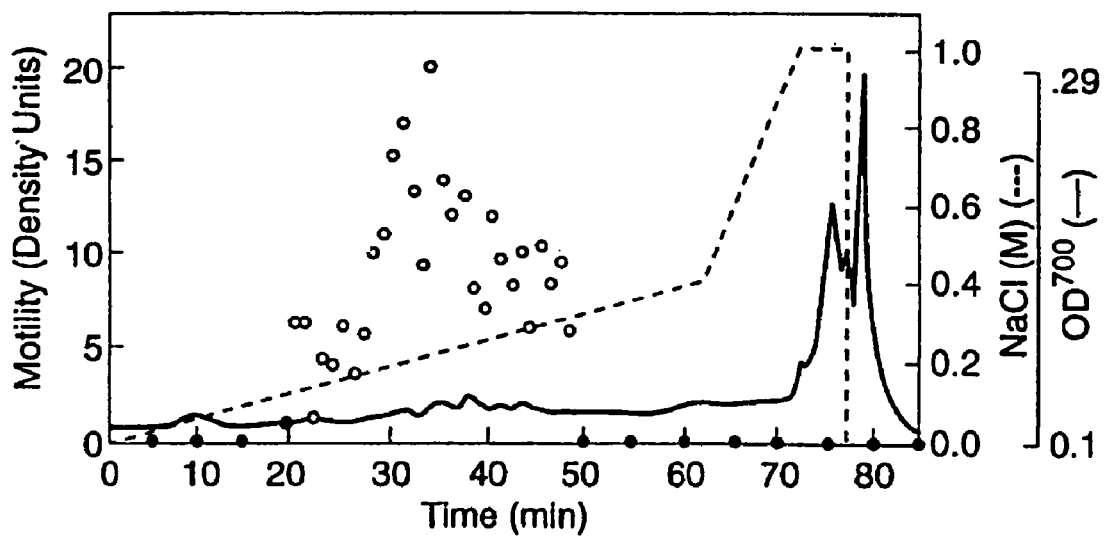
FIG. 3. Purification of ATX by weak anionic exchange chromatography. Approximately 30% of the activity peak eluted from the Con A affinity column was applied to a ZORBAX BioSeries-WAX column. The bound components were eluted with an NaCl gradient (----) in a buffer consisting of 10 mM Tris (pH 7.5) and 30% ethylene glycol. Motility (o) was assayed in 1.0 ml fractions. The peak of activity eluted in a discrete but broad region in the shallow portion of the gradient. Absorbance was monitored at 230 nm (_____). The majority of the protein components not associated with activity bound strongly to the column were eluted at 1.0 M NaCl. One of two chromatographic runs is shown.
Figure 6A:
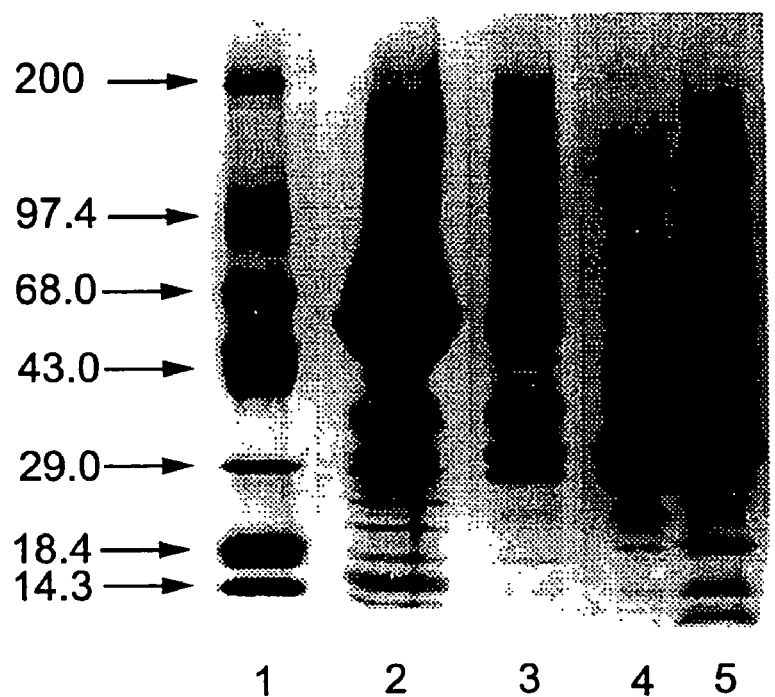
FIGS. 6A, 6B and 6C. Protein components associated with the activity peaks from various stages of purification. The activity peak from each chromatographic fractionation was pooled, concentrated and analyzed by SDS-polyacrylamide gel electrophoresis. Molecular weight standards are in Lane 1 for each panel. Panel 6A) 8-16% gradient gel of the first three purification steps, run under non-reducing conditions. Lane 2 is an aliquot of the pooled activity peak eluted from the phenyl sepharose fractionation. Lane 3 is an aliquot of the pooled activity peak eluted from the Con A affinity purification. Lanes 4 and 5 show the "peak" and "shoulder" of activity fractionated by weak anion exchange chromatography (FIG. 3). Panel 6B) 7% gel of the activity peak fractionated by molecular sieve exclusion chromatography. Lanes 2 and 3 show the protein separation pattern of the total pooled activity peak when the gel was run under non-reducing and reducing conditions, respectively. Panel 6C) 8-16% gradient gel of the final strong anionic exchange chromatographic separation, run under non-reducing conditions. Lane 2 comprises—1% of the total pooled activity peak eluted from the column.

The third purification step involved fractionating the previous active peak by weak anion exchange chromatography as shown in FIG. 3. Under the running conditions, activity eluted in a broad peak-shoulder or double peak in the middle of the shallow portion (0.0-0.4 M) of the NaCl gradient. The largest proportion of protein, lacking in motility-stimulating capacity, bound strongly to the column and eluted off in high salt (1 M NaCl). There appeared to be no significant loss of activity, though specific activity increased by twenty-fold (Table 1). Analysis by gel electrophoresis of both the peak (28-34 min. in FIG. 3) and the shoulder (35-45 min. in FIG. 3)

is shown in FIG. 6A (columns 4 and 5, respectively). Two predominant protein bands resulted: a broad doublet around 25-35 kDa and a second doublet around 110-130 kDa.

Figure 4:
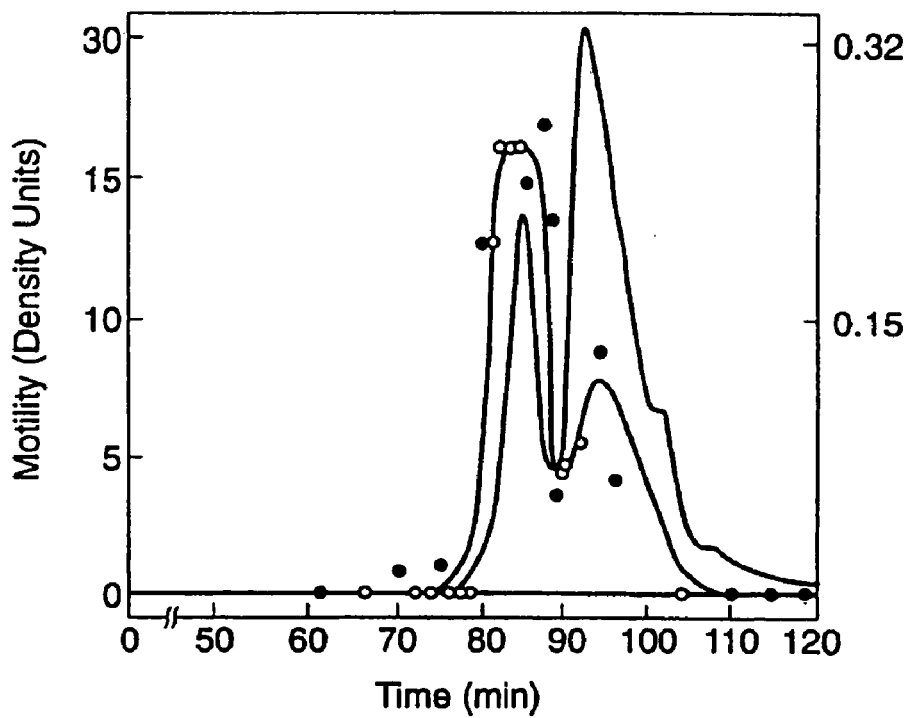
FIG. 4. Purification of ATX by molecular sieve exclusion chromatography. The entire activity peak eluted from the weak anion exchange column was applied to a series of TSK columns (4000SW, 4000SW, 3000SW, and 2000SW, in this order). Proteins were eluted in a buffer consisting of 0.1M $NaPO_4$ (pH 7.2) with 10% methanol and 10% ethylene glycol. Two major protein peaks were evident by monitoring the absorbance at 235 nm (_____). Motility ( . . . o . . . ) was assayed in 0.4 ml samples and found predominantly in the first, smaller, protein peak.
Figure 6B:
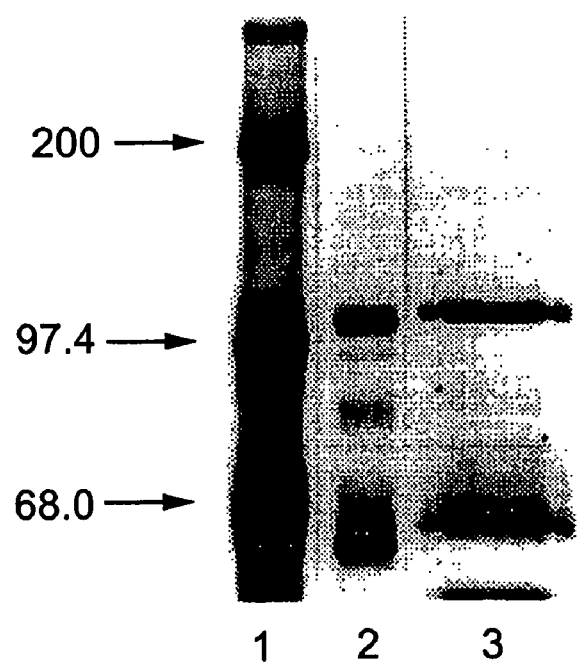

In the fourth purification step, the active peak was applied to a series of molecular sieves. Spectrophotometric monitoring of the eluant revealed two large peaks of protein (FIG. 4). Activity corresponded to the first, higher molecular weight peak. Recovery of activity was ~48% with a five-fold increase in specific activity. Analysis by gel electrophoresis was performed under non-reducing and reducing conditions as shown in FIG. 6B (columns 2 and 3, respectively). This fractionation step had essentially removed all contaminating protein of molecular weight <55 kDa. The predominant band remaining has a molecular weight of 120 kDa unreduced and 125 kDa reduced; there are two minor bands with molecular weights 85 kDa and 60 kDa. The fact that the 120 kDa protein changes so little in electrophoretic mobility after-reduction would tend to indicate a paucity of disulfide bonds. However, the existing disulfide bonds have functional significance because motility-stimulating activity is labile to reduction.

Figure 5:
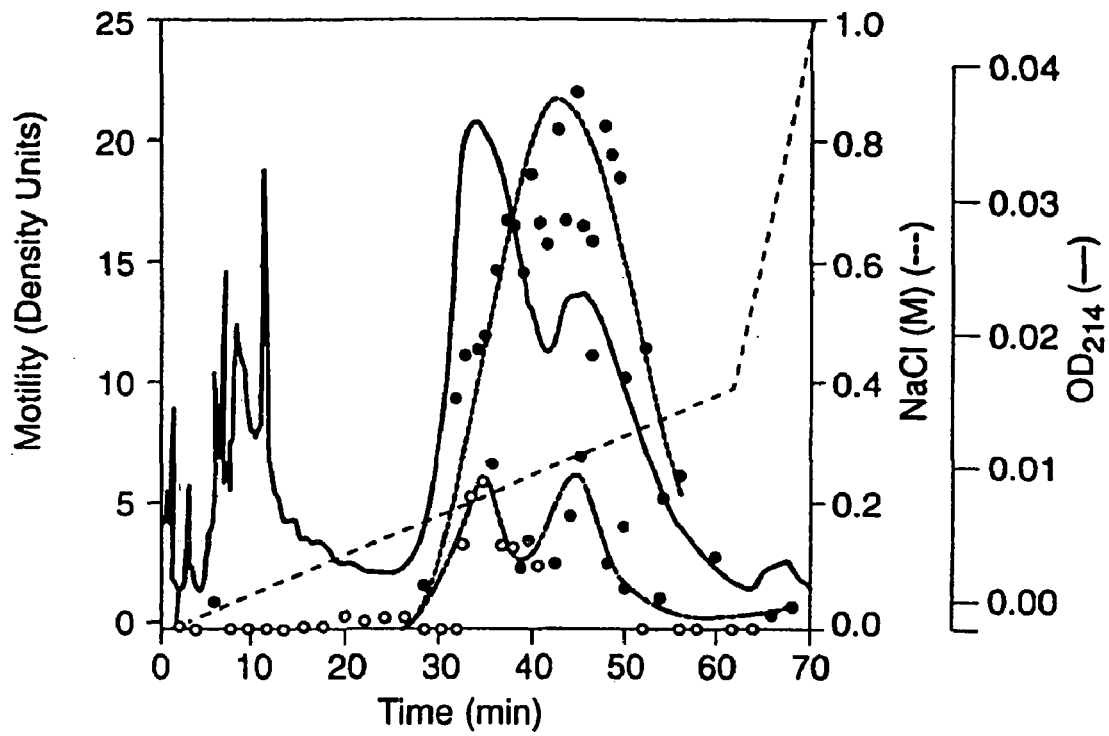
FIG. 5. Final purification of ATX by strong anionic exchange chromatography. Approximately 15% of the activity peak from the molecular sieve exclusion series was applied to a Pro-Pac PA1 column. Protein which bound to the column was eluted with a NaCl gradient (----) in a buffer consisting of 10 mM Tris (pH 7.5), 5% methanol and 20% ethylene glycol. Absorbance was monitored at 215 nM (_____). Motility activity was assayed in 1.0 ml fractions at two different dilutions: ⅕ ( . . . o . . . ) or ¹⁄₁₅ (._____.o._____.). Activity was found to correspond to a double protein peak in the central region of the gradient.
Figure 6C:
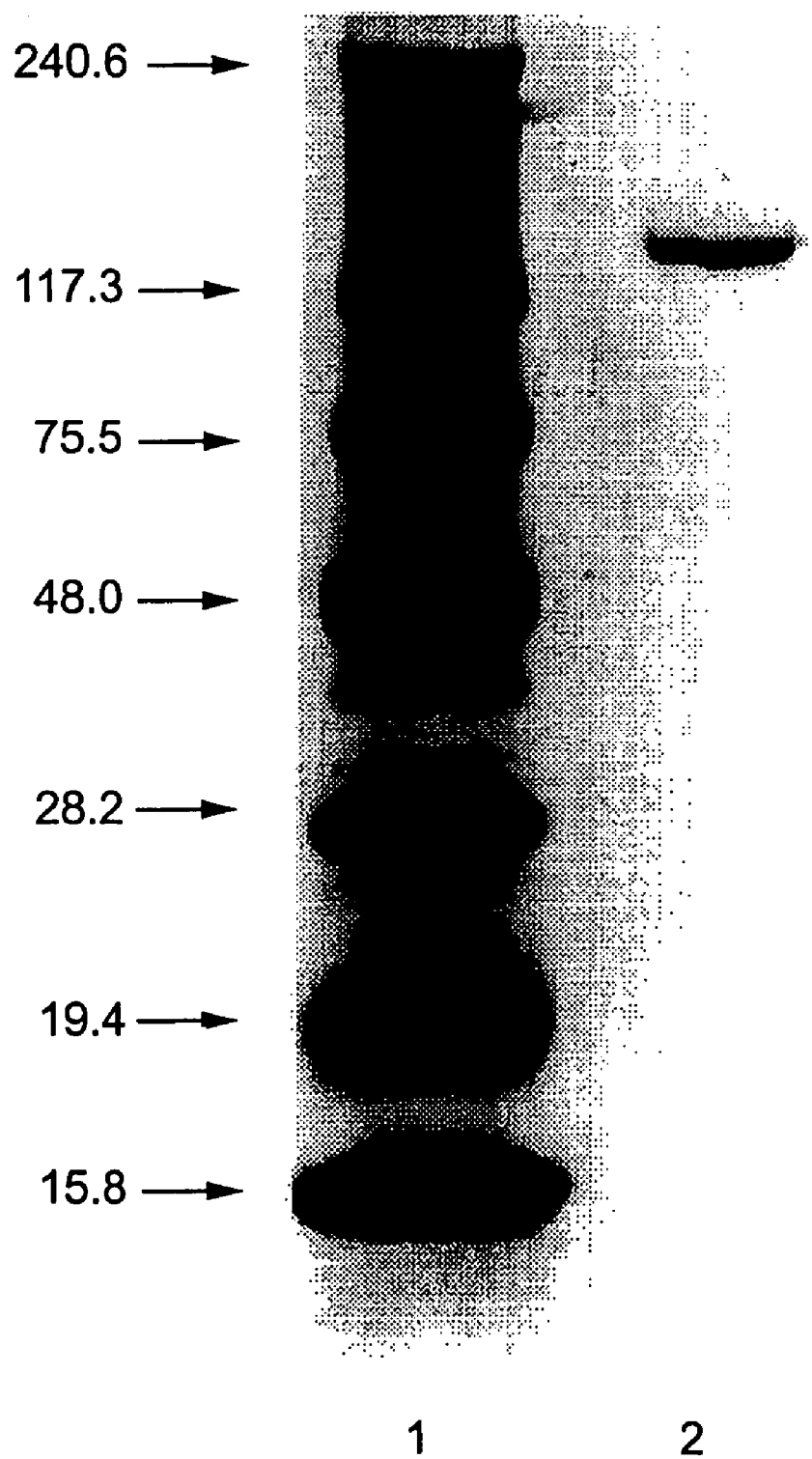

The fifth purification step involved fractionation of the active peak by strong anion exchange chromatography. As shown in FIG. 5, activity corresponds to two broad optical absorbance peaks in the middle of the gradient with contaminating proteins eluting earlier. These two peaks were identical by amino acid analysis and by polyacrylamide gel electrophoretic separation. They presumably represent different glycosylation states of the same parent protein. Activity is shown in FIG. 5 at two different sample dilutions. Several dilutions of the fractionated samples were often necessary in order to resolve the true "peak" of activity as the shape of the ATX dilution curve was not sharp due to saturation and down regulation at high concentrations. Recovery from this chromatographic step is lower (5% compared to phenyl Sepharose), as might be expected when a minute quantity of protein is applied to a column; however, specific activity again increased (Table 1). Analysis by gel electrophoresis revealed a single protein band at molecular weight 120 kDa, unreduced (FIG. 6C, column 2).

Example 2

Characterization of Autotaxin

Figure 7:
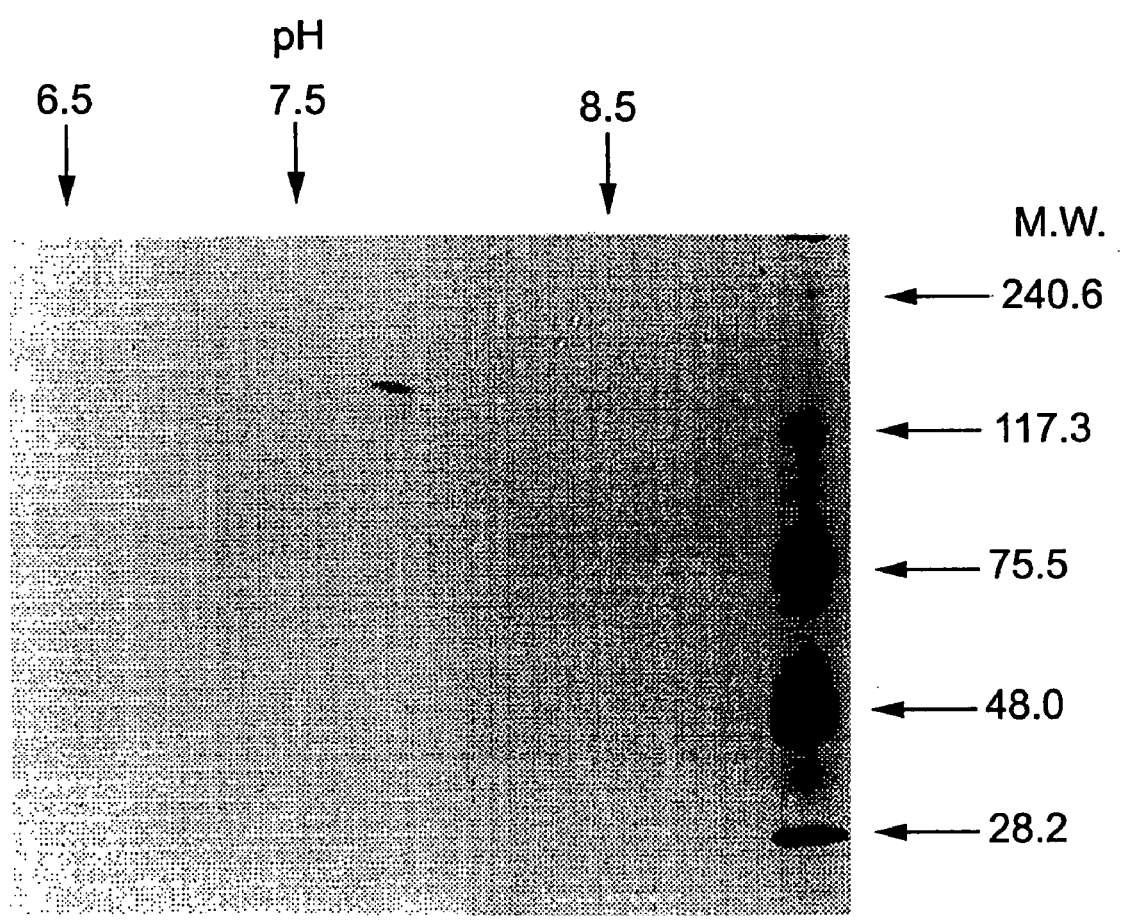
FIG. 7. Two-dimensional gel electrophoresis of ATX. Purified ATX (FIG. 6, Panel C) was subjected to non-equilibrium isoelectric focusing (5 hr. at 500v), then applied to a 7.5% SDS-polyacrylamide gel for the second dimension. The pH separation which resulted was measured in 0.5 cm samples of concurrently run tube gels and is shown at the top. Molecular weight standards for the second dimension are shown on the right. This analysis reveals a single component with pI=7.7±0.2 and $M_r$=120,000.

Two dimensional gel electrophoresis of the purified protein (FIG. 7) revealed a single predominant band. The band slopes downward slightly toward the basic side of the gel in a manner that is characteristic of glycosylated proteins. A basic pI of 7.7±0.2 was essentially the same whether the isoelectric focusing was run under non-equilibrium conditions (5 hr.) or was allowed to go to equilibrium (17 hr.).

Figure 8:
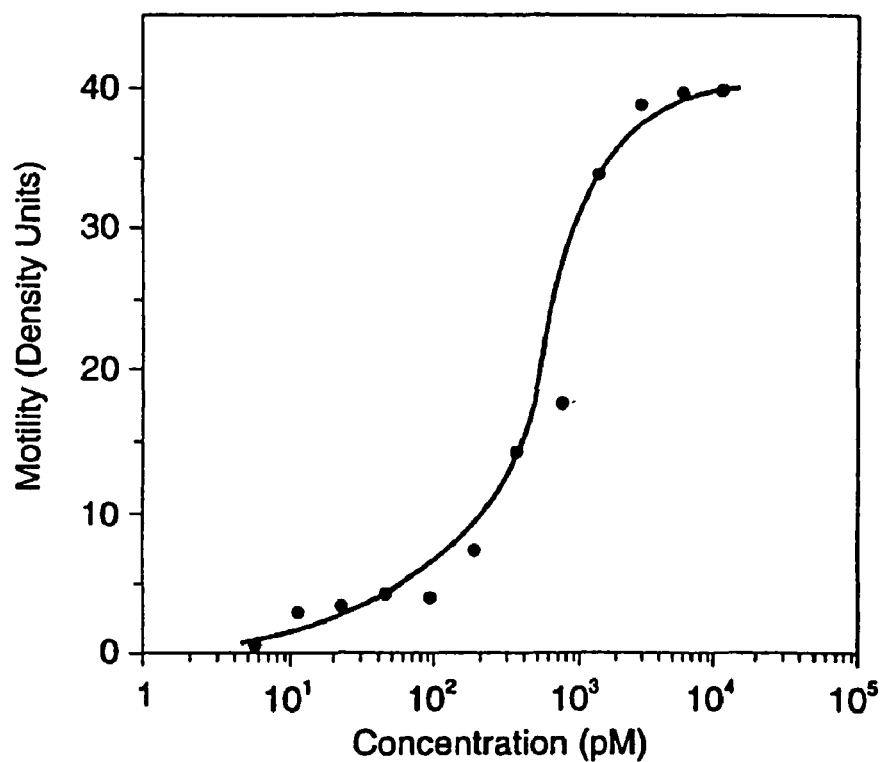
FIG. 8. Dilution curve of ATX. Purified ATX (FIG. 6, Panel C) was serially diluted and tested for motility-stimulating activity. The result, with unstimulated background motility subtracted out, shows that activity is half-maximal at ~500 pM ATX.
Figure 9:
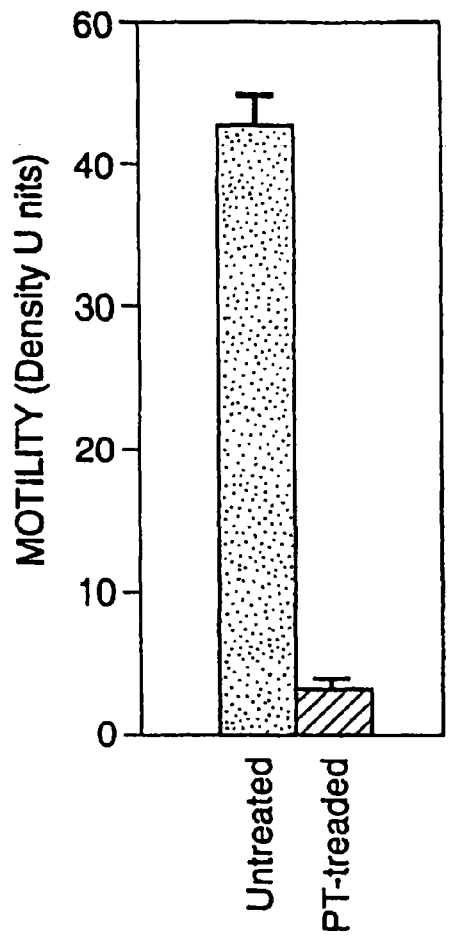
FIG. 9. Pertussis toxin (PT) sensitivity of ATX. A2058 cells were pre-treated for 1 hr. prior to the start of the motility assay with 0.5 μg/ml PT in 0.1% BSA-DMEM or with 0.1% BSA-DMEM alone (for untreated control). The motility activity stimulated by purified ATX (FIG. 6, Panel C) was then assessed for the two treatment groups. The result, expressed as cells/HPF±S.E.M. with unstimulated background motility subtracted out, reveals profound inhibition of PT-treated cells (hatched) compared to untreated cells (solid). PT had no effect on cell viability. S.E.M.'s were <10%.

A dilution curve of the purified protein is shown in FIG. 8. The protein is active in the picomolar range and 1 unit of activity appears to correspond to a concentration of 400-600 picomolar (or approximately 10 fmol of ATX/Boyden chamber well). When dilutions were begun at higher concentrations of ATX, the resultant curve showed a broad plateau with down-regulation at the highest concentrations. The motility response to purified autotaxin is highly sensitive to pertussis toxin (hereinafter referred to as "PT") (Table 2 and FIG. 9) with approximately 95% inhibition of activity at 0.5 μg/ml PT.

TABLE 2

Effect of Pertussis Toxin (PT) on Autotaxin-stimulated motility
A2058 Motility Response
(density units[1])

|  | control cells[2] | Pertussis toxin-treated cells[3] |
|---|---|---|
| Condition medium[4] | 60.3 | 0.4 |
| Purified Autotaxin | 38.5 | 0.0 |

[1]Chemotaxis quantitated by motility assay (Stracke, et al., 1978).
[2]A2058 cell suspended at 2 × 10⁶ cells/ml in DMEM supplemented with 1 mg/ml bovine serum and rocked at room temperature for 1 hr.
[3]As control with 0.5 μg/ml pertussis toxin.
[4]Prepared by adding DMEM without phenol red supplemented with 0.1 mg/ml bovine serum albumin to subconfluent flasks of A2058 cells. The medium was harvested after 2 days incubation at 37° C. in a humidified atmosphere and concentrated 25-30 fold using an Amicon ultrafiltration assembly with a YM-30 membrane.

Figure 10:
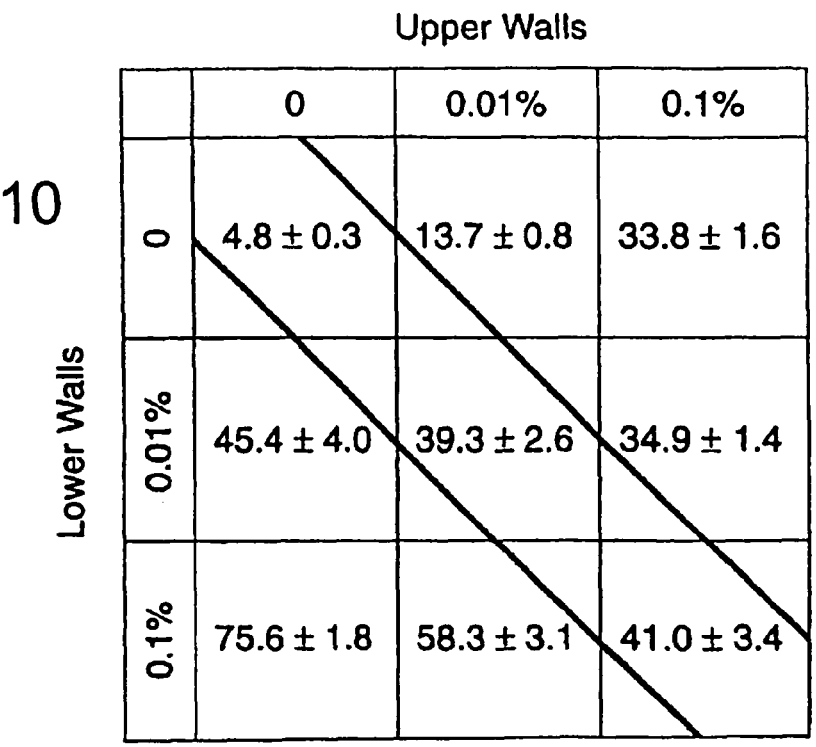
FIG. 10. Checkerboard analysis of ATX-stimulated motility. Varying dilutions of autotaxin were added to the upper chamber with the cells and/or to the lower chamber, as shown. Motility response, expressed as cells/HPF±S.E.M., was assessed for each point in the checkerboard.

Checkerboard analysis was performed to assess the random (chemokinetic) versus the directed (chemotactic) nature of the motility response to ATX. Chambers were assembled with different concentrations of ATX above and below the filter, using ATX purified through the weak anion exchange fractionation step. Squares below the diagonal reflect response to a positive gradient, squares above reflect response to a negative gradient, and squares on the diagonal reflect random motility in the absence of a gradient. ATX stimulates both chemotactic and chemokinetic responses (FIG. 10), with chemotactic responses as high as fifteen-fold above background and chemokinesis as high as eight-fold above background.

Amino acid analysis after complete acid hydrolysis was used to quantitate purified protein. This hydrolysis was carried out on protein excised from a polyacrylamide gel and presumed to be pure. The analysis indicated that 2.7 nmol of protein was present after fractionation on the molecular sieve. After fractionation by strong anion exchange chromatography, approximately 300 pmol remained. The results of the analysis are shown in Table 3.

TABLE 3

AMINO ACID COMPOSITION OF AUTOTAXIN
(CYS and TRP were not determined in this analysis)

| Amino Acid | Residues/100 |
|---|---|
| ASX | 12.5 |
| THR | 6.0 |
| SER | 5.7 |
| GLX | 9.4 |
| PRO | 7.4 |
| GLY | 7.0 |
| ALA | 3.9 |
| VAL | 6.7 |
| MET | 1.2 |
| ILE | 4.3 |
| LEU | 9.0 |
| TYR | 5.2 |
| PHE | 5.2 |
| HIS | 3.8 |
| LYS | 7.4 |
| ARG | 5.4 |

Example 3

ATX Degradation and Determination of Amino Acid Sequence

Figure 11:
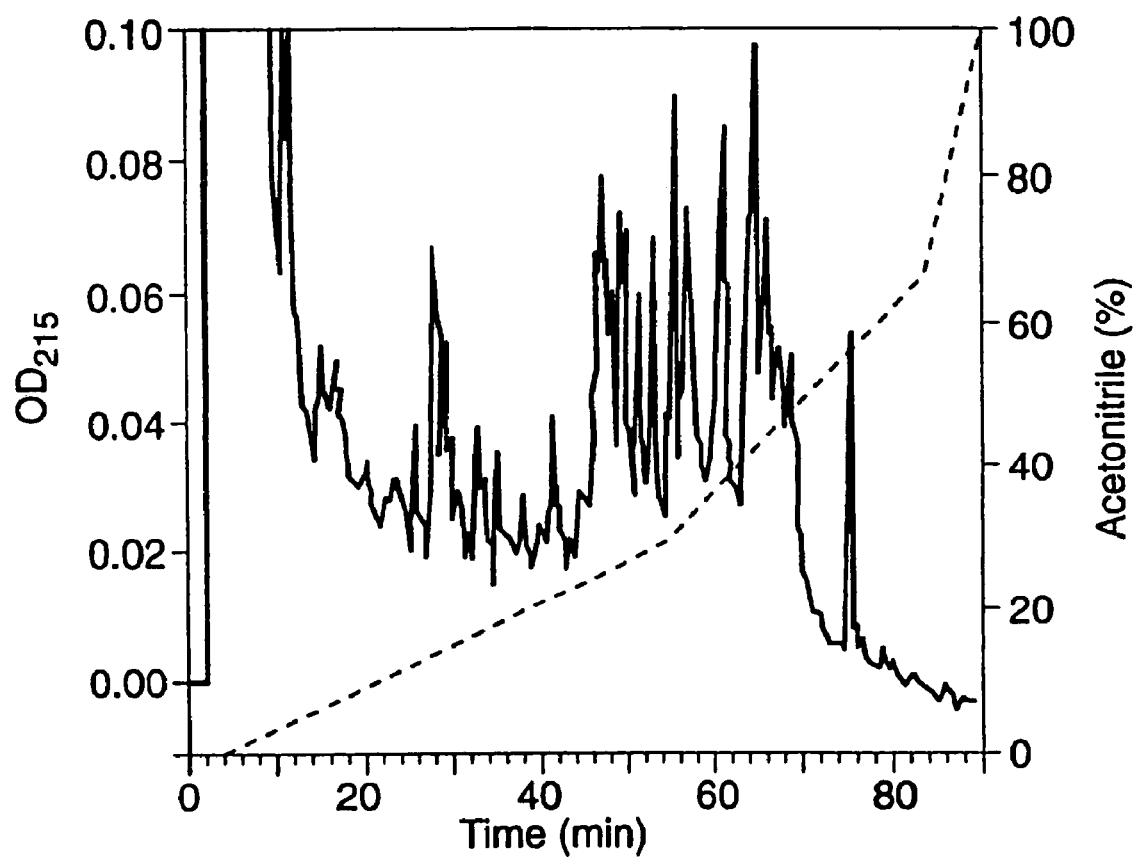
FIG. 11. Purification of ATX peptides on HPLC. ATX, purified to homogeneity by strong anionic exchange chromatography, was sequentially digested by cyanogen bromide, subjected to reduction and pyridylethylation, and digested by trypsin. The resulting peptides were purified-on an Aquapore RP300 C-8 reverse phase column using a (0-70)% acetonitrile gradient in 0.1% trifluoroacetic acid (----). The absorbance was monitored at 215 nm (_____) and peaks were collected. Seven peaks, chosen at random for N-terminal amino acid sequence analysis, are shown with appropriate numbers.

Attempts to obtain N-terminal sequence information from purified ATX repeatedly proved futile. The purified protein was therefore, sequentially digested and the resulting peptides fractionated by reverse phase chromatography. The results are shown in FIG. 11. Multiple sharp peaks including clusters at both the hydrophilic and hydrophobic ends of the gradient are seen.

Several of these peptide peaks were chosen randomly for Edman degradation and N-terminal amino acid sequence analysis. Seven of the eight peaks (shown in FIG. 11) chosen gave clear single sequence information as seen in Table 4. Using material from a separate digestion and purification, the remaining four sequences were also obtained.

Separate sense and antisense oligonucleotide probes were synthesized according to the fragment sequences of Table 4 by methods known to one skilled in the art. Representative probes are shown in Table 5.

TABLE 4

Peptide sequences for Autotaxin.

| PEPTIDE NO. | AMINO ACID SEQUENCE | SEQ ID: NO: | NAME |
|---|---|---|---|
| 1. | WHVA | SEQ ID NO: 1 | ATX 18 |
| 2. | PLDVYK | SEQ ID NO: 2 | ATX 19 |
| 3. | YPAFK | SEQ ID NO: 3 | ATX 20 |
| 4. | QAEVS | SEQ ID NO: 4 | ATX 24 |
| 5. | PEEVTRPNYL | SEQ ID NO: 5 | ATX 29 |
| 6. | YDVPWNETI | SEQ ID NO: 6 | ATX 47 |
| 7. | VPPFENIELY | SEQ ID NO: 7 | ATX 48 |
| 8. | GGQPLWITATK | SEQ ID NO: 8 | ATX 100 |
| 9. | VNSMQTVFVGY-GPTFK | SEQ ID NO: 9 | ATX 101 |
| 10. | DIEHLTSLDFFR | SEQ ID NO: 10 | ATX 102 |
| 11. | TEFLSNYLTNVDD-ITLVPETLGR | SEQ ID NO: 11 | ATX 103 |
| 12. | QYLHQYGSS | SEQ ID NO: 26 | ATX 37 |
| 13. | VLNYF | SEQ ID NO: 27 | ATX 39 |
| 14. | YLNAT | SEQ ID NO: 28 | ATX 40 |
| 15. | HLLYGRPAVLY | SEQ ID NO: 29 | ATX 41 |
| 16. | SYPEILTPADN | SEQ ID NO: 30 | ATX 44 |
| 17. | XYGFLFPPYLSSSP | SEQ ID NO: 31 | ATX 53 |
| 18. | TFPNLYTFATGLY | SEQ ID NO: 32 | ATX 59 |
| 19. | VNVISGPIFDYDYDGLHDTEDK | SEQ ID NO: 33 | ATX 104 |

Peptide numbers 1-7 refer to peaks numbered in FIG. 11. Peptide numbers 12-18 refer to peptides purified from the preparation which yielded peptide numbers 1-7. Peptides 8-11 and 19, are from a separate purification, not shown in FIG. 11.
X refers to potentially glycosylated residues.

TABLE 5

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEO ID NO: |
|---|---|---|
| A-18A | GTT-GGC-AGC-NAC-RTG-CCA | SEQ ID NO: 12 |
| A-18S | TGG-CAY-GTN-GCT-GCC-AAC | SEQ ID NO: 13 |
| A-20A | CTT-GAA-GGC-AGG-GTA | SEQ ID NO: 14 |
| A-20S | TAY-CCT-GCN-TTY-AAG | SEQ ID NO: 15 |
| A-29A | GGT-NAC-YTC-YTC-AGG | SEQ ID NO: 16 |
| A-29S | CCT-GAR-GAR-GTN-ACC | SEQ ID NO: 17 |
| A-47A | NGT-NGC-RTC-RAA-TGG-CAC-RTC | SEQ ID NO: 18 |
| A-47S | GAY-GTG-CCA-TTY-GAY-GCN-ACN | SEQ ID NO: 19 |
| A-48A | GTT-DAT-RTT-STC-RAA-TGG-GGG | SEQ ID NO: 20 |
| A-48S | CCC-CCA-TTT-GAG-AAC-ATC-AAC | SEQ ID NO: 21 |
| A-100A | CTT-NGT-NGC-NGT-DAT-CCA-NAR-GGG-YTG-GCG-GCC | SEQ ID NO: 22 |
| A-100S | GGC-GGC-CAR-CCC-YTN-TGG-ATH-ACN-GCN-ACN-AAG | SEQ ID NO: 23 |
| A-101A | CTT-RAA-GGT-GGG-GCC-RTA-GCC-CAC-RAA-GAC-TGT-YTG-CAT | SEQ ID NO: 24 |

TABLE 5-continued

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEO ID NO: |
|---|---|---|
| A-101S | ATG-CAR-ACA-GTC-TTY-GTG-GGC-TAY-GGC-CCC-ACC-TTY-AAR | SEQ ID NO: 25 |

Example 4

Antipeptide Antibodies

Rabbits were injected with ATX-102 (SEQ ID NO: 10) which had been cross-linked to bovine serum albumin. Antisera from these rabbits was subjected to salt precipitation followed by purification using affinity chromatography with Affi-gel 10 beads covalently linked to the peptide, ATX-102 (SEQ ID NO: 10). This affinity purified antibody reacted with the partially purified protein on immunoblots. This same antibody has been used to perform immunohistochemical stains on human tissue.

Example 5

Enzymatic Deglycosylation of ATX

Purified ATX that was to be treated with peptide N-glycosidase F (PNGase F) was first dialyzed into 0.2 M sodium phosphate, 10% (v/v) ethylene glycol pH 7.0, using Centricon-30 ultrafiltration tubes. Varying concentrations of PNGase F were added to the ATX and incubated 16-18 hr. at 37° C. complete digestion appeared to occur at concentrations of enzyme above 30 mU/ml (where 1 U converts 1 mmol of substrate/min). For comparison, the experiments were repeated in the presence of 0.1 M β-mercaptoethanol or 0.1% (w/v) SDS plus 0.5% (v.v) Nonidet-P40. ATX that was to be treated with neuraminidase or O-glycosidase was dialyzed into 20 mM sodium phosphate, 0.1 M calcium acetate, and 10% (v/v) ethylene glycol (pH 7.2). Neuraminidase was added to a final concentration of 2 U/ml. For treatment with neuraminidase alone, this mixture was incubated 16-18 hr at 37° C. Since O-glycosidase requires the removal of terminal sialic acid residues for efficient deglycosylation, ATX was pre-incubated with neuraminidase for 30-125 mU/ml and incubated 16-18 hr. at 37° C. The treated ATX was then dialyzed into 50 mM Tris with 20% ethylene glycol for storage at 5% C.

Treatment of ATX with N-glycosylation Altering Agents

A2058 cells were split into four 150 cm$^2$ flasks and incubated until just subconfluent in DMEM supplemented with 10% fetal calf serum. The medium was then replaced with fresh 10% FCS/DMEM to which had been added DPBS for control, 1 mM dMAN, 1 mM NMdNM, or 10 mM (1.7 mg/ml) Swn. Concentrations of these pharmacological agents were similar to those previously described as inhibiting N-glycan processing enzymes in melanoma cells (Seftor, et al. 1991; Dennis, et al. 1990) as well as carcinoma cells (Ogier, et al. 1990). On the next day, each flask was washed twice with Dulbecco's phosphate buffered saline with calcium ("DPBS") then 20 ml of Dulbecco's minimum essential medium ("DMEM") supplemented with 0.01% (w/v) bovine serum albumin ("BSA") was added. The same concentration of each agent was added to the appropriate equilibrated flask and incubated for ~24 hr, after which the medium from each treatment group was collected, concentrated, washed into DPBS and stored at 5° C.

Cells from each flask were trypsinized and counted. There was no loss of viability or reduced cell number in any of the treatment groups compared to control cells.

Effect of PNGase F on ATX

ATX binds to concanavalin A ("Con A") agarose beads and is eluted with buffer containing 0.5 M methyl a-D-mannopyranoside, indicating that ATX is likely to contain mannose residues. Such mannose sugar residues are most characteristic of N-linked oligosaccharides. In order to verify that ATX contained asparagine-linked oligosaccharides, we treated it with the endoglycosidase, PNGase F, which cleaves high mannose, hybrid, and complex N-linked oligosaccharides at the asparagine residue.

Partially purified ATX was treated with 60 mU/ml of enzyme under a variety of increasingly denaturing conditions and then separated by polyacrylamide gel electrophoresis (FIG. 16). Lane 1 shows untreated material; the 125 kDA band (arrow) is autotaxin. When this material is treated overnight with PNGase F under very mild conditions, the size of the 125 kDa band decreases to ~100-105 kDa. Addition of 0.1 M b-mercaptoethanol (Lane 2) or 0.5% Nonidet-P40 (lane 3) to the ATX sample has no effect on the size of the resultant protein band. Even complete denaturation of ATX of boiling the sample for 3 min in 0.1% SDS with (lane 5) or without (lane 4) β-mercaptoethanol, followed by addition of 0.5% Nonidet-P40 to maintain enzymatic activity, has no effect on the final size of deglycosylated protein, indicating that the deglycosidation reaction was complete even under mild conditions.

Because these results showed that ATX contained N-linked oligosaccharide groups, it became important to see if these sugar moieties were necessary for stimulation of motility. The partially purified ATX sample was treated with varying concentrations of PNGase F (0.1 to 60 mU/ml) under mild, nondenaturing conditions. Analysis of the resulting digest by polyacrylamide gel electrophoresis is shown in FIG. 17A. As this figure shows, the digestion was incomplete using from 0.1 to 10 mU/ml of enzyme and resulted in a smear of protein between 100-125 kDa. However, at higher concentrations of enzyme, cleavage of N-linked oligosaccharides from ATX appears to be complete. When these different digestion products were compared for their capacity to stimulate motility (FIG. 17B), there was no significant difference between groups.

Example 6

Cloning the 3' end of Autotaxin (4C11)

Figure 12:
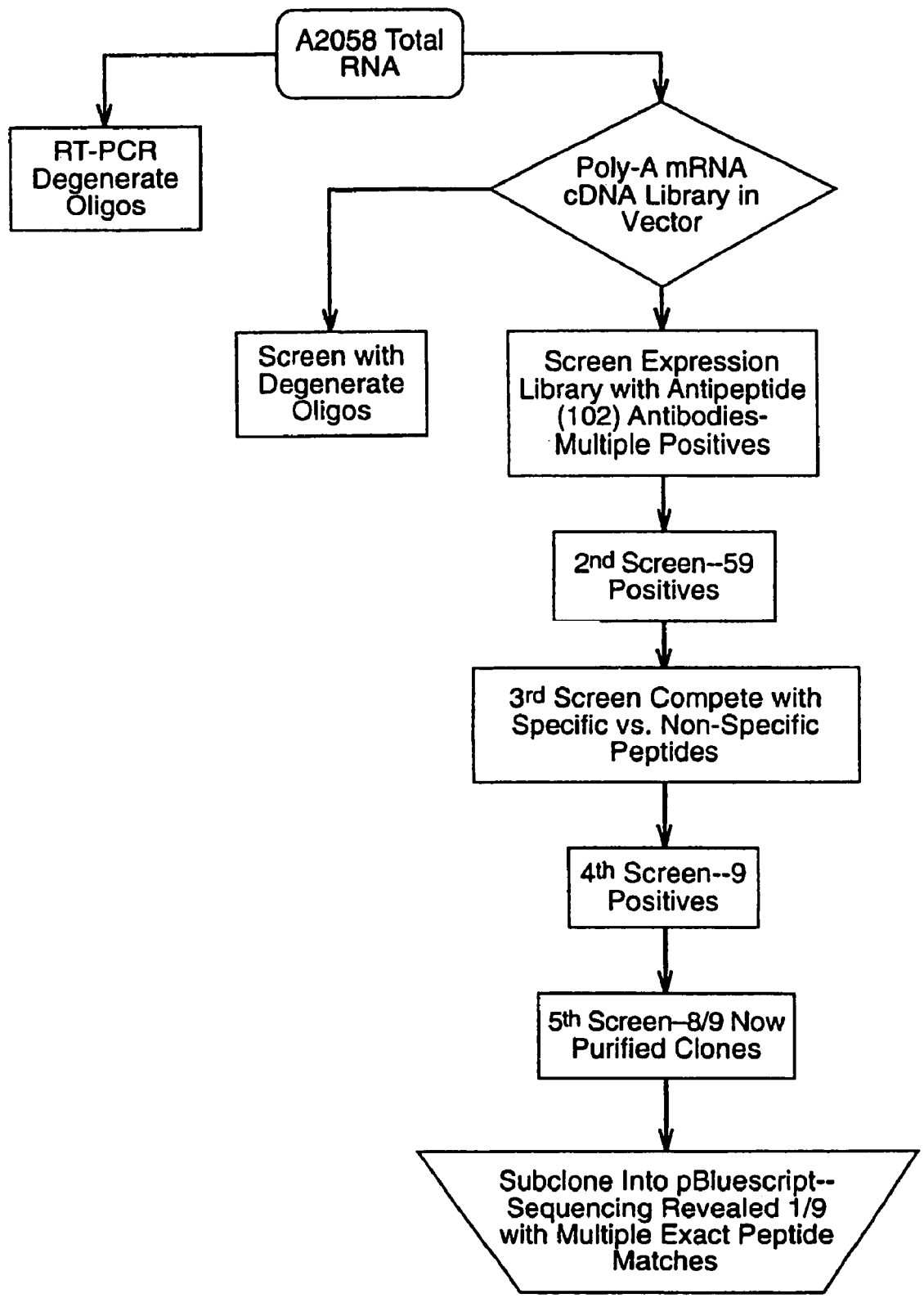
FIG. 12. Cloning Strategy, schematically depicted.

ATX is active in picomolar to nanomolar concentrations and is synthesized in very small concentrations by A2058 cells. As might be expected, the cDNA clone was relatively rare, requiring various strategies and multiple library screenings in order to identify it (FIG. 12). Attempts to utilize degenerate oligonucleotides deduced from known peptide sequences were unsuccessful—whether we used the oligonucleotides for screening cDNA libraries or for reverse transcription of mRNA followed by amplification with the polymerase chain reaction (RT/PCR). We then utilized an affinity-purified anti-peptide ATX-102 antibodies to screen an A2058 expression library.

These anti-peptide antibodies were generated by methods well established in the art and described previously with slight modification (Wacher, et al., 1990). In brief, the previously identified peptide, ATX-102 (Stracke, et al., 1992), was synthesized on a Biosearch 9600 peptide synthesizer. It was then solubilized in 1× PBS containing 20% (v/v) DMSO and conjugated to the protein carrier, bovine serum albumin (BSA), with glutaraldehyde. For the first injection into New Zealand white rabbits, the BSA-peptide conjugate was emulsified with complete Freund's adjuvant and injected subcutaneously. For subsequent injections, the BSA-peptide conjugate was emulsified with incomplete Freund's adjuvant. The resultant antiserum was heat-inactivated at 56° C. for 30 min. Immunoglobulins were precipitated out in 47% saturated ammonium sulfate, then redissolved and dialyzed into PBS. Antibodies were adsorbed onto peptide-conjugated Affi-Gel 10 resin (made using the BioRad protocol), eluted with 0.1 N acetic acid, and neutralized with 2 M Tris-HCl, pH 8. The resulting affinity-purified antibodies were dialyzed into DPBS, concentrated, aliquotted, and stored at −20° C. The antibodies were found to recognize a 125 kDa protein on immunoblots of partially purified A2058 conditioned medium and to preferentially stain some breast carcinoma cells compared to normal breast using-immunohistochemical techniques.

An A2058 cDNA library was prepared by purifying poly-A purified mRNA from the cells then size-selecting mRNA>1000 bp for the preparation of cDNA. The cDNA inserts were placed into λgt11 directionally, using the ProMega cDNA kit using standard methods well-established in the field. LE 392 cells were infected with the λgt11 and plaques were transferred onto nitrocellulose membranes by overnight incubation at 37° C. The antibody was incubated with the membranes in blocking buffer for 2 hr at room temperature, using approximately twice the concentration of antibody which gave a strong response on Western blot analysis. Secondary antibody was goat anti-rabbit immunoglobulin, and the blot was developed colorimetrically with 4-chloro-1-naphthol.

Positive clones were confirmed by antibody competition with specific peptides but not unrelated peptides. Using this technique and multiple subclonings, we obtained a partial cDNA clone of the autotaxin gene, which we called 4C11. The 4C11 insert was removed from λgt11 by restriction enzyme digests and subcloned into pBluescript for sequencing by standard Sanger techniques (Sanger, et al., 1977). The 4C11 clone contained bases, including the poly-adenylated tail and the AATAAA adenylation signal locus, i.e., it contained the 3' terminus of the gene. It also included a 627 base open reading frame. Database analysis of this nucleotide sequence revealed that it is unique. The predicated amino acid sequence for 4C11 is 209 amino acids long with exact matches for 7 previously identified ATX peptides: (ATX-20, ATX-34, ATX-102, ATX-104, ATX-204, ATX-215, and ATX-244).

Example 7

Cloning the 5' Terminus of ATX

Database analysis of the 3' terminus of the ATX gene demonstrated a novel protein. However, we have found an interesting homology that has helped to guide us in exploring its function. ATX had a 45% amino acid identity and a 57% nucleotide identity with PC-1, a marker of B cell activation found on the surface of plasma cells. Using the PC-1 protein sequence as a guide, we found that ATX peptide homologies were scattered throughout the length of the protein. The only exception was the far amino terminus of PC-1, which includes the transmembrane and intracellular domains, and which had no homologies. Knowing approximate localization of the ATX peptides along the length of ATX, we then amplified different segments of ATX by the PCR (FIG. 13). These amplified segments of DNA were then subcloned into plasmids utilizing the TA Cloning kit of ProMega. The PCR amplified DNA could then be sequenced using standard Sanger sequencing techniques (Sanger, et al., 1977).

Cloning of Full Length ATX Gene

A reverse transcriptase reaction was performed using total or oligo-(dT) purified RNA from A2058 or N-tera 2D1 cells as template and an anti-sense primer from the 5' end of 4C11 (GCTCAGATAAGGAGGAAAGAG). This was followed by one or two PCR amplification of the resultant cDNA using the commercially available kit from Perkin-Elmer and following manufacturer's directions. These PCR reactions utilized nested antisense primers from 4C11 (GAATCCGTAGGA-CATCTGCTT and TGTAGGCCAAACAGTTCTGAC) as well as degenerate, nested sense primers deduced from ATX peptides: ATX-101 (AAYTCIATGCARACIGTITTYGTIG and TTYGTIGGITAYGGICCIACITTYAA), ATX-103 (AAYTAYCTIACIAAYGTIGAYGAYAT and GAYGAYA-TIACICTIGTICCIGGIAC), or ATX-224 (TGYTTYGA-RYTICARGARGCIGGICCICC). The amplified DNA was then purified from a polyacrylamide gel using standard procedures and ligated into the pCR™ plasmid using the TA cloning kit (Invitrogen Corporation) according to manufacturer's directions.

The 5' RACE kit was utilized to extend the 5' end of ATX cDNA using total RNA from N-tera 2D1 as template and previously obtained sequence as primer (GCTGTCT-TCAAACACAGC). The 5' end of the A2058 synthesized protein was obtained by using previously obtained sequence as primer (CTGGTGGCTGTAATCCATAGC) in a reverse transcriptase reaction with total A2058 RNA as template, followed by PCR amplification utilizing the 5' end of N-tera 2D1 sequence as sense primer (CGTGAAGGCAAA-GAGAACACG) and a nested antisense primer (GCTGTCT-TCAAACACAGC). A2058 DNA encoding ATX is set forth in a SEQ ID NO:68 and the amino acid sequence is provided in SEQ ID NO:69.

DNA sequencing: DNA sequencing was performed using dideoxy methodology (Sanger, et al. 1977) and ($^{35}$S)dATP (Du Pont, New England Nuclear).

We have found one region between the 5' end of the 4C11 and the ATX peptide designated ATX-101, also referred to as the "hot spot". This region has been sequenced five times with different sequences found each time. The hot spot appears to be located within the region from approximately nucleotide 1670 to 1815. The consensus sequence is represented by amino acids position 559 through 604. Variations found include DNA sequence that results in single and multiple amino acid insertions. One sequence had a stop codon in this region and may have represented an intron. This region has been found to be variable in forms of ATX.

Example 8

Cloning ATX in a Human Teratocarcinoma Cell Line

The fact that ATX is present in other cancer cells was confirmed by sequence information from N-tera 2D1, a human teratocarcinoma cell line. For these cells, a prepared cDNA library in λgt10 was amplified and the cDNA inserts were extracted. Using oligonucleotide primers based on known A2058 ATX sequence, DNA segments were amplified by PCR. The DNA segments were then subcloned into plasmids and sequenced as for A2058. We have 3104 bp DNA sequence for N-tera ATX (SEQ ID NO:66) and smaller portions thereof. This includes an open reading frame that codes for a putative protein containing 861 amino acids (SEQ ID NO:67) and smaller portions thereof. Like the A2058 ATX, the N-tera 2D1 sequence has homologies for multiple ATX peptides (FIG. 15). Sequence homology between the A2058 and N-tera 2D1 cells is approximately 99%.

Example 9

Cloning 5' End of ATX in Human Normal Liver

The 5' end of ATX has proven difficult to obtain from either tumor cell line to date. Normal human liver mRNA was therefore amplified using the 5' RACE kit (Clontech) with known sequence from A2058 ATX as antisense primer. A DNA segment was obtained and has been sequenced. This segment codes for 979 amino acids, including an initiating methionine (SEQ ID NO: 71). The putative protein sequence also includes a 20 amino acid transmembrane domain which is different from the tumor ATX's (SEQ ID NO: 54), as shown in Table 7. Both tumorous forms of ATX apparently lack a transmembrane region and are instead secreted proteins.

TABLE 7

Nucleotide and Amino Acid Sequences Encoding Liver ATX Amino Terminus containing the Transmembrane region Protein Sequence (SEQ ID NO: 54)
Met Ala Arg Arg Ser Ser Phe Gln Ser Cys Gln Asp Ile Ser Leu Phe Thr Phe Ala Val Gly Val Asn Ile Cys Leu Gly Phe Thr Ala His Arg Ile Lys Arg Ala Glu Gly Trp DNA Sequence (SEQ ID NO: 53)
ATGGCAAGGA GGAGCTCGTT CCAGTCGTGT CAAGATATAT

CCCTGTTCAC

TTTTGCCGTT GGAGTCAATA TCTGCTTAGG ATTCACTGCA

CATCGAATTA

AGAGAGCAGA AGGATGG

Example 10

Domains of ATX

Searches of protein databases (Pearson, et. al. 1988) confirmed that the homology between ATX and PC-1 was present throughout the length of the extracellular portion of the molecules (Buckley, et. al., 1990; Funakoshi, et. al. 1992). There is a 45% amino acid identity and a 64% similarity between the 2 protein sequences (FIG. 18). For the cDNA sequence, the identity is ~57%.

These proteins share several interesting properties and domains (FIG. 19). Both have a number of potential N-linked glycosylation sites: four for ATX (Asn54, Asn463, Asn577, Asn859) and nine for PC-1. Both have adjacent somatomedin B domains near the amino end of the extracellular domain. This somatomedin B domain is a cysteine-rich region containing 3 presumed cystine cross-linkages. ATX has 33 Cys residues and PC-1 has 37; 30 of these Cys residues are identical in placement. Both proteins also contain the loop region of an EF hand (Buckley, et. al. 1990; Kretsinger, 1987). In addition, both proteins have a transmembrane/signal peptide region with a short intracellular peptide, common in ectoenzymes (Maroux, 1987). However, the amino acid identity between ATX and PC-1 in the intracellular and transmembrane regions is only 11%.

Finally, both proteins have a region homologous to the bovine intestinal phosphodiesterase enzymatic domain with conversation of the threonine that is thought to act as the intermediate phosphate binding site (Culp, et al. 1985). PC-1 has been demonstrated to have phosphodiesterase type I, nucleotide pyrophosphatase, and threonine-specific kinase enzymatic activities (Rebbe, et al. 1991; Oda, et al. 1991). In order to test whether purified ATX had type I phosphodiesterase activity, samples were incubated with p-nitrophenyl thymidine-5'-monophosphate at pH 8.9 for 30 min. Samples were assayed in a 100 λl volume containing 50 mM Tris-HCl, pH 8.9 and 5 mM p-nitrophenyl thymidine-5'-monophosphate. After a 30 minute incubation at 37° C. the reactions were terminated by addition of 900 ml 0.1 N NaOH and the amount of product formed was determined by reading the absorbance at 410 nm. ATX was found to hydrolyze the p-nitrophenyl thymidine-5'-monophosphate (Razzell, 1963) at a rate of 10 pmol/ng/min, a reaction rate similar to that reported for PC-1 (Oda, et al. 1993).

REFERENCES

Atnip, K. D., et al. (1987) *Biochem. Biophys. Res. Comm.* 146, 996-1002
Buckley, M. F., Loveland, K. A., McKinstry, W. J., Garson, O. M. and Goding, J. W. (1990) *J. Biol. Chem.* 265, 17506-17511
Culp, J. S., Blytt, H. J., Hermodson, M. and Butler, L. G. (1985) *J. Biol. Chem.* 260, 8320-8324
Dennis, J. W., Koch, K., Yousefi, S. and VanderElst, I. (1990) *Cancer Res.* 50, 1867-1872
Funakoshi, I., Kato, H., Horie, K., Yano, T., Hori, Y., Kobayashi, H., Inoue, T., Suzuki, H., Fukui, S., Tsukahara, M., Kajii, T. and Yamashina, I. (1992) *Arch. Biochem. Biophys.* 295, 180-187
Gospodarowicz, D. (1984) *Proc. Natl. Acad. Sci. USA* 81, 6963-6967
Guirguis, R., et al. (1987) *Nature* 329, 261-263
Jouanneau, J., et al. (1991) *Proc. Natl. Acad. Sci. USA* 88, 2893-2897
Kahan, B. W. et al., (1987) *Cancer Res.* 47, 6324-6328
Kretsinger, R. H. (1987) *Cold Spring Harbor Symp. Quant. Bio.* 52, 499-510
Kohler and Milstein, (1975) *Nature* 256:495-497
Kohn, E. C., et al. (1990) *Int. J. Cancer* 46, 287-292
Laemmli U. K. (1970) *Nature* 227, 680-685
Landsteiner, *Specificity of Serological Reactions* (Dover Publications, New York, 1962)
Liotta, L. A., et al. (1986) *Proc. Natl. Acad. Sci. USA* 83, 3302-3306
Liotta, L. A., et al. (1988) *Cancer surveys* 7, 631-652
Maciag, T., et al. (1984) *Sci.* 225, 932-935
Maroux, S. (1987) In A. J. Kenny and A. J. Turner (eds.) *Mammalian Ectoenzymes*, Elsevier Science Publishers B.V., Amsterdam, The Netherlands, 15-45
McCarthy, J. B., et al. (1984) *J. Cell Biol.* 98, 1474-1480 Microbiology, Hoeber Medical Division (Harper and Row, 1969)
Nabi, I. R., et al. (1990) *Cancer Res.* 50, 409-414
Neuhoff, V., et al. (1988) *Electrophoresis* 9, 255-262
Oda, Y., Kuo, M.-D., Huang, S. S. and Huang, J. S. (1991) *J. Biol. Chem.* 266, 16791-16795
Oda, Y., Kuo, M.-D., Huang, S. S. and Huang, J. S. (1993) *J. Biol. Chem.* 268, 27318-27326
O'Farrell, P. H. (1975) *J. Biol. Chem.* 250, 4007-4021
O'Farrell, P. H., et al. (1977) *Cell* 12, 1133-1142
Ogier-Denis, E., Trugnan, G., Sapin, C., Aubery, M. and Codogno, P. (1990) *J. Biol. Chem.* 265, 5366-5369
Ohnishi, T., et al. (1990) *J. Neurosurg.* 73, 881-888
Pearson, W. R., et al. (1988) *Proc. Natl. Acad. Sci. USA* 85, 2444-2448
Razzell, W. E. (1963) *Methods Enzymol.* 6, 236-258
Rebbe, N. F., Tong, B. D., Finley, E. M. and Hickman, S. (1991) *Proc. Natl. Acad. Sci. USA* 88, 5192-5196
Rosen, E. M. et al., (1989) *In Vitro Cell Devel. Biol.* 25, 163-173
Rosen, E. M., et al. (1990) *Proc. Soc. Exp. Biol. Med.* 195, 34-43
Ruff, M., et al. (1985) *Clin. Immunol. Immunopath.* 37, 387-396
Sanger, F. et al. (1977) *Proc. National Acad. Sci. USA.* 74, 5463-5467
Schnor, S. L., et al. (1988) *J. Cell Sci.* 90, 391-399
Seftor, R. E. B., Seftor, E. A., Grimes, W. J., Liotta, L. A., Stetler-Stevenson, W. G., Welch, D. R. and Hendrix, M. J. C. (1991) *Melanoma Res.* 1, 43-54
Silletti, S., et al. (1991) *Cancer Res.* 51, 3507-3511
Singer, S. J. and Kupfer, A. (1986) *Ann. Rev. Cell Biol.* 2, 337-365
Stites et al., editors, *Basic and Clinical Immunology*, (Lange Medical Publications, Los Altos, Calif., Fourth edition)
Stoker, M., et al. (1987) *Nature* 327, 239-242
Stone, M, et al. (1989) A *Practical Guide to Protein and Peptide Purification for Microsecuencing* (Matsudaira, P. T., ed.) pgs. 33-47, Academic Press, N.Y.
Stracke, M. L. et al., *Biochem. Biophys. Res. Comm.* 153, 1076-1083
Stracke, M. L., et al. (1978) *Biochem. Biophys. Res. Comm.* 146, 339-345
Stracke, M. L., et al. (1987) *Biochem. Biophys. Res. Comm.* 147, 339-345
Stracke, M. L., et al. (1988) *Biochem. Biophys. Res. Comm.* 153, 1076-1083
Tamm, I., et al., (1989) *J. Exp. Med.* 170, 1649-1669
Taraboletti, G., (1987) *J. Cell Biol.* 105, 2409-2415
Todaro, G. J., et al. (1980) *Proc. Natl. Acad. Sci. USA* 77, 5258-5262
Van Snick, J. (1990) *Ann. Rev. Immunol.* 8, 253-278
Wang, J. M., et al. (1990) *Biochem. Biophys. Res. Comm.* 169, 165-170
Watanabe, H., et al. (1990) *J. Cell Biol.* 111, 2097-2108
Watanabe, H., et al. (1991) *J. Biol. Chem.* 266, 13442-13448
Weidner, K. M., et al. (1990) *J. Cell. Biol.* 111, 2097-2108
Williams et al., *Methods in Immunology and Immunochemistry*, Vol. 1 (Academic Press, New York, 1967)
Yoshimura, T. (1987) *Proc. Natl. Acad. Sci. USA* 84, 9233-9237

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the present invention and appended claims.

The invention claimed is:

1. An isolated antibody or antigen-binding fragment thereof having binding affinity for autotaxin, wherein the antibody specifically binds to an autotoxin isolated from human melanoma A2058 cells, wherein the autotoxin (a) has an isoelectric point of about 7.7, (b) has a molecular weight of about 125 kDa as determined by SDS-polyacrylamide gel electrophoresis under reducing conditions, and (c) induces a motility in human A2058 melanoma cells which is inhibited by pertussis toxin.

2. An isolated antibody or antigen-binding fragment thereof that specifically binds to a polypeptide comprising the amino acid sequence of SEQ ID NO: 69.

* * * * *

SEQUENCE LISTING

<160> NUMBER OF SEQ ID NOS: 71

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Trp His Val Ala Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 2

Pro Leu Asp Val Tyr Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Tyr Pro Ala Phe Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Gln Ala Glu Val Ser
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Pro Glu Glu Val Thr Arg Pro Asn Tyr Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

Tyr Asp Val Pro Trp Asn Glu Thr Ile

```
<210> SEQ ID NO 7
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 7

Val Pro Pro Phe Glu Asn Ile Glu Leu Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Gly Gly Gln Pro Leu Trp Ile Thr Ala Thr Lys
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 9

Val Asn Ser Met Gln Thr Val Phe Val Gly Tyr Gly Pro Thr Phe Lys
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 10

Asp Ile Glu His Leu Thr Ser Leu Asp Phe Phe Arg
1               5                   10

<210> SEQ ID NO 11
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 11

Thr Glu Phe Leu Ser Asn Tyr Leu Thr Asn Val Asp Asp Ile Thr Leu
1               5                   10                  15

Val Pro Glu Thr Leu Gly Arg
            20

<210> SEQ ID NO 12
<211> LENGTH: 18
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (10)..(10)
```

<223> OTHER INFORMATION: Base n represents a or g or c or t/u, unknown,
      or other
<220> FEATURE:
<221> NAME/KEY: variation
<222> LOCATION: (13)..(13)
<223> OTHER INFORMATION: Base r represents g or a

<400> SEQUENCE: 12
gttggcagcn acrtgcca                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (6)..(6)
<223> OTHER INFORMATION: Base Y represents t/u or c
<220> FEATURE:
<221> NAME/KEY: variation
<222> LOCATION: (9)..(9)
<223> OTHER INFORMATION: Base n represents a or g or c or t/u, unknown,
      or other

<400> SEQUENCE: 13
tggcaygtng ctgccaac                                                 18

<210> SEQ ID NO 14
<211> LENGTH: 15
<212> TYPE: DNA
<213> ORGANISM: Artificial Sequence
<220> FEATURE:
<223> OTHER INFORMATION: Synthetic Primers

<400> SEQUENCE: 14
cttgaaggca gggta                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (3)..(3)
<223> OTHER INFORMATION: Base y  represents t/u or c
<220> FEATURE:
<221> NAME/KEY: variation
<222> LOCATION: (9)..(9)
<223> OTHER INFORMATION: Base n represents a or g or c or t/u, unknown,
      or other
<220> FEATURE:
<221> NAME/KEY: variation
<222> LOCATION: (12)..(12)
<223> OTHER INFORMATION: Base y  represents  t/u or c

<400> SEQUENCE: 15
taycctgcnt tyaag                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (4)..(4)
<223> OTHER INFORMATION: Base n represents a or g or c or t/u, unknown,

```
      or other
<220> FEATURE:
<221> NAME/KEY: variation
<222> LOCATION: (7)..(7)
<223> OTHER INFORMATION: Base y  represents t/u or c
<220> FEATURE:
<221> NAME/KEY: variation
<222> LOCATION: (10)..(10)
<223> OTHER INFORMATION: Base y  represents  t/u or c

<400> SEQUENCE: 16
ggtnacytcy tcagg                                                      15

<210> SEQ ID NO 17
<211> LENGTH: 15
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (6)..(6)
<223> OTHER INFORMATION: Base r represents a or g
<220> FEATURE:
<221> NAME/KEY: variation
<222> LOCATION: (9)..(9)
<223> OTHER INFORMATION: Base r represents a or g
<220> FEATURE:
<221> NAME/KEY: variation
<222> LOCATION: (12)..(12)
<223> OTHER INFORMATION: Base n represents a or g or c or t/u, unknown,
      or other

<400> SEQUENCE: 17
cctgargarg tnacc                                                      15

<210> SEQ ID NO 18
<211> LENGTH: 21
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (1)..(1)
<223> OTHER INFORMATION: Base n represents a or g or c or t/u, unknown,
      or other
<220> FEATURE:
<221> NAME/KEY: variation
<222> LOCATION: (4)..(4)
<223> OTHER INFORMATION: Base n represents a or g or c or t/u, unknown,
      or other
<220> FEATURE:
<221> NAME/KEY: variation
<222> LOCATION: (7)..(7)
<223> OTHER INFORMATION: Base r  represents a or g
<220> FEATURE:
<221> NAME/KEY: variation
<222> LOCATION: (10)..(10)
<223> OTHER INFORMATION: Base r  represents a or g
<220> FEATURE:
<221> NAME/KEY: variation
<222> LOCATION: (19)..(19)
<223> OTHER INFORMATION: Base r  represents a or g

<400> SEQUENCE: 18
ngtngcrtcr aatggcacrt c                                               21

<210> SEQ ID NO 19
<211> LENGTH: 21
<212> TYPE: DNA
<213> ORGANISM: Artificial Sequence
<220> FEATURE:
<223> OTHER INFORMATION: Synthetic Primers
```

```
<220> FEATURE:
<221> NAME/KEY: variation
<222> LOCATION: (3)..(3)
<223> OTHER INFORMATION: Base y represents t/u or c
<220> FEATURE:
<221> NAME/KEY: variation
<222> LOCATION: (12)..(12)
<223> OTHER INFORMATION: Base y represents t/u or c
<220> FEATURE:
<221> NAME/KEY: variation
<222> LOCATION: (15)..(15)
<223> OTHER INFORMATION: Base y  represents t/u or c
<220> FEATURE:
<221> NAME/KEY: variation
<222> LOCATION: (18)..(18)
<223> OTHER INFORMATION: Base n represents a or g or c or t/u, unknown,
      or other
<220> FEATURE:
<221> NAME/KEY: variation
<222> LOCATION: (21)..(21)
<223> OTHER INFORMATION: Base n represents a or g or c or t/u, unknown,
      or other

<400> SEQUENCE: 19
gaygtgccat tygaygcnac n                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (4)..(4)
<223> OTHER INFORMATION: Base d represents a or g or t/u
<220> FEATURE:
<221> NAME/KEY: variation
<222> LOCATION: (7)..(7)
<223> OTHER INFORMATION: Base r  represents a or g
<220> FEATURE:
<221> NAME/KEY: variation
<222> LOCATION: (10)..(10)
<223> OTHER INFORMATION: Base s  represents g or c
<220> FEATURE:
<221> NAME/KEY: variation
<222> LOCATION: (13)..(13)
<223> OTHER INFORMATION: Base r  represents a or g

<400> SEQUENCE: 20
gttdatrtts tcraatgggg g                                             21

<210> SEQ ID NO 21
<211> LENGTH: 21
<212> TYPE: DNA
<213> ORGANISM: Artificial Sequence
<220> FEATURE:
<223> OTHER INFORMATION: Synthetic Primers

<400> SEQUENCE: 21
cccccatttg agaacatcaa c                                             21

<210> SEQ ID NO 22
<211> LENGTH: 33
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (4)..(4)
<223> OTHER INFORMATION: Base n represents a or g or c or t/u, unknown,
      or other
<220> FEATURE:
```

```
<221> NAME/KEY: variation
<222> LOCATION: (7)..(7)
<223> OTHER INFORMATION: Base n represents a or g or c or t/u, unknown,
      or other
<220> FEATURE:
<221> NAME/KEY: variation
<222> LOCATION: (10)..(10)
<223> OTHER INFORMATION: Base n represents a or g or c or t/u, unknown,
      or other
<220> FEATURE:
<221> NAME/KEY: variation
<222> LOCATION: (13)..(13)
<223> OTHER INFORMATION: Base d represents a or g or t/u
<220> FEATURE:
<221> NAME/KEY: variation
<222> LOCATION: (19)..(19)
<223> OTHER INFORMATION: Base n represents a or g or c or t/u, unknown,
      or other
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: variation
<222> LOCATION: (21)..(21)
<223> OTHER INFORMATION: Base r  represents a or g
<220> FEATURE:
<221> NAME/KEY: variation
<222> LOCATION: (25)..(25)
<223> OTHER INFORMATION: Base y  represents c or t/u

<400> SEQUENCE: 22
cttngtngcn gtdatccana rgggytggcc gcc                                    33

<210> SEQ ID NO 23
<211> LENGTH: 33
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (9)..(9)
<223> OTHER INFORMATION: Base r represents a or g
<220> FEATURE:
<221> NAME/KEY: variation
<222> LOCATION: (13)..(13)
<223> OTHER INFORMATION: Base y represents c or t/u
<220> FEATURE:
<221> NAME/KEY: variation
<222> LOCATION: (15)..(15)
<223> OTHER INFORMATION: Base n represents a or g or c or t/u, unknown,
      or other
<220> FEATURE:
<221> NAME/KEY: variation
<222> LOCATION: (21)..(21)
<223> OTHER INFORMATION: Base h represents a or c or t/u
<220> FEATURE:
<221> NAME/KEY: variation
<222> LOCATION: (24)..(24)
<223> OTHER INFORMATION: Base n represents a or g or c or t/u, unknown,
      or other
<220> FEATURE:
<221> NAME/KEY: variation
<222> LOCATION: (27)..(27)
<223> OTHER INFORMATION: Base n represents a or g or c or t/u, unknown,
      or other
<220> FEATURE:
<221> NAME/KEY: variation
<222> LOCATION: (30)..(30)
<223> OTHER INFORMATION: Base n represents a or g or c or t/u, unknown,
      or other

<400> SEQUENCE: 23
ggcggccarc ccytntggat hacngcnacn aag                                    33
```

```
<210> SEQ ID NO 24
<211> LENGTH: 39
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (4)..(4)
<223> OTHER INFORMATION: Base r  represents a or g
<220> FEATURE:
<221> NAME/KEY: variation
<222> LOCATION: (16)..(16)
<223> OTHER INFORMATION: Base r  represents a or g
<220> FEATURE:
<221> NAME/KEY: variation
<222> LOCATION: (25)..(25)
<223> OTHER INFORMATION: Base r represents a or g
<220> FEATURE:
<221> NAME/KEY: variation
<222> LOCATION: (34)..(34)
<223> OTHER INFORMATION: Base y  represents c or t/u

<400> SEQUENCE: 24
cttraaggtg gggccrtagc ccacraagac tgtytgcat                              39

<210> SEQ ID NO 25
<211> LENGTH: 39
<212> TYPE: DNA
<213> ORGANISM: Artificial Sequence
<220> FEATURE:
<223> OTHER INFORMATION: Synthetic Primers
<220> FEATURE:
<221> NAME/KEY: variation
<222> LOCATION: (6)..(6)
<223> OTHER INFORMATION: Base r  represents a or g
<220> FEATURE:
<221> NAME/KEY: variation
<222> LOCATION: (15)..(15)
<223> OTHER INFORMATION: Base y represents c or t/u
<220> FEATURE:
<221> NAME/KEY: variation
<222> LOCATION: (24)..(24)
<223> OTHER INFORMATION: Base y  represents c or t/u
<220> FEATURE:
<221> NAME/KEY: variation
<222> LOCATION: (36)..(36)
<223> OTHER INFORMATION: Base y represents c or t/u
<220> FEATURE:
<221> NAME/KEY: variation
<222> LOCATION: (39)..(39)
<223> OTHER INFORMATION: Base r  represents a or g

<400> SEQUENCE: 25
atgcaracag tcttygtggg ctayggcccc accttyaar                              39

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 26

Gln Tyr Leu His Gln Tyr Gly Ser Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 27

Val Leu Asn Tyr Phe
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Tyr Leu Asn Ala Thr
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 29

His Leu Leu Tyr Gly Arg Pro Ala Val Leu Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 30

Ser Tyr Pro Glu Ile Leu Thr Pro Ala Asp Asn
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: CARBOHYD
<222> LOCATION: (1)..(1)
<223> OTHER INFORMATION: Xaa represents any amino acid, which is
      optionally glycosylated

<400> SEQUENCE: 31

Xaa Tyr Gly Phe Leu Phe Pro Pro Tyr Leu Ser Ser Ser Pro
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 32

Thr Phe Pro Asn Leu Tyr Thr Phe Ala Thr Gly Leu Tyr
1               5                   10

<210> SEQ ID NO 33
<211> LENGTH: 22
<212> TYPE: PRT
<213> ORGANISM: Artificial Sequence
```

<220> FEATURE:
<223> OTHER INFORMATION: Synthetic Polypeptide

<400> SEQUENCE: 33

Val Asn Val Ile Ser Gly Pro Ile Asp Asp Tyr Asp Tyr Asp Gly Leu
1 5 10 15

His Asp Thr Glu Asp Lys
20

<210> SEQ ID NO 34
<211> LENGTH: 829
<212> TYPE: PRT
<213> ORGANISM: Homo sapiens
<220> FEATURE:
<221> NAME/KEY: misc_feature
<223> OTHER INFORMATION: Putative protein sequence of A2058 Autotoxin

<400> SEQUENCE: 34

Cys His Asp Phe Asp Glu Leu Cys Leu Lys Thr Ala Arg Gly Trp Glu
1 5 10 15

Cys Thr Lys Asp Arg Cys Gly Glu Val Arg Asn Glu Glu Asn Ala Cys
20 25 30

His Cys Ser Glu Asp Cys Leu Ala Arg Gly Asp Cys Cys Thr Asn Tyr
35 40 45

Gln Val Val Cys Lys Gly Glu Ser His Trp Val Asp Asp Asp Cys Glu
50 55 60

Glu Ile Lys Ala Ala Glu Cys Pro Ala Gly Phe Val Arg Pro Pro Leu
65 70 75 80

Ile Ile Phe Ser Val Asp Gly Phe Arg Ala Ser Tyr Met Lys Lys Gly
85 90 95

Ser Lys Val Met Pro Asn Ile Glu Lys Leu Arg Ser Cys Gly Thr His
100 105 110

Ser Pro Tyr Met Arg Pro Val Tyr Pro Thr Lys Thr Phe Pro Asn Leu
115 120 125

Tyr Thr Leu Ala Thr Gly Leu Tyr Pro Glu Ser His Gly Ile Val Gly
130 135 140

Asn Ser Met Tyr Asp Pro Val Phe Asp Ala Thr Phe His Leu Arg Gly
145 150 155 160

Arg Glu Lys Phe Asn His Arg Trp Trp Gly Gly Gln Pro Leu Trp Ile
165 170 175

Thr Ala Thr Lys Gln Gly Val Lys Ala Gly Thr Phe Phe Trp Ser Val
180 185 190

Val Ile Pro His Glu Arg Arg Ile Leu Thr Ile Leu Arg Trp Leu Thr
195 200 205

Leu Pro Asp His Glu Arg Pro Ser Val Tyr Ala Phe Tyr Ser Glu Gln
210 215 220

Pro Asp Phe Ser Gly His Lys Tyr Gly Pro Phe Gly Pro Glu Glu Ser
225 230 235 240

Ser Tyr Gly Ser Pro Phe Thr Pro Ala Lys Arg Pro Lys Arg Lys Val
245 250 255

Ala Pro Lys Arg Arg Gln Glu Arg Pro Val Ala Pro Pro Lys Lys Arg
260 265 270

Arg Arg Lys Ile His Arg Met Asp His Tyr Ala Ala Glu Thr Arg Gln
275 280 285

Asp Lys Met Thr Asn Pro Leu Arg Glu Ile Asp Lys Ile Val Gly Gln
290 295 300

Leu Met Asp Gly Leu Lys Gln Leu Lys Leu Arg Arg Cys Val Asn Val

```
                305                 310                 315                 320
        Ile Phe Val Gly Asp His Gly Met Glu Asp Val Thr Cys Asp Arg Thr
                        325                 330                 335

Glu Phe Leu Ser Asn Tyr Leu Thr Asn Val Asp Asp Ile Thr Leu Val
                        340                 345                 350

Pro Gly Thr Leu Gly Arg Ile Arg Ser Lys Phe Ser Asn Asn Ala Lys
                        355                 360                 365

Tyr Asp Pro Lys Ala Ile Ile Ala Asn Leu Thr Cys Lys Lys Pro Asp
                        370                 375                 380

Gln His Phe Lys Pro Tyr Leu Lys Gln His Leu Pro Lys Arg Leu His
        385                 390                 395                 400

Tyr Ala Asn Asn Arg Arg Ile Glu Asp Ile His Leu Leu Val Glu Arg
                        405                 410                 415

Arg Trp His Val Ala Arg Lys Pro Leu Asp Val Tyr Lys Lys Pro Ser
                        420                 425                 430

Gly Lys Cys Phe Phe Gln Gly Asp His Gly Phe Asp Asn Lys Val Asn
                        435                 440                 445

Ser Met Gln Thr Val Phe Val Gly Tyr Gly Pro Thr Phe Lys Tyr Lys
                        450                 455                 460

Thr Lys Val Pro Pro Phe Glu Asn Ile Glu Leu Tyr Asn Val Met Cys
        465                 470                 475                 480

Asp Leu Leu Gly Leu Lys Pro Ala Pro Asn Asn Gly Thr His Gly Ser
                        485                 490                 495

Leu Asn His Leu Leu Arg Thr Asn Thr Phe Arg Pro Thr Met Pro Glu
                        500                 505                 510

Glu Val Thr Arg Pro Asn Tyr Pro Gly Ile Met Tyr Leu Gln Ser Asp
                        515                 520                 525

Asp Asp Leu Gly Cys Thr Cys Asp Asp Lys Val Glu Pro Lys Asn Lys
                        530                 535                 540

Leu Asp Glu Leu Asn Lys Arg Leu His Thr Lys Gly Ser Thr Glu Glu
        545                 550                 555                 560

Arg His Leu Leu Tyr Gly Arg Pro Ala Val Leu Tyr Arg Thr Arg Tyr
                        565                 570                 575

Asp Ile Leu Tyr His Thr Asp Phe Glu Ser Gly Tyr Ser Glu Ile Phe
                        580                 585                 590

Leu Met Leu Leu Trp Thr Ser Tyr Thr Val Ser Lys Gln Ala Glu Val
                        595                 600                 605

Ser Ser Val Pro Asp His Leu Thr Ser Cys Val Arg Pro Asp Val Arg
                        610                 615                 620

Val Ser Pro Ser Phe Ser Gln Asn Cys Leu Ala Tyr Lys Asn Asp Lys
        625                 630                 635                 640

Gln Met Ser Tyr Gly Phe Leu Phe Pro Pro Tyr Leu Ser Ser Ser Pro
                        645                 650                 655

Glu Ala Lys Tyr Asp Ala Phe Leu Val Thr Asn Met Val Pro Met Tyr
                        660                 665                 670

Pro Ala Phe Lys Arg Val Trp Asn Tyr Phe Gln Arg Val Leu Val Lys
                        675                 680                 685

Lys Tyr Ala Ser Glu Arg Asn Gly Val Asn Val Ile Ser Gly Pro Ile
        690                 695                 700

Phe Asp Tyr Asp Tyr Asp Gly Leu His Asp Thr Glu Asp Lys Ile Lys
        705                 710                 715                 720

Gln Tyr Val Glu Gly Ser Ser Ile Pro Val Pro Thr His Tyr Tyr Ser
                        725                 730                 735
```

```
Ile Ile Thr Ser Cys Leu Asp Phe Thr Gln Pro Ala Asp Lys Cys Asp
            740                 745                 750

Gly Pro Leu Ser Val Ser Ser Phe Ile Leu Pro His Arg Pro Asp Asn
        755                 760                 765

Glu Glu Ser Cys Asn Ser Ser Glu Asp Glu Ser Lys Trp Val Glu Glu
    770                 775                 780

Leu Met Lys Met His Thr Ala Arg Val Arg Asp Ile Glu His Leu Thr
785                 790                 795                 800

Ser Leu Asp Phe Phe Arg Lys Thr Ser Arg Ser Tyr Pro Glu Ile Leu
                805                 810                 815

Thr Leu Lys Thr Tyr Leu His Thr Tyr Glu Ser Glu Ile
            820                 825

<210> SEQ ID NO 35
<211> LENGTH: 2946
<212> TYPE: DNA
<213> ORGANISM: Homo sapiens
<220> FEATURE:
<221> NAME/KEY: misc_feature
<223> OTHER INFORMATION: Partial DNA sequence of A2058 Autotoxin

<400> SEQUENCE: 35
gctgccatga ctttgatgag ctgtgtttga agacagcccg tggctgggag tgtactaagg     60
acagatgtgg agaagtcaga aatgaagaaa atgcctgtca ctgctcagag gactgcttgg    120
ccaggggaga ctgctgtacc aattaccaag tggtttgcaa aggagagtcg cattgggttg    180
atgatgactg tgaggaaata aaggccgcag aatgccctgc agggtttgtt cgccctccat    240
taatcatctt ctccgtggat ggcttccgtg catcatacat gaagaaaggc agcaaagtca    300
tgcctaatat tgaaaaacta aggtcttgtg gcacacactc tccctacatg aggccggtgt    360
acccaactaa aacctttcct aacttataca ctttggccac tggggctatat ccagaatcac    420 atggaattgt tggcaattca atgtatgatc ctgtatttga tgccactttt catctgcgag    480
ggcgagagaa atttaatcat agatggtggg gaggtcaacc gctatggatt acagccacca    540
agcaaggggt gaaagctgga acattctttt ggtctgttgt catccctcac gagcggagaa    600
tattaaccat attgcggtgg ctcaccctgc cagatcatga gaggccttcg gtctatgcct    660
tctattctga gcaacctgat ttctctggac acaaatatgg ccctttcggc cctgaggaga    720
gtagttatgg ctcacctttt actccggcta agagacctaa gaggaaagtt gcccctaaga    780
ggagacagga aagaccagtt gctcctccaa agaaaagaag aagaaaaata cataggatgg    840
atcattatgc tgcggaaact cgtcaggaca aaatgacaaa tcctctgagg gaaatcgaca    900
aaattgtggg gcaattaatg gatggactga aacaactaaa actgcgtcgg tgtgtcaacg    960
tcatctttgt cggagaccat ggaatggaag atgtcacatg tgatagaact gagttcttga   1020
gtaattacct aactaatgtg gatgatatta ctttagtgcc tggaactcta ggaagaattc   1080
gatccaaatt tagcaacaat gctaaatatg accccaaagc cattattgcc aatctcacgt   1140
gtaaaaaacc agatcagcac tttaagcctt acttgaaaca gcaccttccc aaacgtttgc   1200
actatgccaa caacagaaga attgaggata tccatttatt ggtggaacgc agatggcatg   1260
ttgcaaggaa acctttggat gtttataaga aaccatcagg aaaatgcttt ttccagggag   1320
accacggatt tgataacaag gtcaacagca tgcagactgt tttgtaggt tatggcccaa    1380 catttaagta caagactaaa gtgcctccat ttgaaaacat tgaactttac aatgttatgt   1440
gtgatctcct gggattgaag ccagctccta ataatgggac ccatggaagt ttgaatcatc   1500
tcctgcgcac taataccttc aggccaacca tgccagagga agttaccaga cccaattatc   1560
```

```
caggga ttat gtaccttcag tctgattttg acctgggctg cacttgtgat gataaggtag    1620
agccaaagaa caagttggat gaactcaaca aacggcttca tacaaagggg tctacagaag    1680
agagacacct cctctatggg cgacctgcag tgctttatcg gactagatat gatatcttat    1740
atcacactga ctttgaaagt ggttatagtg aaatattcct aatgctactc tggacatcat    1800
atactgtttc caaacaggct gaggtttcca gcgttcctga ccatctgacc agttgcgtcc    1860
ggcctgatgt ccgtgtttct ccgagtttca gtcagaactg tttggcctac aaaaatgata    1920
agcagatgtc ctacggattc ctctttcctc cttatctgag ctcttcacca gaggctaaat    1980
atgatgcatt ccttgtaacc aatatggttc caatgtatcc tgctttcaaa cgggtctgga    2040
attatttcca aagggtattg gtgaagaaat atgcttcgga agaaatgga gttaacgtga    2100 taagtggacc aatcttcgac tatgactatg atggcttaca tgacacagaa acaaaataa    2160 aacagtacgt ggaaggcagt tccattcctg ttccaactca ctactacagc atcatcacca    2220
gctgtctgga tttcactcag cctgccgaca agtgtgacgg ccctctctct gtgtcctcct    2280
tcatcctgcc tcaccggcct gacaaagagg agagctgcaa tagctcagag gacgaatcaa    2340
aatgggtaga agaactcatg aagatgcaca cagctagggt gcgtgacatt gaacatctca    2400
ccagcctgga cttcttccga aagaccagcc gcagctaccc agaaatcctg acactcaaga    2460
catacctgca tacatatgag agcgagattt aacttcctga gcatctgcag tacagtctta    2520
tcaactggtt gtatattttt atattgtttt tgtatttatt aatttgaaac caggacatta    2580
aaaatgttag tattttaatc ctgtaccaaa tctgacatat tatgcctgaa tgactccact    2640 gttttctct aatgcttgat ttaggtagcc ttgtgttctg agtagagctt gtaataaata    2700
ctgcagcttg agaaaaagtg gaagcttcta aatggtgctg cagatttgat atttgcattg    2760
aggaaatatt aattttccaa tgcacagttg ccacatttag tcctgtactg tatggaaaca    2820
ctgattttgt aaagttgcct ttatttgctg ttaactgtta actatgacag atatatttaa    2880
gccttataaa ccaatcttaa acataataaa tcacacattc agttttaaaa aaaaaaaaaa    2940
aaaaaa                                                                 2946
```

<210> SEQ ID NO 36
<211> LENGTH: 788
<212> TYPE: PRT
<213> ORGANISM: Homo sapiens
<220> FEATURE:
<221> NAME/KEY: misc_feature
<223> OTHER INFORMATION: N-tera 2D1 putative ATX protein sequence

<400> SEQUENCE: 36

```
Cys Asp Asn Leu Cys Lys Ser Tyr Thr Ser Cys Cys His Asp Phe Asp
1               5                   10                  15

Glu Leu Cys Leu Lys Thr Ala Arg Ala Trp Glu Cys Thr Lys Asp Arg
            20                  25                  30

Cys Gly Glu Val Arg Asn Glu Glu Asn Ala Cys His Cys Ser Glu Asp
        35                  40                  45

Cys Leu Ala Arg Gly Asp Cys Cys Thr Asn Tyr Gln Val Val Cys Lys
    50                  55                  60

Gly Glu Ser His Trp Val Asp Asp Cys Glu Glu Ile Lys Ala Ala
65                  70                  75                  80

Glu Cys Leu Gln Val Asp Ser Pro Ser Ile Asn His Leu Leu Arg Gly
                85                  90                  95

Trp Leu Pro Met Thr Ser Tyr Met Lys Lys Gly Ser Lys Val Met Pro
            100                 105                 110
```

```
Asn Ile Glu Lys Leu Arg Ser Cys Gly Thr His Ser Pro Tyr Met Arg
            115                 120                 125

Pro Val Tyr Pro Thr Lys Thr Phe Pro Asn Leu Tyr Thr Leu Ala Thr
    130                 135                 140

Gly Leu Tyr Pro Glu Ser His Gly Ile Val Gly Asn Ser Met Tyr Asp
145                 150                 155                 160

Pro Val Phe Asp Ala Thr Phe His Leu Arg Gly Arg Glu Lys Phe Asn
                165                 170                 175

His Arg Trp Trp Ala Gly Gln Pro Leu Trp Ile Thr Ala Thr Lys Gln
            180                 185                 190

Arg Gly Glu Ser Trp Asn Ile Leu Leu Val Cys Cys His Pro Ser Arg
        195                 200                 205

Ala Glu Ile Leu Thr Ile Leu Gln Trp Leu Thr Leu Pro Asp His Glu
    210                 215                 220

Arg Pro Ser Val Tyr Ala Phe Tyr Ser Glu Gln Pro Asp Phe Ser Gly
225                 230                 235                 240

His Lys His Met Pro Phe Gly Pro Glu Met Pro Asn Pro Leu Arg Glu
                245                 250                 255

Met His Lys Ile Val Gly Gln Leu Met Asp Gly Leu Lys Gln Leu Lys
            260                 265                 270

Leu His Arg Cys Val Asn Val Ile Phe Val Glu Thr Met Asp Gly Arg
        275                 280                 285

Cys His Met Tyr Arg Thr Glu Phe Leu Ser Asn Tyr Leu Thr Asn Val
    290                 295                 300

Asp Asp Ile Thr Leu Val Pro Gly Thr Leu Gly Arg Ile Arg Ser Lys
305                 310                 315                 320

Phe Ser Asn Asn Ala Lys Tyr Asp Pro Lys Ala Ile Ile Ala Asn Leu
                325                 330                 335

Thr Cys Lys Lys Pro Asp Gln His Phe Lys Pro Tyr Leu Lys Gln His
            340                 345                 350

Leu Pro Lys Arg Leu His Tyr Ala Asn Asn Arg Arg Ile Glu Asp Ile
        355                 360                 365

His Leu Leu Val Glu Arg Arg Trp His Val Ala Arg Lys Pro Leu Asp
    370                 375                 380

Val Tyr Lys Lys Pro Ser Gly Asn Ala Phe Ser Arg Glu Thr Thr Ala
385                 390                 395                 400

Phe Asp Asn Lys Val Asn Ser Met Gln Thr Val Phe Val Gly Tyr Gly
                405                 410                 415

Pro Thr Phe Lys Tyr Lys Thr Lys Val Pro Pro Phe Glu Asn Ile Glu
            420                 425                 430

Leu Tyr Asn Val Met Cys Asp Leu Leu Gly Leu Lys Pro Ala Pro Asn
        435                 440                 445

Asn Gly Thr His Phe Ser Leu Asn His Leu Leu Arg Thr Asn Thr Phe
    450                 455                 460

Arg Pro Thr Met Pro Glu Glu Val Thr Arg Pro Asn Tyr Pro Gly Ile
465                 470                 475                 480

Met Tyr Leu Gln Ser Asp Phe Asp Leu Gly Cys Thr Cys Asp Asp Lys
                485                 490                 495

Val Glu Pro Lys Asn Lys Leu Asp Glu Leu Asn Lys Arg Leu His Thr
            500                 505                 510

Lys Gly Ser Thr Glu Glu Arg His Leu Leu Tyr Gly Asp Arg Pro Ala
        515                 520                 525

Val Leu Tyr Arg Thr Arg Tyr Asp Ile Leu Tyr His Thr Asp Phe Glu
```

| | | | | | | | | | | | 530 | | | | | 535 | | | | | 540 | | |
|---|---|---|---|---|---|---|---|---|---|---|---|---|---|---|---|---|---|---|---|---|---|---|---|

Ser Gly Tyr Ser Glu Ile Phe Leu Met Pro Leu Trp Thr Ser Tyr Thr
545                 550                 555                 560

Val Ser Lys Gln Ala Glu Val Ser Ser Val Pro Asp His Leu Thr Ser
            565                 570                 575

Cys Val Arg Pro Asp Val Arg Val Ser Pro Phe Ser Gln Asn Cys
            580                 585                 590

Leu Ala Tyr Lys Asn Asp Lys Gln Met Ser Tyr Gly Gly Leu Gly Pro
            595                 600                 605

Pro Tyr Leu Ser Ser Ser Pro Glu Ala Lys Tyr Asp Ala Phe Leu Val
        610                 615                 620

Thr Asn Met Val Pro Met Tyr Pro Ala Phe Lys Arg Val Trp Asn Tyr
625                 630                 635                 640

Phe Gln Arg Val Leu Val Lys Lys Tyr Ala Ser Glu Arg Asn Gly Val
                645                 650                 655

Asn Val Ile Ser Gly Pro Ile Phe Asp Tyr Asp Tyr Asp Gly Leu His
            660                 665                 670

Asp Thr Glu Asp Lys Ile Lys Gln Tyr Val Glu Gly Ser Ser Ile Pro
            675                 680                 685

Val Pro Thr His Tyr Tyr Ser Ile Ile Thr Ser Cys Leu Asp Phe Thr
        690                 695                 700

Gln Pro Ala Asp Lys Cys Asp Gly Pro Leu Ser Val Ser Ser Phe Ile
705                 710                 715                 720

Leu Pro His Arg Pro Asp Asn Glu Glu Ser Cys Asn Ser Ser Glu Asp
            725                 730                 735

Glu Ser Lys Trp Val Glu Glu Leu Met Lys Met His Thr Ala Arg Val
            740                 745                 750

Arg Asp Ile Glu His Leu Thr Ser Leu Asp Phe Phe Arg Lys Thr Ser
        755                 760                 765

Arg Ser Tyr Pro Glu Ile Leu Thr Leu Lys Thr Tyr Leu His Thr Tyr
    770                 775                 780

Glu Ser Glu Ile
785

<210> SEQ ID NO 37
<211> LENGTH: 2712
<212> TYPE: DNA
<213> ORGANISM: Homo sapiens
<220> FEATURE:
<221> NAME/KEY: misc_feature
<223> OTHER INFORMATION: N-tera 2D1 ATX DNA sequence

<400> SEQUENCE: 37

```
tgtgacaact tgtgtaagag ctataccagt tgctgccatg actttgatga gctgtgtttg      60
aagacagccc gtgcgtggga gtgtactaag gacagatgtg gggaagtcag aaatgaagaa     120
aatgcctgtc actgctcaga ggactgcttg gccaggggag actgctgtaa caattaccaa     180
gtggtttgca aaggagagtc gcattgggtt gatgatgact gtgaggaaat aaaggccgca     240
gaatgcctgc aggtttgttc gccctccatt aatcatcttc tccgtggatg gcttccgatg     300
acatcataca tgaagaaagg cagcaaagtc atgcctaata ttgaaaaact aaggtcttgt     360
ggcacacact ctccctacat gaggccggtg tacccaacta aaacctttcc taacttatac     420
actttggcca ctgggctata tccagaatca catggaattg ttggcaattc aatgtatgat     480
cctgtatttg atgccacttt tcatctgcga gggcgagaga aatttaatca tagatggtgg     540
ggaggtcaac cgctatggat tacagccacc aagcaaaggg gtgaaagctg gaacattctt     600
```

```
ttggtctgtt gtcatccctc acgagcggag atattaacca tattgcagtg gctcaccctg    660
ccagatcatg agaggccttc ggtctatgcc ttctattctg agcaacctga tttctctgga    720
cacaaacata tgccttcgg ccctgagatg acaaatcctc tgagggaaat gcacaaaatt    780
gtggggcaat taatggatgg actgaaacaa ctaaaactgc atcggtgtgt caacgtcatc    840
tttgtcgaga ccatggatgg aagatgtcac atgtatagaa ctgagttctt gagtaattac    900
ctaactaatg tggatgatat tactttagtg cctggaactc taggaagaat tcgatccaaa    960
tttagcaaca atgctaaata tcaccccaaa gccattattg ccaatctcac gtgtaaaaaa   1020
ccagatcagc actttaagcc ttacttgaaa cagcaccttc ccaaacgttt gcactatgcc   1080
aacaacagaa gaattgagga tatccattta ttggtggaac gcagatggca tgttgcaagg   1140
aaacctttgg atgtttataa gaaaccatca ggaaatgctt tttccaggga gaccacggca   1200
tttgataaca aggtcaacag catgcagact gttttgtag gttatggccc aacatttaag   1260
tacaagacta aagtdcctcc atttgaaaac attgaacttt aaaatgttat gtgtgatctc   1320
ctgggattga agccagctcc taataatggg acccatggaa gtttgaatca tctcctgcgc   1380
actaatacct tcaggccaac catgccagag gaagttacca gacccctatta tccagggatt   1440 atgtaccttc agtctgattt tgacctgggc tgcacttgtg atgataaggt agagccaaag   1500
aacaagttgg atgaactcaa caaacggctt catacaaaag ggtctacaga agagagacac   1560
ctcctctatg gggatcgacc tgcagtgctt tatcggacta gatatgatat cttatatcac   1620
actgactttg aaagtggtta tagtgaaata ttcctaatgc cactctggac atcatatact   1680
gtttccaaac aggctgaggt ttccagcgtt cctgaccatc tgaccagttg cgtccggcct   1740
gatgtccgtg tttctccgag tttcagtcag aactgtttgg cctacaaaaa tgataagcag   1800
atgtcctacg gattcctctt tcctccttat ctgagctctt caccagaggc taaatatgat   1860
gcattccttg taaccaatat ggttccaatg tatcctgctt tcaaacgggt ctggaattat   1920
ttccaaaggg tattggtgaa gaaatatgct tcggaaagaa atggagttaa cgtgataagt   1980
ggaccaatct tcgactatga ctatgatggc ttacatgaca cagaagacaa aataaaacag   2040
tacgtggaag gcagttccat tcctgttcca actcactact acagcatcat caccagctgt   2100
ctggatttca ctcagcctgc cgacaagtgt gacggccctc tctctgtgtc ctccttcatc   2160
ctgcctcacc ggcctgacaa cgaggagagc tgcaatagtc cagaggacga atcaaaatgg   2220
gtagaagaac tcatgaagat gcacacagct agggtgcgtg acattgaaca tctccaccagc   2280 ctggacttct tccgaaagac cagccgcagc tacccagaaa tcctgacact caagacatac   2340
ctgcatacat atgagagcga gatttaactt tctgagcatc tgcagtacag tcttatcaac   2400
tggttgtata tttttatatt gtttttgtat ttattaattt gaaaccagga cattaaaaat   2460
gttagtattt taatcctgta ccaaatctga catattatgc ctgaatgact ccactgtttt   2520
tctctaatgc ttgatttagg tagccttgtg ttctgagtag agcttgtaat aaatactgca   2580
gcttgagttt ttagtggaag cttctaaatg gtgctgcaga tttgatattt gcattgagga   2640
aatattaatt ttccaatgca cagttgccac atttagtcct gtactgtatg gaaacactga   2700
ttttgtaaag tt                                                      2712
```

<210> SEQ ID NO 38
<211> LENGTH: 8
<212> TYPE: PRT
<213> ORGANISM: Artificial Sequence
<220> FEATURE:
<223> OTHER INFORMATION: Synthetic Polypeptide

```
<400> SEQUENCE: 38

Arg Val Trp Asn Tyr Phe Gln Arg
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 39

Met His Thr Ala Arg Val Arg Asp
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 40

Phe Ser Asn Asn Ala Lys Tyr Asp
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 41

Val Met Pro Asn Ile Glu Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 42

Thr Ala Arg Gly Trp Glu Cys Thr
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: VARIANT
<222> LOCATION: (1)..(1)
<223> OTHER INFORMATION: Xaa represents either an unknown or any amino
      acid residue
<220> FEATURE:
<221> NAME/KEY: VARIANT
<222> LOCATION: (7)..(7)
<223> OTHER INFORMATION: Xaa represents either an unknown or any amino
      acid residue

<400> SEQUENCE: 43

Xaa Asp Ser Pro Trp Thr Xaa Ile Ser Gly Ser
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 44

Leu Arg Ser Cys Gly Thr His Ser Pro Tyr Met
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 45

Thr Tyr Leu His Thr Tyr Glu Ser
1               5

<210> SEQ ID NO 46
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 46

Ala Ile Ile Ala Asn Leu Thr Cys Lys Lys Pro Asp Gln
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 47

Ile Val Gly Gln Leu Met Asp Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 48

Thr Ser Arg Ser Tyr Pro Glu Ile Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 49

Gln Ala Glu Val Ser Ser Val Pro Asp
1               5

```
<210> SEQ ID NO 50
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 50

Arg Cys Phe Glu Leu Gln Glu Ala Gly Pro Pro Asp Asp Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 51

Ser Tyr Thr Ser Cys Cys His Asp Phe Asp Glu Leu
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 52

Gln Met Ser Tyr Gly Phe Leu Phe Pro Pro Tyr Leu Ser Ser Ser Pro
1               5                   10                  15

<210> SEQ ID NO 53
<211> LENGTH: 117
<212> TYPE: DNA
<213> ORGANISM: Homo Sapiens
<220> FEATURE:
<221> NAME/KEY: misc_feature
<223> OTHER INFORMATION: 5' end of human liver ATX gene

<400> SEQUENCE: 53
atggcaagga ggagctcgtt ccagtcgtgt caagatatat ccctgttcac ttttgccgtt      60
ggagtcaata tctgcttagg attcactgca catcgaatta agagagcaga aggatgg       117

<210> SEQ ID NO 54
<211> LENGTH: 39
<212> TYPE: PRT
<213> ORGANISM: Homo sapiens
<220> FEATURE:
<221> NAME/KEY: misc_feature
<223> OTHER INFORMATION: N-terminal region including transmembrane
      domain of liver ATX protein

<400> SEQUENCE: 54

Met Ala Arg Arg Ser Ser Phe Gln Ser Cys Gln Asp Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp
        35

<210> SEQ ID NO 55
<211> LENGTH: 21
<212> TYPE: DNA
<213> ORGANISM: Artificial Sequence
<220> FEATURE:
```

<223> OTHER INFORMATION: Synthetic Primers

<400> SEQUENCE: 55
gctcagataa ggaggaaaga g                                          21

<210> SEQ ID NO 56
<211> LENGTH: 21
<212> TYPE: DNA
<213> ORGANISM: Artificial Sequence
<220> FEATURE:
<223> OTHER INFORMATION: Synthetic Primer

<400> SEQUENCE: 56
gaatccgtag gacatctgct t                                          21

<210> SEQ ID NO 57
<211> LENGTH: 21
<212> TYPE: DNA
<213> ORGANISM: Artificial Sequence
<220> FEATURE:
<223> OTHER INFORMATION: Synthetic Primer

<400> SEQUENCE: 57
tgtaggccaa acagttctga c                                          21

<210> SEQ ID NO 58
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: variation
<222> LOCATION: (3)..(3)
<223> OTHER INFORMATION: Base y represents t/u or c
<220> FEATURE:
<221> NAME/KEY: variation
<222> LOCATION: (6)..(6)
<223> OTHER INFORMATION: Base n represents inosine
<220> FEATURE:
<221> NAME/KEY: variation
<222> LOCATION: (12)..(12)
<223> OTHER INFORMATION: Base r represents g or a
<220> FEATURE:
<221> NAME/KEY: variation
<222> LOCATION: (15)..(15)
<223> OTHER INFORMATION: Base n represents inosine
<220> FEATURE:
<221> NAME/KEY: variation
<222> LOCATION: (18)..(18)
<223> OTHER INFORMATION: Base n represents inosine
<220> FEATURE:
<221> NAME/KEY: variation
<222> LOCATION: (21)..(21)
<223> OTHER INFORMATION: Base y represents c or t/u
<220> FEATURE:
<221> NAME/KEY: variation
<222> LOCATION: (24)..(24)
<223> OTHER INFORMATION: Base n represents inosine

<400> SEQUENCE: 58
aaytcnatgc aracngtntt ygtng                                      25

<210> SEQ ID NO 59
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: variation
<222> LOCATION: (3)..(3)

```
<223> OTHER INFORMATION: Base y represents c or  t/u
<220> FEATURE:
<221> NAME/KEY: variation
<222> LOCATION: (6)..(6)
<223> OTHER INFORMATION: Base n  represents inosine
<220> FEATURE:
<221> NAME/KEY: variation
<222> LOCATION: (9)..(9)
<223> OTHER INFORMATION: Base n  represents inosine
<220> FEATURE:
<221> NAME/KEY: variation
<222> LOCATION: (12)..(12)
<223> OTHER INFORMATION: Base y  represents c or  t/u
<220> FEATURE:
<221> NAME/KEY: variation
<222> LOCATION: (15)..(15)
<223> OTHER INFORMATION: Base n  represents inosine
<220> FEATURE:
<221> NAME/KEY: variation
<222> LOCATION: (18)..(18)
<223> OTHER INFORMATION: Base n  represents inosine
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: variation
<222> LOCATION: (21)..(21)
<223> OTHER INFORMATION: Base n  represents inosine
<220> FEATURE:
<221> NAME/KEY: variation
<222> LOCATION: (24)..(24)
<223> OTHER INFORMATION: Base y represents c or  t/u

<400> SEQUENCE: 59
ttygtnggnt ayggnccnac nttyaa                                          26

<210> SEQ ID NO 60
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: variation
<222> LOCATION: (3)..(3)
<223> OTHER INFORMATION: Base y represents c or  t/u
<220> FEATURE:
<221> NAME/KEY: variation
<222> LOCATION: (6)..(6)
<223> OTHER INFORMATION: Base y represents c or  t/u
<220> FEATURE:
<221> NAME/KEY: variation
<222> LOCATION: (9)..(9)
<223> OTHER INFORMATION: Base n  represents inosine
<220> FEATURE:
<221> NAME/KEY: variation
<222> LOCATION: (12)..(12)
<223> OTHER INFORMATION: Base n  represents inosine
<220> FEATURE:
<221> NAME/KEY: variation
<222> LOCATION: (15)..(15)
<223> OTHER INFORMATION: Base y  represents c or  t/u
<220> FEATURE:
<221> NAME/KEY: variation
<222> LOCATION: (18)..(18)
<223> OTHER INFORMATION: Base n  represents inosine
<220> FEATURE:
<221> NAME/KEY: variation
<222> LOCATION: (21)..(21)
<223> OTHER INFORMATION: Base y  represents c or  t/u
<220> FEATURE:
<221> NAME/KEY: variation
<222> LOCATION: (24)..(24)
<223> OTHER INFORMATION: Base y  represents c or  t/u

<400> SEQUENCE: 60
```
aaytayctna cnaaygtnga ygayat                                              26

```
<210> SEQ ID NO 61
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: variation
<222> LOCATION: (3)..(3)
<223> OTHER INFORMATION: Base y represents c or  t/u
<220> FEATURE:
<221> NAME/KEY: variation
<222> LOCATION: (6)..(6)
<223> OTHER INFORMATION: Base y represents c or  t/u
<220> FEATURE:
<221> NAME/KEY: variation
<222> LOCATION: (9)..(9)
<223> OTHER INFORMATION: Base n represents inosine
<220> FEATURE:
<221> NAME/KEY: variation
<222> LOCATION: (12)..(12)
<223> OTHER INFORMATION: Base n represents inosine
<220> FEATURE:
<221> NAME/KEY: variation
<222> LOCATION: (15)..(15)
<223> OTHER INFORMATION: Base n represents inosine
<220> FEATURE:
<221> NAME/KEY: variation
<222> LOCATION: (18)..(18)
<223> OTHER INFORMATION: Base n represents inosine
<220> FEATURE:
<221> NAME/KEY: variation
<222> LOCATION: (21)..(21)
<223> OTHER INFORMATION: Base n represents inosine
<220> FEATURE:
<221> NAME/KEY: variation
<222> LOCATION: (24)..(24)
<223> OTHER INFORMATION: Base n represents inosine

<400> SEQUENCE: 61
```
gaygayatna cnctngtncc nggnac                                              26

```
<210> SEQ ID NO 62
<211> LENGTH: 29
<212> TYPE: DNA
<213> ORGANISM: Artificial Sequence
<220> FEATURE:
<223> OTHER INFORMATION: Synthetic Primer
<220> FEATURE:
<221> NAME/KEY: variation
<222> LOCATION: (3)..(3)
<223> OTHER INFORMATION: Base y represents t/u or c
<220> FEATURE:
<221> NAME/KEY: variation
<222> LOCATION: (6)..(6)
<223> OTHER INFORMATION: Base y  represents c or t/u
<220> FEATURE:
<221> NAME/KEY: variation
<222> LOCATION: (9)..(10)
<223> OTHER INFORMATION: Base r  represents a or g.  Base y  represents
      c or t/u
<220> FEATURE:
<221> NAME/KEY: variation
<222> LOCATION: (12)..(12)
<223> OTHER INFORMATION: Base n  represents inosine
<220> FEATURE:
<221> NAME/KEY: variation
<222> LOCATION: (15)..(15)
<223> OTHER INFORMATION: Base r  represents a or g
<220> FEATURE:
<221> NAME/KEY: variation
<222> LOCATION: (18)..(18)
<223> OTHER INFORMATION: Base r  represents a or g
<220> FEATURE:
<221> NAME/KEY: variation
```

```
<222> LOCATION: (21)..(21)
<223> OTHER INFORMATION: Base n  represents inosine
<220> FEATURE:
<221> NAME/KEY: variation
<222> LOCATION: (24)..(24)
<223> OTHER INFORMATION: Base n  represents inosine
<220> FEATURE:
<221> NAME/KEY: variation
<222> LOCATION: (27)..(27)
<223> OTHER INFORMATION: Base n  represents inosine

<400> SEQUENCE: 62
tgyttygary tncargargc nggnccncc                                29

<210> SEQ ID NO 63
<211> LENGTH: 18
<212> TYPE: DNA
<213> ORGANISM: Artificial Sequence
<220> FEATURE:
<223> OTHER INFORMATION: Putative autotoxin protein sequence from human
      liver

<400> SEQUENCE: 63
gctgtcttca aacacagc                                            18

<210> SEQ ID NO 64
<211> LENGTH: 21
<212> TYPE: DNA
<213> ORGANISM: Artificial Sequence
<220> FEATURE:
<223> OTHER INFORMATION: Synthetic Primer

<400> SEQUENCE: 64
ctggtggctg taatccatag c                                        21

<210> SEQ ID NO 65
<211> LENGTH: 21
<212> TYPE: DNA
<213> ORGANISM: Artificial Sequence
<220> FEATURE:
<223> OTHER INFORMATION: Synthetic Primer

<400> SEQUENCE: 65
cgtgaaggca aagagaacac g                                        21

<210> SEQ ID NO 66
<211> LENGTH: 3104
<212> TYPE: DNA
<213> ORGANISM: Artificial Sequence
<220> FEATURE:
<223> OTHER INFORMATION: Synthetic Polynucleotide

<400> SEQUENCE: 66
agtgcactcc gtgaaggcaa agagaacacg ctgcaaaagg ctttccaata atcctcgaca      60
tggcaaggag gagctcgttc cagtcgtgtc agataatatc cctgttcact tttgccgttg     120
gagtcaatat ctgcttagga ttcactgcac atcgaattaa gagagcagaa ggatgggagg     180
aaggtcctcc tacagtgcta tcagactccc cctggaccaa catctccgga tcttgcaagg     240
gcaggtgctt tgaacttcaa gaggctggac ctcctgattg tcgctgtgac aacttgtgta     300
agagctatac cagttgctgc catgactttg atgagctgtg tttgaagaca gcccgtgcgt     360
gggagtgtac taaggacaga tgtggagaag tcagaaatga agaaaatgcc tgtcactgct     420
cagaggactg cttggccagg ggagactgct gtaccaatta ccaagtggtt tgcaaaggag     480
agtcgcattg ggttgatgat gactgtgagg aaataaaggc cgcagaatgc cctgcagggt     540
```

```
ttgttcgccc tccattaatc atcttctccg tggatggctt ccgtgcatca tacatgaaga    600
aaggcagcaa agtcatgcct aatattgaaa aactaaggtc ttgtggcaca cactcgcccc    660
acatgaggcc ggtgtaccca actaaaacct ttcctaactt atacactttg gccactgggc    720
tatatccaga atcacatgga attgttggca attcaatgta tgatcctgta tttgatgcca    780
cttttcatct gcgagggcga gagaaattta atcatagatg gtggggaggt caaccgctat    840
ggattacagc caccaagcaa aggggtgaaa gctggaacat tcttttggtc tgttgtcatc    900
cctcacgagc ggagatatta accatattgc agtggctcac cctgccagat catgagaggc    960
ttcggtctat gccttctatt ctgagcaacc tgatttctct ggacacaaat atgcctttcg   1020
gccctgagat gacaaatcct ctgagggaaa tcgacaaaat tgtggggcaa ttaatggatg   1080
gactgaaaca actaaaactg catcggtgtg tcaacgtcat ctttgtcgga gaccatggaa   1140
tggaagatgt cacatgtgat agaactgagt tcttgagtaa ttacctaact aatgtggatg   1200
atattacttt agtgcctgga actctaggaa ttcgatccaa atttagcaac aatgctaaat   1260
atgaccccaa agccattatt gccaatctca cgtgtaaaaa accagatcag cactttaagc   1320
cttacttgaa acagcacctt cccaaacgtt tgcactatgc caacaacaga gaattgagg    1380 atatccattt attggtggaa cgcagatggc atgttgcaag gaaacctttg gatgtttata   1440
agaaaccatc aggaaaatgc ttttccagg gagaccacgg atttgataac aaggtcaaca    1500
gcatgcagac tgttttgta ggttatggcc caacatttaa gtacaagact aaagtgcctc    1560
catttgaaaa cattgaactt tacaatgtta tgtgtgatct cctgggattg aagccagctc   1620
ctaataatgg gacccatgga agtttgaatc atctcctgcg cactaatacc ttcaggccaa   1680
ccatgccaga ggaagttacc agacccaatt atccagggat tatgtacctt cagtctgatt   1740
ttgacctggg ctgcacttgt gatgataagg tagagccaaa gaacaagttg gatgaactca   1800
acaaacggct tcatcaaaaa gggtctacag aagagagaca cctcctctat gggcgacctg   1860
cagtgcttta tcggactaga tatgatgtct tatatcacac tgactttgaa agtggttata   1920
gtgaaatatt cctaatgcca ctctggacat catatactgt ttccaaacag gctgaggttt   1980
ccagcgttcc tgaccatctg accagttgcg tccggcctga tgtccgtgtt tctccgagtt   2040
tcagtcagaa ctgtttggcc tacaaaaatg ataagcagat gtcctacgga ttcctctttc   2100
ctccttatct gagctcttca ccagaggcta aatatgatgc attccttgta accaatatgg   2160
ttccaatgta tcctgctttc aaacgggtct ggaattattt ccaagggta ttggtgaaga    2220 aatatgcttc ggaagaaat ggagttaacg tgataagtgg accaatcttc gactatgact    2280
atgatggctt acatgacaca gaagacaaaa taaaacagta cgtggaaggc agttccattc   2340
ctgttccaac tcactactac agcatcatca ccagctgtct ggatttcact cagcctgccg   2400
acaagtgtga cggccctctc tctgtgtcct ccttcatcct ccgtcaccgg cctgacaacg   2460
aggagagctg caatagctca gaggacgaat caaaatgggt agaagaactc atgaagatgc   2520
acacggctag ggtgcgtgac attgaacatc tcaccagcct ggacttcttc cgaaagacca   2580
gccgcagcta cccagaaatc ctgacactca agacatacct gcatacatat gagagcgaga   2640
tttaactttc tgagcatctg cagtacagtc ttatcaactg gttgtatatt tttatattgt   2700
ttttgtattt attaatttga aaccaggaca ttaaaaatgt tagtatttta atcctgtacc   2760
aaatctgaca tattatgcct gaatgactcc actgttttc tctaatgctt gatttaggta    2820
gccttgtgtt ctgagtagag cttgtaataa atactgcagc ttgagttttt agtgaaagct   2880
tctaaatggt gctgcagatt tgatatttgc attgaggaaa tattaatttt ccaatgcaca   2940
```

-continued

```
gttgccacat ttagtcctgt actgtatgga aacactgatt ttgtaaagtt gcctttattt    3000
gctgttaact gttaactatg acagatatat ttaagcctta taaaccaatc ttaaacataa    3060
taaatcacac attcagttttt ttctggtaaa aaaaaaaaaa aaaa                    3104
```

<210> SEQ ID NO 67
<211> LENGTH: 861
<212> TYPE: PRT
<213> ORGANISM: Artificial Sequence
<220> FEATURE:
<223> OTHER INFORMATION: Synthetic Polypeptide

<400> SEQUENCE: 67

```
Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Ala Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro His Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Arg Gly Glu Ser Trp
            260                 265                 270

Asn Ile Leu Leu Val Cys Cys His Pro Ser Arg Ala Glu Ile Leu Thr
        275                 280                 285

Ile Leu Gln Trp Leu Thr Leu Pro Asp His Glu Arg Leu Arg Ser Met
    290                 295                 300

Pro Ser Ile Leu Ser Asn Leu Ile Ser Leu Asp Thr Asn Met Pro Phe
305                 310                 315                 320

Gly Pro Glu Met Thr Asn Pro Leu Arg Glu Ile Asp Lys Ile Val Gly
                325                 330                 335

Gln Leu Met Asp Gly Leu Lys Gln Leu Lys Leu His Arg Cys Val Asn
```

-continued

```
                    340                 345                 350
Val Ile Phe Val Gly Asp His Gly Met Glu Asp Val Thr Cys Asp Arg
            355                 360                 365

Thr Glu Phe Leu Ser Asn Tyr Leu Thr Asn Val Asp Asp Ile Thr Leu
        370                 375                 380

Val Pro Gly Thr Leu Gly Ile Arg Ser Lys Phe Ser Asn Asn Ala Lys
385                 390                 395                 400

Tyr Asp Pro Lys Ala Ile Ile Ala Asn Leu Thr Cys Lys Lys Pro Asp
                405                 410                 415

Gln His Phe Lys Pro Tyr Leu Lys Gln His Leu Pro Lys Arg Leu His
            420                 425                 430

Tyr Ala Asn Asn Arg Arg Ile Glu Asp Ile His Leu Leu Val Glu Arg
        435                 440                 445

Arg Trp His Val Ala Arg Lys Pro Leu Asp Val Tyr Lys Lys Pro Ser
    450                 455                 460

Gly Lys Cys Phe Phe Gln Gly Asp His Gly Phe Asp Asn Lys Val Asn
465                 470                 475                 480

Ser Met Gln Thr Val Phe Val Gly Tyr Gly Pro Thr Phe Lys Tyr Lys
                485                 490                 495

Thr Lys Val Pro Pro Phe Glu Asn Ile Glu Leu Tyr Asn Val Met Cys
            500                 505                 510

Asp Leu Leu Gly Leu Lys Pro Ala Pro Asn Asn Gly Thr His Gly Ser
        515                 520                 525

Leu Asn His Leu Leu Arg Thr Asn Thr Phe Arg Pro Thr Met Pro Glu
    530                 535                 540

Glu Val Thr Arg Pro Asn Tyr Pro Gly Ile Met Tyr Leu Gln Ser Asp
545                 550                 555                 560

Phe Asp Leu Gly Cys Thr Cys Asp Asp Lys Val Glu Pro Lys Asn Lys
                565                 570                 575

Leu Asp Glu Leu Asn Lys Arg Leu His Thr Lys Gly Ser Thr Glu Glu
            580                 585                 590

Arg His Leu Leu Tyr Gly Arg Pro Ala Val Leu Tyr Arg Thr Arg Tyr
        595                 600                 605

Asp Val Leu Tyr His Thr Asp Phe Glu Ser Gly Tyr Ser Glu Ile Phe
    610                 615                 620

Leu Met Pro Leu Trp Thr Ser Tyr Thr Val Ser Lys Gln Ala Glu Val
625                 630                 635                 640

Ser Ser Val Pro Asp His Leu Thr Ser Cys Val Arg Pro Asp Val Arg
                645                 650                 655

Val Ser Pro Ser Phe Ser Gln Asn Cys Leu Ala Tyr Lys Asn Asp Lys
            660                 665                 670

Gln Met Ser Tyr Gly Phe Leu Phe Pro Pro Tyr Leu Ser Ser Ser Pro
        675                 680                 685

Glu Ala Lys Tyr Asp Ala Phe Leu Val Thr Asn Met Val Pro Met Tyr
    690                 695                 700

Pro Ala Phe Lys Arg Val Trp Asn Tyr Phe Gln Arg Val Leu Val Lys
705                 710                 715                 720

Lys Tyr Ala Ser Glu Arg Asn Gly Val Asn Val Ile Ser Gly Pro Ile
                725                 730                 735

Phe Asp Tyr Asp Tyr Asp Gly Leu His Asp Thr Glu Asp Lys Ile Lys
            740                 745                 750

Gln Tyr Val Glu Gly Ser Ser Ile Pro Val Pro Thr His Tyr Tyr Ser
        755                 760                 765
```

```
Ile Ile Thr Ser Cys Leu Asp Phe Thr Gln Pro Ala Asp Lys Cys Asp
770                 775                 780
Gly Pro Leu Ser Val Ser Ser Phe Ile Leu Arg His Arg Pro Asp Asn
785                 790                 795                 800
Glu Glu Ser Cys Asn Ser Ser Glu Asp Glu Ser Lys Trp Val Glu Glu
                805                 810                 815
Leu Met Lys Met His Thr Ala Arg Val Arg Asp Ile Glu His Leu Thr
            820                 825                 830
Ser Leu Asp Phe Phe Arg Lys Thr Ser Arg Ser Tyr Pro Glu Ile Leu
        835                 840                 845
Thr Leu Lys Thr Tyr Leu His Thr Tyr Glu Ser Glu Ile
    850                 855                 860

<210> SEQ ID NO 68
<211> LENGTH: 3251
<212> TYPE: DNA
<213> ORGANISM: Artificial Sequence
<220> FEATURE:
<223> OTHER INFORMATION: Synthetic Polynucleotide

<400> SEQUENCE: 68
cgtgaaggca aagagaacac gctgcaaaag gcttccaaga atcctcgaca tggcaaggag      60
gagctcgttc cagtcgtgtc agataatatc cctgttcact tttgccgttg gagtcagtat     120
ctgcttagga ttcactgcac atcgaattaa gagagcagaa ggatgggagg aaggtcctcc     180
tacagtgcta tcagactccc cctggaccaa catctccgga tcttgcaagg gcaggtgctt     240
tgaacttcaa gaggctggac tcctgattg tcgctgtgac aacttgtgta agagctatac      300
cagttgctgc catgactttg atgagctgtg tttgaagaca gcccgtggct gggagtgtac     360
taaggacaga tgtggagaag tcagaaatga agaaaatgcc tgtcactgct cagaggactg     420
cttggccagg ggagactgct gtaccaatta ccaagtggtt tgcaaaggag agtcgcattg     480
ggttgatgat gactgtgagg aaataaaggc cgcagaatgc cctgcagggt tgttcgccc     540 tccattaatc atcttctccg tggatggctt ccgtgcatca tacatgaaga aaggcagcaa     600
agtcatgcct aatattgaaa aactaaggtc ttgtggcaca cactctccct acatgaggcc     660
ggtgtaccca actaaaaacct ttcctaactt atacactttg gccactgggc tatatccaga     720
atcacatgga attgttggca attcaatgta tgatcctgta tttgatgcca cttttcatct     780
gcgagggcga gagaaattta atcatagatg gtggggaggt caaccgctat ggattacagc     840
caccaagcaa ggggtgaaag ctggaacatt cttttggtct gttgtcatcc ctcacgagcg     900
gagaatatta accatattgc ggtggctcac cctgccagat catgagaggc cttcggtcta     960
tgccttctat tctgagcaac tgatttctc tggacacaaa tatggccctt tcggccctga    1020
ggagagtagt tatggctcac ctttactcc ggctaagaga cctaagagga agttgccccc     1080
taagaggaga caggaaagac cagttgctcc tccaaagaaa agaagaagaa aaatacatag    1140
gatggatcat tatgctgcgg aaactcgtca ggacaaaatg acaaatcctc tgagggaaat    1200
cgacaaaatt gtggggcaat taatggatgg actgaaacaa ctaaaactgc gtcggtgtgt    1260
caacgtcatc tttgtcggag accatggaat ggaagatgtc acatgtgata gaactgagtt    1320
cttgagtaat tacctaacta atgtggatga tattactttta gtgcctggaa ctctaggaag    1380
aattcgatcc aaatttagca acaatgctaa atatgacccc aaagccatta ttgccaatct    1440
cacgtgtaaa aaaccagatc agcactttaa gccttacttg aaacagcacc ttccaaacg     1500 tttgcactat gccaacaaca gaagaattga ggatatccat ttattggtgg aacgcagatg    1560
```

-continued

```
gcatgttgca aggaaacctt tggatgttta agaaaccca tcaggaaaat gcttttcca    1620
gggagaccac ggatttgata acaaggtcaa cagcatgcag actgttttg taggttatgg   1680
cccaacattt aagtacaaga ctaaagtgcc tccatttgaa acattgaac tttacaatgt   1740
tatgtgtgat ctcctgggat tgaagccagc tcctaataat gggacccatg aagtttgaa   1800
tcatctcctg cgcactaata ccttcaggcc aaccatgcca gaggaagtta ccagacccaa   1860
ttatccaggg attatgtacc ttcagtctga ttttgacctg gctgcactt gtgatgataa   1920
ggtagagcca agaacaagt tggatgaact caacaaacgg cttcatacaa agggtctac    1980
agaagagaga cacctcctct atgggcgacc tgcagtgctt atcggacta gatatgatat   2040
cttatatcac actgactttg aaagtggtta tagtgaaata ttcctaatgc tactctggac   2100
atcatatact gtttccaaac aggctgaggt ttccagcgtt cctgaccatc tgaccagttg   2160
cgtccggcct gatgtccgtg tttctccgag tttcagtcag aactgtttgg cctacaaaaa   2220
tgataagcag atgtcctacg gattcctctt tcctccttat ctgagctctt caccagaggc   2280
taaatatgat gcattccttg taaccaatat ggttccaatg tatcctgctt tcaaacgggt   2340
ctggaattat ttccaaaggg tattggtgaa gaaatatgct tcggaaagaa atggagttaa   2400
cgtgataagt ggaccaatct tcgactatga ctatgatggc ttacatgaca cagaagacaa   2460
aataaaacag tacgtggaag cagttccat tcctgttcca actcactact acagcatcat   2520
caccagctgt ctggatttca ctcagcctgc cgacaagtgt gacggccctc tctctgtgtc   2580
ctccttcatc ctgcctcacc ggcctgcaaa cgaggagagc tgcaatagct cagaggacga   2640
atcaaaatgg gtagaagaac tcatgaagat gcacacagct agggtgcgtg acattgaaca   2700
tctcaccagc ctggacttct tccgaaagac cagccgcagc tacccagaaa tcctgacact   2760
caagacatac ctgcatacat atgagagcga gatttaactt tctgagcatc tgcagtacag   2820
tcttatcaac tggttgtata ttttatatt gttttgtat ttattaattt gaaaccagga   2880
cattaaaaat gttagtattt taatcctgta ccaaatctga catattatgc ctgaatgact   2940
ccactgtttt tctctaatgc ttgatttagg tagccttgtg ttctgagtag agcttgtaat   3000
aaatactgca gcttgagaaa aagtggaagc ttctaaatgg tgctgcagat tgatatttg   3060
cattgaggaa atattaattt tccaatgcac agttgccaca tttagtcctg tactgtatgg   3120
aaacactgat tttgtaaagt tgcctttatt tgctgttaac tgttaactat gacagatata   3180
tttaagcctt ataaccaat cttaaacata ataaatcaca cattcagttt taaaaaaaaa   3240
aaaaaaaaa a                                                        3251
```

<210> SEQ ID NO 69
<211> LENGTH: 915
<212> TYPE: PRT
<213> ORGANISM: Artificial Sequence
<220> FEATURE:
<223> OTHER INFORMATION: Synthetic Polypeptide

<400> SEQUENCE: 69

```
Met Ala Arg Arg Ser Ser Phe Gln Ser Cys Gln Ile Ile Ser Leu Phe
1               5                   10                  15

Thr Phe Ala Val Gly Val Ser Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60
```

```
Glu Leu Gln Glu Ala Gly Pro Pro Asp Cys Arg Cys Asp Asn Leu Cys
 65                  70                  75                  80
Lys Ser Tyr Thr Ser Cys Cys His Asp Phe Asp Glu Leu Cys Leu Lys
                 85                  90                  95
Thr Ala Arg Gly Trp Glu Cys Thr Lys Asp Arg Cys Gly Glu Val Arg
            100                 105                 110
Asn Glu Glu Asn Ala Cys His Cys Ser Glu Asp Cys Leu Ala Arg Gly
        115                 120                 125
Asp Cys Cys Thr Asn Tyr Gln Val Val Cys Lys Gly Glu Ser His Trp
    130                 135                 140
Val Asp Asp Asp Cys Glu Glu Ile Lys Ala Ala Glu Cys Pro Ala Gly
145                 150                 155                 160
Phe Val Arg Pro Pro Leu Ile Ile Phe Ser Val Asp Gly Phe Arg Ala
                165                 170                 175
Ser Tyr Met Lys Lys Gly Ser Lys Val Met Pro Asn Ile Glu Lys Leu
            180                 185                 190
Arg Ser Cys Gly Thr His Ser Pro Tyr Met Arg Pro Val Tyr Pro Thr
        195                 200                 205
Lys Thr Phe Pro Asn Leu Tyr Thr Leu Ala Thr Gly Leu Tyr Pro Glu
    210                 215                 220
Ser His Gly Ile Val Gly Asn Ser Met Tyr Asp Pro Val Phe Asp Ala
225                 230                 235                 240
Thr Phe His Leu Arg Gly Arg Glu Lys Phe Asn His Arg Trp Trp Gly
                245                 250                 255
Gly Gln Pro Leu Trp Ile Thr Ala Thr Lys Gln Gly Val Lys Ala Gly
            260                 265                 270
Thr Phe Phe Trp Ser Val Val Ile Pro His Glu Arg Arg Ile Leu Thr
        275                 280                 285
Ile Leu Arg Trp Leu Thr Leu Pro Asp His Glu Arg Pro Ser Val Tyr
    290                 295                 300
Ala Phe Tyr Ser Glu Gln Pro Asp Phe Ser Gly His Lys Tyr Gly Pro
305                 310                 315                 320
Phe Gly Pro Glu Glu Ser Ser Tyr Gly Ser Pro Phe Thr Pro Ala Lys
                325                 330                 335
Arg Pro Lys Arg Lys Val Ala Pro Lys Arg Arg Gln Glu Arg Pro Val
            340                 345                 350
Ala Pro Pro Lys Lys Arg Arg Lys Ile His Arg Met Asp His Tyr
        355                 360                 365
Ala Ala Glu Thr Arg Gln Asp Lys Met Thr Asn Pro Leu Arg Glu Ile
    370                 375                 380
Asp Lys Ile Val Gly Gln Leu Met Asp Gly Leu Lys Gln Leu Lys Leu
385                 390                 395                 400
Arg Arg Cys Val Asn Val Ile Phe Val Gly Asp His Gly Met Glu Asp
                405                 410                 415
Val Thr Cys Asp Arg Thr Glu Phe Leu Ser Asn Tyr Leu Thr Asn Val
            420                 425                 430
Asp Asp Ile Thr Leu Val Pro Gly Thr Leu Gly Arg Ile Arg Ser Lys
        435                 440                 445
Phe Ser Asn Asn Ala Lys Tyr Asp Pro Lys Ala Ile Ile Ala Asn Leu
    450                 455                 460
Thr Cys Lys Lys Pro Asp Gln His Phe Lys Pro Tyr Leu Lys Gln His
465                 470                 475                 480
Leu Pro Lys Arg Leu His Tyr Ala Asn Asn Arg Arg Ile Glu Asp Ile
                485                 490                 495
```

```
His Leu Leu Val Glu Arg Arg Trp His Val Ala Arg Lys Pro Leu Asp
                500                 505                 510

Val Tyr Lys Lys Pro Ser Gly Lys Cys Phe Phe Gln Gly Asp His Gly
                515                 520                 525

Phe Asp Asn Lys Val Asn Ser Met Gln Thr Val Phe Val Gly Tyr Gly
                530                 535                 540

Pro Thr Phe Lys Tyr Lys Thr Lys Val Pro Pro Phe Glu Asn Ile Glu
545                 550                 555                 560

Leu Tyr Asn Val Met Cys Asp Leu Leu Gly Leu Lys Pro Ala Pro Asn
                565                 570                 575

Asn Gly Thr His Gly Ser Leu Asn His Leu Leu Arg Thr Asn Thr Phe
                580                 585                 590

Arg Pro Thr Met Pro Glu Glu Val Thr Arg Pro Asn Tyr Pro Gly Ile
                595                 600                 605

Met Tyr Leu Gln Ser Asp Phe Asp Leu Gly Cys Thr Cys Asp Asp Lys
                610                 615                 620

Val Glu Pro Lys Asn Lys Leu Asp Glu Leu Asn Lys Arg Leu His Thr
625                 630                 635                 640

Lys Gly Ser Thr Glu Glu Arg His Leu Leu Tyr Gly Arg Pro Ala Val
                645                 650                 655

Leu Tyr Arg Thr Arg Tyr Asp Ile Leu Tyr His Thr Asp Phe Glu Ser
                660                 665                 670

Gly Tyr Ser Glu Ile Phe Leu Met Leu Leu Trp Thr Ser Tyr Thr Val
                675                 680                 685

Ser Lys Gln Ala Glu Val Ser Ser Val Pro Asp His Leu Thr Ser Cys
                690                 695                 700

Val Arg Pro Asp Val Arg Val Ser Pro Ser Phe Ser Gln Asn Cys Leu
705                 710                 715                 720

Ala Tyr Lys Asn Asp Lys Gln Met Ser Tyr Gly Phe Leu Phe Pro Pro
                725                 730                 735

Tyr Leu Ser Ser Ser Pro Glu Ala Lys Tyr Asp Ala Phe Leu Val Thr
                740                 745                 750

Asn Met Val Pro Met Tyr Pro Ala Phe Lys Arg Val Trp Asn Tyr Phe
                755                 760                 765

Gln Arg Val Leu Val Lys Lys Tyr Ala Ser Glu Arg Asn Gly Val Asn
                770                 775                 780

Val Ile Ser Gly Pro Ile Phe Asp Tyr Asp Tyr Asp Gly Leu His Asp
785                 790                 795                 800

Thr Glu Asp Lys Ile Lys Gln Tyr Val Glu Gly Ser Ser Ile Pro Val
                805                 810                 815

Pro Thr His Tyr Tyr Ser Ile Ile Thr Ser Cys Leu Asp Phe Thr Gln
                820                 825                 830

Pro Ala Asp Lys Cys Asp Gly Pro Leu Ser Val Ser Ser Phe Ile Leu
                835                 840                 845

Pro His Arg Pro Asp Asn Glu Glu Ser Cys Asn Ser Ser Glu Asp Glu
                850                 855                 860

Ser Lys Trp Val Glu Glu Leu Met Lys Met His Thr Ala Arg Val Arg
865                 870                 875                 880

Asp Ile Glu His Leu Thr Ser Leu Asp Phe Phe Arg Lys Thr Ser Arg
                885                 890                 895

Ser Tyr Pro Glu Ile Leu Thr Leu Lys Thr Tyr Leu His Thr Tyr Glu
                900                 905                 910

Ser Glu Ile
```

-continued

```
                915

<210> SEQ ID NO 70
<211> LENGTH: 873
<212> TYPE: PRT
<213> ORGANISM: Artificial Sequence
<220> FEATURE:
<223> OTHER INFORMATION: Synthetic Polypeptide

<400> SEQUENCE: 70

Met Asp Val Gly Glu Glu Pro Leu Glu Lys Ala Ala Arg Ala Arg Thr
1               5                   10                  15

Ala Lys Asp Pro Asn Thr Tyr Lys Val Leu Ser Leu Val Leu Ser Val
            20                  25                  30

Cys Val Leu Thr Thr Ile Leu Gly Cys Ile Phe Gly Leu Lys Pro Ser
        35                  40                  45

Cys Ala Lys Glu Val Lys Ser Cys Lys Gly Arg Cys Phe Glu Arg Thr
    50                  55                  60

Phe Gly Asn Cys Arg Cys Asp Ala Ala Cys Val Glu Leu Gly His Cys
65                  70                  75                  80

Cys Leu Asp Tyr Gln Glu Thr Cys Ile Glu Pro Glu His Ile Trp Thr
                85                  90                  95

Cys Asn Lys Phe Arg Cys Gly Glu Lys Arg Leu Thr Arg Ser Leu Cys
            100                 105                 110

Ala Cys Ser Asp Asp Cys Lys Asp Lys Gly Asp Cys Cys Ile Asn Tyr
        115                 120                 125

Ser Ser Val Cys Gln Gly Glu Lys Ser Trp Val Glu Glu Pro Cys Glu
    130                 135                 140

Ser Ile Asn Glu Pro Gln Cys Pro Ala Gly Phe Glu Thr Pro Pro Thr
145                 150                 155                 160

Leu Leu Phe Ser Leu Asp Gly Phe Arg Ala Glu Tyr Leu His Thr Trp
                165                 170                 175

Gly Gly Leu Leu Pro Val Ile Ser Lys Leu Lys Lys Cys Gly Thr Tyr
            180                 185                 190

Thr Lys Asn Met Arg Pro Val Tyr Pro Thr Lys Thr Phe Pro Asn His
        195                 200                 205

Tyr Ser Ile Val Thr Gly Leu Tyr Pro Glu Ser His Gly Ile Ile Asp
    210                 215                 220

Asn Lys Met Tyr Asp Pro Lys Met Asn Ala Ser Phe Ser Leu Lys Ser
225                 230                 235                 240

Lys Glu Lys Phe Asn Pro Glu Trp Tyr Lys Gly Glu Pro Ile Trp Val
                245                 250                 255

Thr Ala Lys Tyr Gln Gly Leu Lys Ser Gly Thr Phe Phe Trp Pro Gly
            260                 265                 270

Ser Asp Val Glu Ile Asn Gly Ile Phe Pro Asp Ile Tyr Lys Met Tyr
        275                 280                 285

Asn Gly Ser Val Pro Phe Glu Arg Ile Leu Ala Val Leu Gln Trp
    290                 295                 300

Leu Gln Leu Pro Lys Asp Glu Arg Pro His Phe Tyr Thr Leu Tyr Leu
305                 310                 315                 320

Glu Glu Pro Asp Ser Ser Gly His Ser Tyr Gly Pro Val Ser Ser Glu
                325                 330                 335

Val Ile Lys Ala Leu Gln Arg Val Asp Gly Met Val Gly Met Leu Met
            340                 345                 350

Asp Gly Leu Lys Glu Leu Asn Leu His Arg Cys Leu Asn Leu Ile Leu
        355                 360                 365
```

-continued

```
Thr Ser Asp His Gly Met Glu Gln Gly Ser Cys Lys Tyr Ile Tyr
    370                 375                 380

Leu Asn Lys Tyr Leu Gly Asp Val Lys Asn Ile Lys Val Ile Tyr Gly
385                 390                 395                 400

Pro Ala Ala Arg Leu Arg Pro Ser Asp Val Pro Asp Lys Tyr Tyr Ser
                405                 410                 415

Pro Asn Tyr Glu Gly Ile Ala Arg Asn Leu Ser Cys Arg Glu Pro Asn
            420                 425                 430

Gln His Phe Lys Pro Tyr Leu Lys His Gly Leu Pro Lys Arg Leu His
        435                 440                 445

Phe Ala Lys Ser Asp Arg Ile Glu Pro Leu Thr Phe Tyr Leu Asp Pro
    450                 455                 460

Gln Trp Gln Leu Ala Leu Asn Pro Ser Glu Arg Lys Tyr Cys Gly Ser
465                 470                 475                 480

Gly Phe His Gly Ser Asp Asn Val Phe Ser Asn Met Gln Ala Leu Phe
                485                 490                 495

Val Gly Tyr Gly Pro Gly Phe Lys His Gly Ile Glu Ala Asp Thr Phe
            500                 505                 510

Glu Asn Ile Glu Val Tyr Asn Leu Met Cys Asp Leu Leu Asn Leu Thr
        515                 520                 525

Pro Ala Pro Asn Asn Gly Thr His Gly Ser Leu Asn His Leu Leu Lys
    530                 535                 540

Asn Pro Val Tyr Thr Pro Lys His Pro Lys Glu Val His Pro Leu Val
545                 550                 555                 560

Gln Cys Pro Phe Thr Arg Asn Pro Arg Asp Asn Leu Gly Cys Ser Cys
                565                 570                 575

Asn Pro Ser Ile Leu Pro Ile Glu Asp Phe Gln Thr Gln Phe Asn Leu
            580                 585                 590

Thr Val Ala Glu Glu Lys Ile Ile Lys His Glu Thr Leu Pro Tyr Gly
        595                 600                 605

Arg Pro Arg Val Leu Gln Lys Glu Asn Thr Ile Cys Leu Leu Ser Gln
    610                 615                 620

His Gln Phe Met Ser Gly Tyr Ser Gln Asp Ile Leu Met Pro Leu Trp
625                 630                 635                 640

Thr Ser Tyr Thr Val Asp Arg Asn Asp Ser Phe Ser Thr Glu Asp Phe
                645                 650                 655

Ser Asn Cys Leu Tyr Gln Asp Phe Arg Ile Pro Leu Ser Pro Val His
            660                 665                 670

Lys Cys Ser Phe Tyr Lys Asn Asn Thr Lys Val Ser Tyr Gly Phe Leu
        675                 680                 685

Ser Pro Pro Gln Leu Asn Lys Asn Ser Ser Gly Ile Tyr Ser Glu Ala
    690                 695                 700

Leu Leu Thr Thr Asn Ile Val Pro Met Tyr Gln Ser Phe Gln Val Ile
705                 710                 715                 720

Trp Arg Tyr Phe His Asp Thr Leu Leu Arg Lys Tyr Ala Glu Glu Arg
                725                 730                 735

Asn Gly Val Asn Val Val Ser Gly Pro Val Phe Asp Phe Asp Tyr Asp
            740                 745                 750

Gly Arg Cys Asp Ser Leu Glu Asn Leu Arg Gln Lys Arg Arg Val Ile
        755                 760                 765

Arg Asn Gln Glu Ile Leu Ile Pro Thr His Phe Phe Ile Val Leu Thr
    770                 775                 780

Ser Cys Lys Asp Thr Ser Gln Thr Pro Leu His Cys Glu Asn Leu Asp
785                 790                 795                 800
```

-continued

```
Thr Leu Ala Phe Ile Leu Pro His Arg Thr Asp Asn Ser Glu Ser Cys
            805                 810                 815

Val His Gly Lys His Asp Ser Ser Trp Val Glu Glu Leu Leu Met Leu
        820                 825                 830

His Arg Ala Arg Ile Thr Asp Val Glu His Ile Thr Gly Leu Ser Phe
                835                 840                 845

Tyr Gln Gln Arg Lys Glu Pro Val Ser Asp Ile Leu Lys Leu Lys Thr
        850                 855                 860

His Leu Pro Thr Phe Ser Gln Glu Asp
865                 870

<210> SEQ ID NO 71
<211> LENGTH: 979
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Xaa at positions: 864, 889, 905, 911, 927,
      937, 944, 950, 954, 967, 975 represents either an unknown or any
      amino acid residue.

<400> SEQUENCE: 71

Met Ala Arg Arg Ser Ser Phe Gln Ser Cys Gln Asp Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Ala Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Leu Gln Val
145                 150                 155                 160

Cys Ser Pro Ser Ile Asn His Leu Leu Arg Gly Trp Leu Pro Met Thr
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Arg Gly Glu Ser Trp
```

```
                260                 265                 270
Asn Ile Leu Leu Val Cys Cys His Pro Ser Arg Ala Glu Ile Leu Thr
            275                 280                 285
Ile Leu Gln Trp Leu Thr Leu Pro Asp His Glu Arg Pro Ser Val Tyr
        290                 295                 300
Ala Phe Tyr Ser Glu Gln Pro Asp Phe Ser Gly His Lys His Met Pro
305                 310                 315                 320
Phe Gly Pro Glu Met Thr Asn Pro Leu Arg Glu Met His Lys Ile Val
                325                 330                 335
Gly Gln Leu Met Asp Gly Leu Lys Gln Leu Lys Leu His Arg Cys Val
            340                 345                 350
Asn Val Ile Phe Val Glu Thr Met Asp Gly Arg Cys His Met Tyr Arg
        355                 360                 365
Thr Glu Phe Leu Ser Asn Tyr Leu Thr Asn Val Asp Asp Ile Thr Leu
    370                 375                 380
Val Pro Gly Thr Leu Gly Arg Ile Arg Ser Lys Phe Ser Asn Asn Ala
385                 390                 395                 400
Lys Tyr Asp Pro Lys Ala Ile Ile Ala Asn Leu Thr Cys Lys Lys Pro
                405                 410                 415
Asp Gln His Phe Lys Pro Tyr Leu Lys Gln His Leu Pro Lys Arg Leu
            420                 425                 430
His Tyr Ala Asn Asn Arg Arg Ile Glu Asp Ile His Leu Leu Val Glu
        435                 440                 445
Arg Arg Trp His Val Ala Arg Lys Pro Leu Asp Val Tyr Lys Lys Pro
    450                 455                 460
Ser Gly Asn Ala Phe Ser Arg Glu Thr Thr Ala Phe Asp Asn Lys Val
465                 470                 475                 480
Asn Ser Met Gln Thr Val Phe Val Gly Tyr Gly Pro Thr Phe Lys Tyr
                485                 490                 495
Lys Thr Lys Val Pro Pro Phe Glu Asn Ile Glu Leu Tyr Asn Val Met
            500                 505                 510
Cys Asp Leu Leu Gly Leu Lys Pro Ala Pro Asn Asn Gly Thr His Gly
        515                 520                 525
Ser Leu Asn His Leu Leu Arg Thr Asn Thr Phe Arg Pro Thr Met Pro
    530                 535                 540
Glu Glu Val Thr Arg Pro Asn Tyr Pro Gly Ile Met Tyr Leu Gln Ser
545                 550                 555                 560
Asp Phe Asp Leu Gly Cys Thr Cys Asp Asp Lys Val Glu Pro Lys Asn
                565                 570                 575
Lys Leu Asp Glu Leu Asn Lys Arg Leu His Thr Lys Gly Ser Thr Glu
            580                 585                 590
Glu Arg His Leu Leu Tyr Gly Asp Arg Pro Ala Val Leu Tyr Arg Thr
        595                 600                 605
Arg Tyr Asp Ile Leu Tyr His Thr Asp Phe Glu Ser Gly Tyr Ser Glu
    610                 615                 620
Ile Phe Leu Met Pro Leu Trp Thr Ser Tyr Thr Val Ser Lys Gln Ala
625                 630                 635                 640
Glu Val Ser Ser Val Pro Asp His Leu Thr Ser Cys Val Arg Pro Asp
                645                 650                 655
Val Arg Val Ser Pro Ser Phe Ser Gln Asn Cys Leu Ala Tyr Lys Asn
            660                 665                 670
Asp Lys Gln Met Ser Tyr Gly Phe Leu Phe Pro Pro Tyr Leu Ser Ser
        675                 680                 685
```

```
Ser Pro Glu Ala Lys Tyr Asp Ala Phe Leu Val Thr Asn Met Val Pro
    690             695             700
Met Tyr Pro Ala Phe Lys Arg Val Trp Asn Tyr Phe Gln Arg Val Leu
705             710             715             720
Val Lys Lys Tyr Ala Ser Glu Arg Asn Gly Val Asn Val Ile Ser Gly
                725             730             735
Pro Ile Phe Asp Tyr Asp Tyr Asp Gly Leu His Asp Thr Glu Asp Lys
            740             745             750
Ile Lys Gln Tyr Val Glu Gly Ser Ser Ile Pro Val Pro Thr His Tyr
        755             760             765
Tyr Ser Ile Ile Thr Ser Cys Leu Asp Phe Thr Gln Pro Ala Asp Lys
    770             775             780
Cys Asp Gly Pro Leu Ser Val Ser Ser Phe Ile Leu Pro His Arg Pro
785             790             795             800
Asp Asn Glu Glu Ser Cys Asn Ser Ser Glu Asp Glu Ser Lys Trp Val
            805             810             815
Glu Glu Leu Met Lys Met His Thr Ala Arg Val Arg Asp Ile Glu His
        820             825             830
Leu Thr Ser Leu Asp Phe Phe Arg Lys Thr Ser Arg Ser Tyr Pro Glu
        835             840             845
Ile Leu Thr Leu Lys Thr Tyr Leu His His Thr Tyr Glu Ser Glu Ile Xaa
    850             855             860
Leu Ser Glu His Leu Gln Tyr Ser Leu Ile Asn Trp Leu Tyr Ile Phe
865             870             875             880
Ile Leu Phe Leu Tyr Leu Leu Ile Xaa Asn Gln Asp Ile Lys Asn Val
            885             890             895
Ser Ile Leu Ile Leu Tyr Gln Ile Xaa His Ile Met Pro Glu Xaa Leu
            900             905             910
His Cys Phe Ser Leu Met Leu Asp Leu Gly Ser Leu Val Phe Xaa Val
            915             920             925
Glu Leu Val Ile Asn Thr Ala Ala Xaa Val Phe Ser Gly Ser Phe Xaa
    930             935             940
Met Val Leu Gln Ile Xaa Tyr Leu His Xaa Gly Asn Ile Asn Phe Pro
945             950             955             960
Met His Ser Cys His Ile Xaa Ser Cys Thr Val Trp Lys His Xaa Phe
            965             970             975
Cys Lys Val
```